(12) United States Patent
Bennett et al.

(10) Patent No.: US 10,344,282 B2
(45) Date of Patent: Jul. 9, 2019

(54) COMPOSITIONS AND METHODS FOR MODULATION OF IKBKAP SPLICING

(71) Applicants: Ionis Pharmaceuticals, Inc., Carlsbad, CA (US); Cold Spring Harbor Laboratory, Cold Spring Harbor, NY (US)

(72) Inventors: C. Frank Bennett, Carlsbad, CA (US); Frank Rigo, Carlsbad, CA (US); Adrian R. Krainer, Huntington Station, NY (US); Rahul Sinha, Stanford, CA (US)

(73) Assignees: IONIS PHARMACEUTICALS, INC., Carlsbad, CA (US); COLD SPRING HARBOR LABORATORY, Cold Spring Harbor, NY (US)

( * ) Notice: Subject to any disclaimer, the term of this patent is extended or adjusted under 35 U.S.C. 154(b) by 0 days.

(21) Appl. No.: 15/993,090

(22) Filed: May 30, 2018

(65) Prior Publication Data
US 2018/0371457 A1    Dec. 27, 2018

Related U.S. Application Data

(63) Continuation of application No. 14/371,941, filed as application No. PCT/US2013/021311 on Jan. 11, 2013, now abandoned.

(60) Provisional application No. 61/585,579, filed on Jan. 11, 2012.

(51) Int. Cl.
*C12N 15/11* (2006.01)
*C12N 15/113* (2010.01)

(52) U.S. Cl.
CPC .......... *C12N 15/113* (2013.01); *C12N 15/111* (2013.01); *C12N 2310/11* (2013.01); *C12N 2310/113* (2013.01); *C12N 2310/315* (2013.01); *C12N 2310/321* (2013.01); *C12N 2310/322* (2013.01); *C12N 2310/3233* (2013.01); *C12N 2310/3521* (2013.01); *C12N 2310/3525* (2013.01); *C12N 2310/3533* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 2002/0119533 A1* | 8/2002 | Brown | C12Q 1/6844 435/91.1 |
| 2002/0168656 A1* | 11/2002 | Rubin | C12Q 1/6883 435/6.13 |
| 2003/0219770 A1* | 11/2003 | Eshleman | C12Q 1/6869 435/6.14 |
| 2010/0261175 A1* | 10/2010 | Rasmussen | C12N 15/111 435/6.1 |
| 2011/0097716 A1* | 4/2011 | Natt | C12Q 1/6851 435/6.11 |

* cited by examiner

*Primary Examiner* — Richard A Schnizer
(74) *Attorney, Agent, or Firm* — Michael Best & Friedrich LLP

(57) ABSTRACT

The present disclosure provides compounds comprising oligonucleotides complementary to a portion of the IKBKAP gene. Certain such compounds are useful for hybridizing to a portion of the IKBKAP gene, including but not limited to a portion of the IKBKAP gene in a cell. In certain embodiments, such hybridization results in modulation of splicing of the IKBKAP gene. In certain embodiments, the IKBKAP gene includes a mutation that results in defective splicing and a truncated IKAP protein. In certain embodiments, hybridization of oligonucleotides complementary to a portion of the IKBKAP gene results in a decrease in the amount of defective splicing and truncated IKAP protein. In certain embodiments, hybridization of oligonucleotides complementary to a portion of the IKBKAP gene results in an increase in the amount of normal splicing and functional, full-length IKAP protein. In certain embodiments, oligonucleotides are used to treat Familial Dysautonomia.

20 Claims, 7 Drawing Sheets
Specification includes a Sequence Listing.

COMPOSITIONS AND METHODS FOR
MODULATION OF IKBKAP SPLICING

STATEMENT OF GOVERNMENT SUPPORT

This invention was made with government support under GM042699 and CA013106 awarded by The National Institutes of Health. The government has certain rights in the invention.

SEQUENCE LISTING

The present application is being filed along with a Sequence Listing in electronic format. The Sequence Listing is provided as a file entitled CORE0100USC1SEQ.txt, created May 29, 2018, which is 96 kb in size. The information in the electronic format of the sequence listing is incorporated herein by reference in its entirety.

BACKGROUND

Newly synthesized eukaryotic mRNA molecules, also known as primary transcripts or pre-mRNA, made in the nucleus, are processed before or during transport to the cytoplasm for translation. Processing of the pre-mRNAs includes addition of a 5' methylated cap and an approximately 200-250 base poly(A) tail to the 3' end of the transcript.

Another step in mRNA processing is splicing of the pre-mRNA, which occurs in the maturation of 90-95% of mammalian mRNAs. Introns (or intervening sequences) are regions of a primary transcript (or the DNA encoding it) that are not included in the coding sequence of the mature mRNA. Exons are regions of a primary transcript that remain in the mature mRNA when it reaches the cytoplasm. The exons are spliced together to form the mature mRNA sequence. Splice junctions are also referred to as splice sites with the junction at the 5' side of the intron often called the "5' splice site," or "splice donor site" and the junction at the 3' side of the intron called the "3' splice site" or "splice acceptor site." In splicing, the 3' end of an upstream exon is joined to the 5' end of the downstream exon. Thus the unspliced RNA (or pre-mRNA) has an exon/intron junction at the 5' end of an intron and an intron/exon junction at the 3' end of an intron. After the intron is removed, the exons are contiguous at what is sometimes referred to as the exon/exon junction or boundary in the mature mRNA. Cryptic splice sites are those that are not used in wild-type pre-mRNA, but may be used when the natural splice site is inactivated or weakened by mutation, or in conjunction with a mutation that creates a new splice site elsewhere on the pre-mRNA. Alternative splicing, defined as the splicing together of different combinations of exons or exon segments, often results in multiple mature mRNA transcripts expressed from a single gene.

Up to 50% of human genetic diseases resulting from a point mutation are caused by aberrant splicing. Such point mutations can either disrupt a current splice site or create a new splice site, resulting in mRNA transcripts comprised of a different combination of exons or with deletions in exons. Point mutations also can result in activation of a cryptic splice site(s), disrupt a branch site (which functions during an intermediate step in splicing catalysis) or disrupt regulatory cis elements (i.e., splicing enhancers or silencers, which can be created, destroyed, strengthened or weakened by mutation) (Cartegni et al., Nat. Rev. Genet., 2002, 3, 285-298; Crawczak et al., Hum. Genet., 1992, 90, 41-54).

Antisense oligonucleotides have been used to target mutations that lead to aberrant splicing in several genetic diseases in order to redirect splicing to give a desired splice product (Kole, Acta Biochimica Polonica, 1997, 44, 231-238). Such diseases include β-thalassemia (Dominski and Kole, Proc. Natl. Acad. Sci. USA, 1993, 90, 8673-8677; Sierakowska et al., Nucleosides & Nucleotides, 1997, 16, 1173-1182; Sierakowska et al., Proc. Natl. Acad. Sci. USA, 1996, 93, 12840-44; Lacerra et al., Proc. Natl. Acad. Sci. USA, 2000, 97, 9591-9596); dystrophy Kobe (Takeshima et al., J. Clin. Invest., 1995, 95, 515-520); Duchenne muscular dystrophy (Dunckley et al. Nucleosides & Nucleotides, 1997, 16, 1665-1668; Dunckley et al. Human Mol. Genetics, 1998, 5, 1083-90); osteogenesis imperfecta (Wang and Marini, J. Clin Invest., 1996, 97, 448-454); and cystic fibrosis (Friedman et al., J. Biol. Chem., 1999, 274, 36193-36199).

Antisense compounds have also been used to alter the ratio of the long and short forms of Bcl-x pre-mRNA (U.S. Pat. Nos. 6,172,216; 6,214,986; Taylor et al., Nat. Biotechnol. 1999, 17, 1097-1100) or to force skipping of specific exons containing premature termination codons (Wilton et al., Neuromuscul. Disord., 1999, 9, 330-338). U.S. Pat. No. 5,627,274 and WO 94/26887 disclose compositions and methods for combating aberrant splicing in a pre-mRNA molecule containing a mutation using antisense oligonucleotides which do not activate RNAse H.

Antisense compounds targeting splicing-inhibitory elements in exons or their flanking introns have also been used to increase the use of such exons during splicing, e.g., in the context of spinal muscular atrophy (Cartegni Nat Struct Biol; Imaizumi; Hua PLoS Biol; Singh; other Hua et al papers, etc.).

Familial dysautonomia (FD), a rare genetic disorder found almost exclusively in the Ashkenazi Jewish population, is an autosomal recessive condition that is caused by a single intronic point mutation in intron 20 (IVS20+6T→C) of the IKBKAP gene (Maayan, C., Kaplan, E., Shachar, S., Peleg, O., and Godfrey, S. 1987, "Incidence of familial dysautonomia in Israel 1977-1981," Clin Genet 32:106-108; Slaugenhaupt, S. A., and Gusella, J. F. 2002, "Familial dysautonomia," Curr Opin Genet Dev 12:307-311; Anderson, S. L., Coli, R., Daly, I. W., Kichula, E. A., Rork, M. J., Volpi, S. A., Ekstein, J., and Rubin, B. Y. 2001, "Familial dysautonomia is caused by mutations of the IKAP gene," Am J Hum Genet 68:753-758). FD, also known as Riley-Day syndrome and hereditary sensory autonomic neuropathy type-III (HSAN-III), is characterized by poor development and progressive degeneration of sensory and autonomic neurons. Notable symptoms include anhidrosis, decreased taste, depressed deep tendon reflexes, postural hypotension, loss of pain and temperature perception, alacrima, gastroesophageal reflux, and scoliosis (Axelrod, F. B., and Simson, G. G. V. 2007 "Hereditary sensory and autonomic neuropathies: types II, III, and IV," Orphanet Journal of Rare Diseases 2:). The extent and severity of the symptoms vary among patients, but even with advanced management, the disease leads to premature death, with only half of the patients surviving to 40 years of age.

Antisense technology is an effective means for modulating the expression of one or more specific gene products, including alternative splice products, and is uniquely useful in a number of therapeutic, diagnostic, and research applications. The principle behind antisense technology is that an antisense compound, which hybridizes to a target nucleic acid, modulates gene expression activities, such as transcription, splicing or translation, through one of a number of antisense mechanisms. The sequence specificity of antisense compounds makes them extremely attractive as tools for target validation and gene functionalization, as well as therapeutics to selectively modulate the expression of genes involved in disease.

SUMMARY

In certain embodiments, the present disclosure provides compounds comprising oligonucleotides. In certain embodiments, such oligonucleotides are complementary to an IKB-KAP transcript. In certain such embodiments, the oligonucleotide is complementary to a target region of the IKBKAP transcript comprising exon 20, intron 19, and intron 20. In certain embodiments, the IKBKAP transcript comprises a mutation that results in an aberrant splice site. In certain embodiments, the IKBKAP transcript comprises a mutation that results in the exclusion of exon 20 from the mature IKBKAP mRNA. In certain embodiments, oligonucleotides inhibit aberrant splicing of a mutant IKBKAP transcript. In certain such embodiments, normal splicing of the IKBKAP transcript is increased. In certain embodiments, functional IKAP protein having exon 20 is increased. In certain embodiments, functional IKAP protein having exons 20-37 is increased.

The present disclosure provides the following non-limiting numbered embodiments:

Embodiment 1

A compound comprising a modified oligonucleotide consisting of 8 to 30 linked nucleosides and having a nucleobase sequence comprising at least 8 contiguous nucleobases complementary to a target region of equal length of an IKBKAP transcript.

Embodiment 2

The compound of embodiment 1, wherein nucleobase sequence comprises at least 8 contiguous nucleobases complementary to intron 19, intron 20, or exon 20 of an IKBKAP transcript.

Embodiment 3

The compound of any of embodiments 1 to 2, wherein the modified oligonucleotide is 12 to 20 nucleosides in length.

Embodiment 4

The compound of any of embodiments 1 to 2, wherein the modified oligonucleotide is 14 to 16 nucleosides in length.

Embodiment 5

The compound of any of embodiments 1 to 2, wherein the oligonucleotide is 12 nucleosides in length.

Embodiment 6

The compound of any of embodiments 1 to 2, wherein the oligonucleotide is 14 nucleosides in length.

Embodiment 7

The compound of any of embodiments 1 to 2, wherein the oligonucleotide is 15 nucleosides in length.

Embodiment 8

The compound of any of embodiments 1 to 2, wherein the oligonucleotide is 16 nucleosides in length.

Embodiment 9

The compound of any of embodiments 1 to 2, wherein the oligonucleotide is 20 nucleosides in length.

Embodiment 10

The compound of any of embodiments 1 to 10 having a nucleobase sequence comprising at least 9 contiguous nucleobases complementary to a target region of equal length of an IKBKAP transcript.

Embodiment 11

The compound of any of embodiments 1 to 10 having a nucleobase sequence comprising at least 10 contiguous nucleobases complementary to a target region of equal length of an IKBKAP transcript.

Embodiment 12

The compound of any of embodiments 1 to 10 having a nucleobase sequence comprising at least 11 contiguous nucleobases complementary to a target region of equal length of an IKBKAP transcript.

Embodiment 13

The compound of any of embodiments 1 to 10 having a nucleobase sequence comprising at least 12 contiguous nucleobases complementary to a target region of equal length of an IKBKAP transcript.

Embodiment 14

The compound of any of embodiments 1 to 6 having a nucleobase sequence comprising at least 13 contiguous nucleobases complementary to a target region of equal length of an IKBKAP transcript.

Embodiment 15

The compound of any of embodiments 1 to 6 having a nucleobase sequence comprising at least 14 contiguous nucleobases complementary to a target region of equal length of an IKBKAP transcript.

Embodiment 16

The compound of any of embodiments 1 to 4 or 7 having a nucleobase sequence comprising at least 15 contiguous nucleobases complementary to a target region of equal length of an IKBKAP transcript.

Embodiment 17

The compound of any of embodiments 1 to 4 or 8 having a nucleobase sequence comprising at least 16 contiguous nucleobases complementary to a target region of equal length of an IKBKAP transcript.

Embodiment 18

The compound of any of embodiments 1 to 4 or 9 having a nucleobase sequence comprising at least 17 contiguous nucleobases complementary to a target region of equal length of an IKBKAP transcript.

Embodiment 19

The compound of any of embodiments 1 to 4 or 10 having a nucleobase sequence comprising at least 18 contiguous nucleobases complementary to a target region of equal length of an IKBKAP transcript.

Embodiment 20

The compound of any of embodiments 1 to 19, wherein the modified oligonucleotide comprises at least one modified nucleoside.

Embodiment 21

The compound of any of embodiments 1 to 20, wherein at least one modified nucleoside comprises a modified sugar moiety.

Embodiment 22

The compound of embodiment 21, wherein at least one modified sugar moiety is a 2'-substituted sugar moiety.

Embodiment 23

The compound of embodiment 22, wherein the 2'-substitutent of at least one 2'-substituted sugar moiety is selected from the group consisting of 2'-OMe, 2'-F, and 2'-MOE.

Embodiment 24

The compound of embodiment 23, wherein the 2'-substituent of at least one 2'-substituted sugar moiety is a 2'-MOE.

Embodiment 25

The compound of any of embodiments 1 to 21, wherein at least one modified sugar moiety is a bicyclic sugar moiety.

Embodiment 26

The compound of embodiment 25, wherein at least one bicyclic sugar moiety is LNA or cEt.

Embodiment 27

The compound of any of embodiments 1 to 21, wherein at least one sugar moiety is a sugar surrogate.

Embodiment 28

The compound of embodiment 27, wherein at least one sugar surrogate is a morpholino.

Embodiment 29

The compound of embodiment 27, wherein at least one sugar surrogate is a modified morpholino.

Embodiment 30

The compound of any of embodiments 1 to 29, wherein each nucleoside of the modified oligonucleotide is a modified nucleoside, each independently comprising a modified sugar moiety.

Embodiment 31

The compound of any of embodiments 1 to 29, wherein the modified oligonucleotide comprises at least two modified nucleosides comprising modified sugar moieties that are the same as one another.

Embodiment 32

The compound of any of embodiments 1 to 29, wherein the modified oligonucleotide comprises at least two modified nucleosides comprising modified sugar moieties that are different from one another.

Embodiment 33

The compound of any of embodiments 1 to 30, wherein each nucleoside of the modified oligonucleotide is a modified nucleoside.

Embodiment 34

The compound of any of embodiments 1 to 30, wherein each nucleoside of the modified oligonucleotide is a modified nucleoside, and each modified nucleoside comprises the same modification.

Embodiment 35

The compound of embodiment 34, wherein the modified nucleosides each comprise the same 2'-substituted sugar moiety.

Embodiment 36

The compound of embodiment 35, wherein the 2'-substituted sugar moiety is selected from 2'-F, 2'-OMe, and 2'-MOE.

Embodiment 37

The compound of embodiment 36, wherein the 2'-substituted sugar moiety is 2'-MOE.

Embodiment 38

The compound of any of embodiments 1 to 37, wherein at least one internucleoside linkage is a modified internucleoside linkage.

Embodiment 39

The oligonucleotide of any of embodiments 1 to 38, wherein each internucleoside linkage is a modified internucleoside linkage.

Embodiment 40

The compound of any of embodiments 1 to 39, wherein the modified internucleoside linkage is phosphorothioate.

Embodiment 41

The compound of any of embodiments 1 to 40, wherein the oligonucleotide is targeted to an intronic splicing silencer element.

Embodiment 42

The compound of any of embodiments 1 to 40, wherein the oligonucleotide is targeted to an exonic splicing silencer element.

Embodiment 43

The compound any of embodiments 1 to 40, wherein nucleobase sequence comprises at least 8 contiguous nucleobases complementary to intron 19, intron 20, or exon 20 of a nucleic acid molecule encoding IKAP.

Embodiment 44

The compound of any of embodiments 1 to 40, wherein the oligonucleotide is targeted to intron 19.

Embodiment 45

The compound of any of embodiments 1 to 40, wherein the oligonucleotide is targeted to intron 20.

Embodiment 46

The compound of any of embodiments 1 to 40, wherein the oligonucleotide is targeted to exon 20.

Embodiment 47

The compound of any of embodiments 1 to 46, wherein the oligonucleotide comprises a nucleobase sequence comprising a portion of at least 8 contiguous nucleobases complementary to an equal length portion of nucleobases 34622 to 34895 of SEQ ID NO: 1.

Embodiment 48

The compound of any of embodiments 1 to 46, wherein the oligonucleotide comprises a nucleobase sequence comprising a portion of at least 8 contiguous nucleobases complementary to an equal length portion of nucleobases 34622 to 34721 of SEQ ID NO: 1.

Embodiment 49

The compound of any of embodiments 1 to 46, wherein the oligonucleotide comprises a nucleobase sequence comprising a portion of at least 8 contiguous nucleobases complementary to an equal length portion of nucleobases 34722 to 34795 of SEQ ID NO: 1.

Embodiment 50

The compound of any of embodiments 1 to 46, wherein the oligonucleotide comprises a nucleobase sequence comprising a portion of at least 8 contiguous nucleobases complementary to an equal length portion of nucleobases 34796 to 34881 of SEQ ID NO: 1.

Embodiment 51

The compound of any of embodiments 1 to 46, wherein the oligonucleotide comprises a nucleobase sequence comprising a portion of at least 8 contiguous nucleobases complementary to an equal length portion of nucleobases 34722 to 34795 of SEQ ID NO: 1.

Embodiment 52

The compound of any of embodiments 1 to 46, wherein the oligonucleotide comprises a nucleobase sequence comprising a portion of at least 8 contiguous nucleobases complementary to an equal length portion of nucleobases 34801 to 34828 of SEQ ID NO: 1.

Embodiment 53

The compound of any of embodiments 1 to 46, wherein the oligonucleotide comprises a nucleobase sequence comprising a portion of at least 8 contiguous nucleobases complementary to an equal length portion of nucleobases 34801 to 34826 of SEQ ID NO: 1.

Embodiment 54

The compound of any of embodiments 1 to 46, wherein the oligonucleotide comprises a nucleobase sequence comprising a portion of at least 8 contiguous nucleobases complementary to an equal length portion of nucleobases 34802 to 34821 of SEQ ID NO: 1.

Embodiment 55

The compound of any of embodiments 1 to 46, wherein the oligonucleotide comprises a nucleobase sequence comprising an at least 8 nucleobase portion of SEQ ID NO: 60, 61, 62, 63, 64, 65, 66, 67, or 68.

Embodiment 56

The compound of any of embodiments 1 to 46, wherein the oligonucleotide comprises a nucleobase sequence comprising an at least 8 nucleobase portion of SEQ ID NO: 60.

Embodiment 57

The compound of any of embodiments 1 to 46, wherein the oligonucleotide comprises a nucleobase sequence comprising an at least 8 nucleobase portion of SEQ ID NO: 61.

Embodiment 58

The compound of any of embodiments 1 to 46, wherein the oligonucleotide comprises a nucleobase sequence comprising an at least 8 nucleobase portion of SEQ ID NO: 62.

Embodiment 59

The compound of any of embodiments 1 to 46, wherein the oligonucleotide comprises a nucleobase sequence comprising an at least 8 nucleobase portion of SEQ ID NO: 63.

Embodiment 60

The compound of any of embodiments 1 to 46, wherein the oligonucleotide comprises a nucleobase sequence comprising an at least 8 nucleobase portion of SEQ ID NO: 64.

Embodiment 61

The compound of any of embodiments 1 to 46, wherein the oligonucleotide comprises a nucleobase sequence comprising an at least 8 nucleobase portion of SEQ ID NO: 65.

Embodiment 62

The compound of any of embodiments 1 to 46, wherein the oligonucleotide comprises a nucleobase sequence comprises an at least 8 nucleobase portion of SEQ ID NO: 66.

Embodiment 63

The compound of any of embodiments 1 to 46, wherein the oligonucleotide comprises a nucleobase sequence comprising an at least 8 nucleobase portion of SEQ ID NO: 67.

Embodiment 64

The compound of any of embodiments 1 to 46, wherein the oligonucleotide comprises a nucleobase sequence comprising an at least 8 nucleobase portion of SEQ ID NO: 68.

Embodiment 65

The compound of any of embodiments 1 to 46, wherein the oligonucleotide comprises a nucleobase sequence comprising an at least 8 nucleobase portion of SEQ ID NO: 40, 41, 42, 43, or 44.

Embodiment 66

The compound of any of embodiments 1 to 46, wherein the oligonucleotide comprises a nucleobase sequence comprising an at least 8 nucleobase portion of SEQ ID NO: 40.

Embodiment 67

The compound of any of embodiments 1 to 46, wherein the oligonucleotide comprises a nucleobase sequence comprising an at least 8 nucleobase portion of SEQ ID NO: 41.

Embodiment 68

The compound of any of embodiments 1 to 46, wherein the oligonucleotide comprises a nucleobase sequence comprising an at least 8 nucleobase portion of SEQ ID NO: 42.

Embodiment 69

The compound of any of embodiments 1 to 46, wherein the oligonucleotide comprises a nucleobase sequence comprising an at least 8 nucleobase portion of SEQ ID NO: 43.

Embodiment 70

The compound of any of embodiments 1 to 46, wherein the oligonucleotide comprises a nucleobase sequence comprising an at least 8 nucleobase portion of SEQ ID NO: 44.

Embodiment 71

A pharmaceutical composition comprising the compound of any of embodiments 1 to 70, and a pharmaceutically acceptable carrier or diluent.

Embodiment 72

A method of modulating splicing in an IKBKAP transcript in a cell comprising contacting the cell with a compound according to any of embodiments 1 to 70.

Embodiment 73

A method of increasing inclusion of exon 20 in an IKBKAP transcript, comprising contacting a cell with the compound of any of embodiments 1 to 70.

Embodiment 74

A method of increasing functional IKAP protein in a cell, comprising contacting the cell with a compound according to any of embodiments 1 to 70.

Embodiment 75

A method of increasing IKAP protein having amino acids encoded by exons 20-37 in a cell, comprising contacting the cell with a compound according to any of embodiments 1 to 70.

Embodiment 76

A method for treating a condition characterized at least in part by defective splicing of an IKBKAP transcript, comprising administering a therapeutically effective amount of the compound of any of embodiments 1 to 70, to a subject in need thereof.

Embodiment 77

Use of the compound of any of embodiments 1 to 70 for the preparation of a medicament for increasing inclusion of exon 20 in an IKBKAP transcript.

Embodiment 78

Use of the compound of any of embodiments 1 to 70 for the preparation of a medicament for the treatment of Familial Dysautonomia.

Embodiment 79

A compound of any of embodiments 1 to 70 for use in treating Familial Dysautonomia.

Embodiment 80

The method of any of embodiments 72 to 76, wherein the antisense compound is administered into the central nervous system.

Embodiment 81

The method of any of embodiments 72 to 76, wherein the antisense compound is administered systemically.

Embodiment 82

Then method of any of embodiments 72 to 76, wherein the systemic administration is by intravenous or intraperitoneal injection.

Embodiment 83

Then method of any of embodiments 72 to 76, wherein the systemic administration is by introcerebroventricular injection.

Embodiment 84

The method of any of embodiments 72 to 76, wherein the systemic administration and the administration into the central nervous system are performed at the same time.

BRIEF DESCRIPTION OF THE DRAWINGS

FIGS. 2A, 2B, 2D, and 2F illustrate the inclusion percentages of IKBKAP exon 20 in response to different doses of antisense oligonucleotide compounds. FIGS. 2C and 2F illustrate inclusion percentages of IKBKAP exon 20 in different tissues from ICV or subcutaneous injections.

DETAILED DESCRIPTION

Figure 1A:
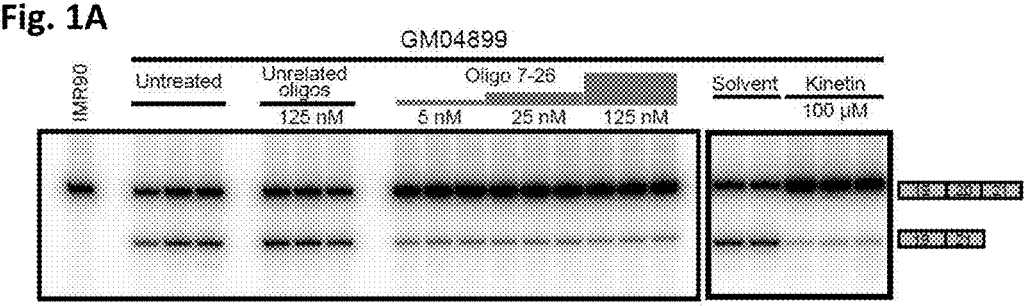
FIGS. 1A-D. These figures illustrate inclusion levels of exon 20.
Figure 1B:
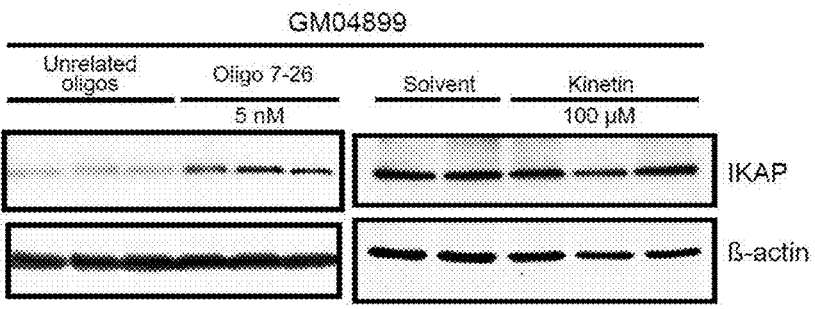
Figure 1C:
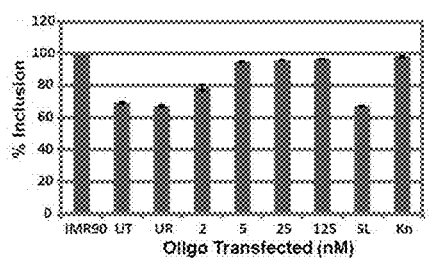
Figure 1D:
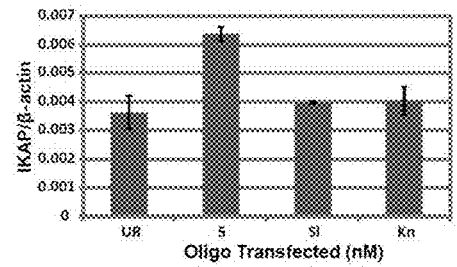

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "IKBKAP Transcript" means a transcript transcribed from an IKBKAP Gene.

As used herein, "IKBKAP Gene" means GENBANK Accession No NT_008470.16 truncated from nucleotides 13290828 to Ser. No. 13/358,424, designated herein as SEQ ID NO: 1.

As used herein, "aberrant splice site" means a splice site that results from a mutation in the native DNA and mRNA. In certain embodiments, aberrant splice sites result in mRNA transcripts comprised of a different combination of exons. In certain embodiments, aberrant splice sites result in mRNA transcripts with deletions of exons. In certain embodiments, aberrant splice sites result in mRNA transcripts with deletions of portions of exons, or with extensions of exons, or with new exons. In certain embodiments, aberrant splice sites result in mRNA transcripts comprising premature stop codons.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to furanosyls comprising substituents at the 2'-position, the 3'-position, the 5'-position and/or the 4'-position.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e., no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atoms attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenylation, addition of 5'-cap, mRNA turnover), and translation and post-translational modification.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more introns.

As used herein, "transcript" means an RNA molecule transcribed from DNA. Transcripts include, but are not limited to mRNA, pre-mRNA, and partially processed RNA.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group, such as an alkyl or hydrocarbyl group, to a parent compound.

Likewise, as used herein, "substituent" in reference to a chemical functional group means an atom or group of atoms differs from the atom or group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)—($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications to one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; O—C$_1$-C$_{10}$ alkoxy; O—C$_1$-C$_{10}$ substituted alkoxy, OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—C$_1$-C$_{10}$ alkoxy; O—C$_1$-C$_{10}$ substituted alkoxy, SH, CN, OCN, CF$_3$, OCF$_3$, O-alkyl, S-alkyl, N(R$_m$)-alkyl; O-alkenyl, S-alkenyl, or N(R$_m$)-alkenyl; O-alkynyl, S-alkynyl, N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$ SCH$_3$, O—(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH (CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH₂—O—N(CH₃)-2' (see, e.g., US2004/0171570, published Sep. 2, 2004); 4'-CH₂—O—N(R)-2', and 4'-CH₂—N(R)—O-2'-, wherein each R is, independently, H, a protecting group, or $C_1$-$C_{12}$ alkyl; 4'-CH₂—N(R)—O-2', wherein R is H, $C_1$-$C_{12}$ alkyl, or a protecting group (see U.S. Pat. No. 7,427,672, issued on Sep. 23, 2008); 4'-CH₂—C(H)(CH₃)-2' (see, e.g., Chattopadhyaya, et al., *J. Org. Chem.*, 2009, 74, 118-134); and 4'-CH₂—C(=CH₂)-2' and analogs thereof (see PCT International Application WO 2008/154401, published on Dec. 8, 2008).

In certain embodiments, such 4' to 2' bridges independently comprise from 1 to 4 linked groups independently selected from —[C($R_a$)($R_b$)]$_n$—, —C($R_a$)=C($R_b$)—, —C($R_a$)=N—, —C(=N$R_a$)—, —C(=O)—, —C(=S)—, —O—, —Si($R_a$)₂—, —S(=O)$_x$-, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)₂-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH₂—O-2') BNA, (B) β-D-Methyleneoxy (4'-CH₂—O-2') BNA (also referred to as locked nucleic acid or LNA), (C) Ethyleneoxy (4'-(CH₂)₂—O-2') BNA, (D) Aminooxy (4'-CH₂—O—N(R)-2') BNA, (E) Oxyamino (4'-CH₂—N(R)—O-2') BNA, (F) Methyl(methyleneoxy) (4'-CH(CH₃)—O-2') BNA (also referred to as constrained ethyl or cEt), (G) methylene-thio (4'-CH₂—S-2') BNA, (H) methylene-amino (4'-CH2-N(R)-2') BNA, (I) methyl carbocyclic (4'-CH₂—CH(CH₃)-2') BNA, and (J) propylene carbocyclic (4'-(CH₂)₃-2') BNA as depicted below.

(A)

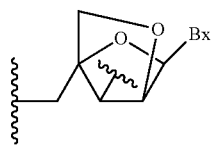

(B)

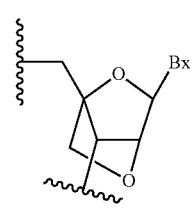

(C)

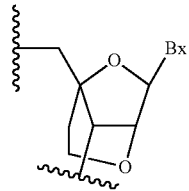

(D)

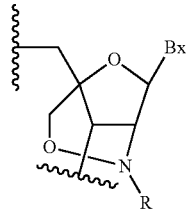

(E)

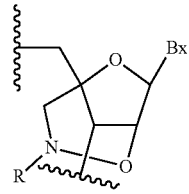

(F)

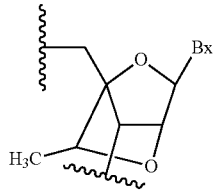

(G)

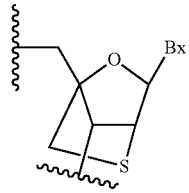

(H)

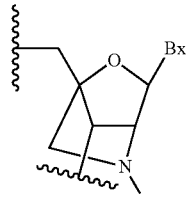

(H)

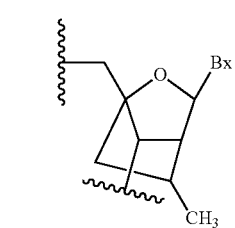

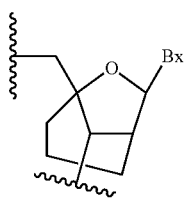

(I)

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. USA.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occuring sugar is substituted, e.g., with a sulfur, carbon or nitrogen atom. In certain such embodiments, such modified sugar moiety also comprises bridging and/or non-bridging substituents as described above. For example, certain sugar surogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

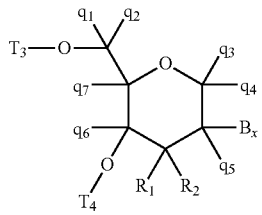

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry*, 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166, 315; 5,185,444; and 5,034,506). As used here, the term "morpholino" means a sugar surrogate having the following structure:

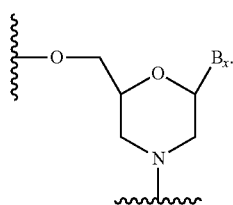

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyl-adenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, or 20 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments, the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucleic Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucleic Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as a chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

Certain Target Nucleic Acids and Mechanisms

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a pre-mRNA. In certain embodiments, the target nucleic acid is an IKBKAP transcript. In certain embodiments, the target RNA is an IKBKAP pre-mRNA.

In certain embodiments, an antisense compound is complementary to a region of an IKBKAP pre-mRNA. In certain embodiments, an antisense compound is complementary within a region of an IKBKAP pre-mRNA comprising intron 19, intron 20, or exon 20. In certain embodiments, an antisense compound is complementary to a region of an IKBKAP pre-mRNA consisting of intron 19, intron 20, or exon 20. In certain embodiments, an antisense compound is complementary to a region of an IKBKAP pre-mRNA consisting of exon 20 or intron 20. In certain embodiments, an antisense compound is complementary to a region of an IKBKAP pre-mRNA within intron 19. In certain embodiments, an antisense compound is complementary to a region of an IKBKAP pre-mRNA within intron 20. In certain embodiments, an antisense compound is complementary to a region of an IKBKAP pre-mRNA within exon 20.

In certain embodiments, an antisense oligonucleotide modulates splicing of a pre-mRNA. In certain embodiments, an antisense oligonucleotide modulates splicing an IKBKAP pre-mRNA. In certain such embodiments, the IKBKAP pre-mRNA is transcribed from a mutant variant of IKBKAP. In certain embodiments, the mutant variant comprises an aberrant splice site. In certain embodiments, the aberrant splice site of the mutant variant comprises a mutation that weakens the 5'-splice site of exon 20. In certain embodiments, an antisense oligonucleotide reduces aberrant splicing of an IKBKAP pre-mRNA. In certain embodiments, an antisense oligonucleotide increases the amount of exon 20 included in normally spliced IKBKAP mRNA. In certain embodiments, an antisense oligonucleotide increases the amount of exon 20 skipped IKBKAP mRNA.

Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the eyes, ears).

In certain embodiments, a pharmaceutical composition is administered to an animal having at least one symptom associated with Familial Dysautonomia. In certain embodiments, such administration results in amelioration of at least one symptom. In certain embodiments, administration of a pharmaceutical composition to an animal results in a decrease of aberrantly spliced IKBKAP mRNA in a cell of the animal. In certain embodiments, such administration results in an increase in normally spliced IKBKAP mRNA and/or an increase in mRNA containing exon 20. In certain embodiments, such administration results in an increase in normally spliced IKBKAP mRNA and/or an increase in mRNA containing exons 20-37. In certain embodiments, such administration results in an increase in normally spliced IKBKAP mRNA and/or a decrease in exon 20 skipped mRNA. In certain embodiments, such administration results in a decrease in truncated IKAP protein and an increase in normal IKAP protein. In certain embodiments, administration of a pharmaceutical composition results in amelioration of: anhidrosis, decreased taste, depressed deep tendon reflexes, postural hypertension, loss of pain and temperature perception, alacrima, gastroesophageal reflux, and scoliosis. In certain embodiments, such amelioration is the reduction in severity of such defects. In certain embodiments, amelioration is the delayed onset of such defects. In certain embodiments, amelioration is the slowed progression of such defects. In certain embodiments, amelioration is the prevention of such defects. In certain embodiments, amelioration is the slowed progression of such defects. In certain embodiments, amelioration is the reversal of such defects.

In certain embodiments, one tests an animal for defects in the IKBKAP gene. In certain embodiments, one identifies an animal having one or more splicing defects in the IKBKAP gene. In certain embodiments, a pharmaceutical composition is administered to an animal identified as having a defect in the IKBKAP gene. In certain embodiments, the animal is tested following administration.

In certain embodiments, one tests for defects in a human IKBKAP transgene. In certain embodiments, one identifies an animal having one or more splicing defects in a human IKBKAP transgene. In certain embodiments, a pharmaceutical composition is administered to an animal identified as having a defect in a human IKBKAP transgene. In certain embodiments, the animal is tested following administration.

In certain embodiments, one tests an animal for defects in a mouse Ikbkap gene. In certain embodiments, one identifies an animal having one or more splicing defects in a mouse Ikbkap gene. In certain embodiments, a pharmaceutical composition is administered to an animal identified as having a defect in the IKBKAP gene. In certain embodiments, the animal is tested following administration.

The disclosure also provides an antisense compound as described herein, for use in any of the methods as described herein. For example, the invention provides an antisense compound comprising an antisense oligonucleotide for use in treating a disease or condition associated FD by administering the antisense compound directly into the central nervous system (CNS) or cerebrospinal fluid (CSF).

In certain embodiments, the antisense compound is administered systemically. In certain embodiments, the systemic administration is by intravenous or intraperitoneal injection. In certain embodiments, systemic administration and the administration into the central nervous system are performed at the same time. In certain embodiments, systemic administration and the administration into the central nervous system are performed at different times.

In certain embodiments, the invention provides systemic administration of antisense compounds, either alone or in combination with delivery into the CSF. In certain embodiments, pharmaceutical compositions are administered systemically. In certain embodiments, pharmaceutical compositions are administered subcutaneously. In certain embodiments, pharmaceutical compositions are administered intravenously. In certain embodiments, pharmaceutical compositions are administered by intramuscular injection.

In certain embodiments, pharmaceutical compositions are administered both directly to the CSF (e.g., IT and/or ICV injection and/or infusion) and systemically.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Construction of Minigenes Containing Genomic Fragments of the Inhibitor-Kappa B Kinase Associated Protein (IKBKAP) Gene Familial dysautonomia (FD) is caused by a point mutation at the 5' splice site of intron 20, leading to aberrant splicing and the skipping of exon 20 of the IKBKAP genomic sequence (Anderson, S. L. et al., 2001. *Am J Hum Genet* 68:753-758). Hence, IKBKAP minigenes were constructed by cloning the genomic fragments comprising either exon 19 to exon 21 (designated herein as wt19-21) or exon 19 to exon 22 (designated herein as wt19-22).

The IKBKAP genomic fragments spanning exons 19-21 and 19-22 were amplified using specific primers. The genomic fragment for wt19-21 was amplified using the forward primer sequnce IKAP19F6 (GGGGAAGGATC-CGCCATGGAGTTAATGGTGTGTTTAGCATTACAGG, designated herein as SEQ ID NO: 2) and reverse primer sequence IKAP21R3 (GGGGAATCTAGACTTAGGGT-TATG ATCATAAATCAGATTGAG, designated herein as SEQ ID NO: 3). The genomic fragment for wt19-22 was amplified using the forward primer sequence IKAP19F6 and reverse primer sequence IKAP22R (GGGGAATCTAGAT-TACTTCAATTCTGTAAAAAACAAGTTAATATG, designated herein as SEQ ID NO: 4). The IKBKAP gene in human genomic DNA (Promega) was used as a template. The major mutation found in FD (IVS20+6T→C) (Dong, J. et al., 2002. Am. J. Med. Genet. 110: 253-257) was introduced into both the wt19-21 and wt19-22 minigenes by site-directed mutagenesis to create the minigenes mt19-21 and mt19-22. All four minigene fragments were individually cloned into the mammalian expression vector, pCDNA3.1 (Invitrogen). An in-frame ATG as a first codon within a Kozak consensus sequence at the 5' end, downstream of the cytomegalovirus promoter, as well as a stop codon at the 3' end, upstream of a poly(A) signal from the pCDNA3.1 vector were also introduced (FIG. 4).

Each minigene vector construct was transfected individually into HEK-293 cells cultured in Dulbecco's modified Eagle's medium (Invitrogen) supplemented with 10% (v/v) fetal bovine serum. The transfection was conducted by electroporation (Gene Pulsar II apparatus, Bio-Rad) to co-transfect 3 µg of the construct into $7 \times 10^5$ HEK-293 cells resuspended in 70 µL volume of Optimem (Invitrogen) and plated in 6-well plates, as described previously (Hua, Y., et al., 2007. PLoS Biol 5:e73). After 72 hrs, cDNA synthesized from total RNA extracted from HEK-293 cells was amplified, as described previously (Hua, Y., et al., 2007. PLoS Biol 5:e73). wt19-21 and mt19-21 were amplified with forward primer pCDNAF (TAATACGACTCACTATAGGG, designated herein as SEQ ID NO: 5) and reverse primer IKAP21R4 (CTTAGGGTTATGATCATAAATCAG, designated herein as SEQ ID NO: 6). wt19-22 and mt-19-22 were amplified with forward primer pCDNAF and reverse primer IKAP22R2 (TTCAATTCTGTAAAAAACAAG, designated herein as SEQ ID NO: 7). Consistent predominant skipping of exon 20 was observed in the mutant versions of the minigenes, thus recapitulating the aberrant splicing observed in FD patients.

Example 2: Effect of Antisense Oligonucleotides on Exon 20 Skipping in the IKBKAP Minigenes Antisense oligonucleotides were designed targeting a human IKBKAP nucleic acid and were tested for their effects on IKBKAP pre-mRNA in vitro. Together, the overlapping antisense oligonucleotides spanned the entire 74-nucleotide region of the IKBKAP exon 20 sequence, as well as the 100-nucleotide intronic regions immediately upstream and downstream of exon 20. The antisense oligonucleotides are presented in Table 1, and were designed as uniform 2'-O-methoxyethyl ribose (MOE) oligonucleotides with phosphate backbones. Each oligonucleotide is 15 nucleosides in length. All cytosine residues throughout the oligonucleotide are 5-methylcytosines. 'Start Site' indicates the 5'-most nucleoside to which the oligonucleotide is targeted in the human gene sequence. "Stop site" indicates the 3'-most nucleoside to which the oligonucleotide is targeted in the human gene sequence. Each oligonucleotide listed in Table 1 is targeted to the human IKBKAP genomic sequence (the complement of GENBANK Accession No NT_008470.16 truncated from nucleotides 13290828 to Ser. No. 13/358,424, designated herein as SEQ ID NO: 1). ISIS 414161 has one mismatch with SEQ ID NO: 1.

Cultured HEK-293 cells harboring the mt19-21 minigene vector construct at a density of $7 \times 10^5$ cells per well were transfected using electroporation (Gene Pulsar II apparatus, Bio-Rad) with 0.007 nmol antisense oligonucleotide, as previously described (Hua, Y., et al., 2007. PLoS Biol 5:e73). ISIS 383548, ISIS 383553, and ISIS 383874, which were used as control oligonucleotides that do not cause any exon skipping, were similarly transfected. These oligonucleotides served as controls for non-specific effects of uniform MOE oligonucleotides with phosphate backbones. Cells harboring the wt19-21 minigene and the mt19-21 minigene alone were also cultured and were used as controls for exon 20 inclusion levels. Two days later, cDNA synthesized from total RNA extracted from HEK-293 cells was amplified using the forward primer pCDNAF and reverse primer sequence IKAP21R4 to assay the splicing pattern of expressed RNAs by RT-PCR. To calculate exon 20 inclusion levels, the PCR amplicons were labeled with $\alpha^{32}$P-dCTP. The PCR products were then separated by native PAGE, followed by phosphorimage analysis on a FUJIFILM FLA-5100 instrument (Fuji Medical Systems USA Inc.). The band intensities were quantified using Multi Gauge software Version 2.3 (FUJIFILM), and values were normalized for the G+C content according to the DNA sequence.

The results are presented in Table 1 and FIG. 4. The results indicate that 6 consecutive antisense oligonucleotides, ISIS 414161, ISIS 414162, ISIS 414163, ISIS 414164, ISIS 414165, and ISIS 414166, targeting a 40-nucleotide intronic region immediately downstream of the 5' splice site of exon 20 markedly increased inclusion of exon 20. This suggests the presence of multiple splicing silencer elements or inhibitory secondary structures within this region, designated herein as ISS-40. Three more antisense oligonucleotides, ISIS 414135, ISIS 414136, and ISIS 414137, which target a 20-nucleotide region in the upstream intron 19 (designated herein as ISS-20) also had a positive effect on exon 20 inclusion (Table 1 and FIG. 4). Antisense oligonucleotides targeting exon 20 resulted in near-complete exon skipping. Treatment with antisense oligonucleotides targeting the 3' and 5' splice sites caused increased skipping of exon 20. Certain other antisense oligonucleotides targeting intronic regions also caused increased skipping because they targeted important cis-acting splicing elements, the polypyrimidine tract, or the 5' splice site of intron 20. ISIS 414167 and ISIS 414168, which target an intronic splicing enhancer (designated herein as ISE-20), also significantly decreased the levels of the included RNA isoform compared to the untreated control. The results from the three sets of control oligonucleotide-treated cells were combined and the average is presented in Table 1, designated as 'control oligonucleotide'. 'n/a' indicates 'not applicable. 'n.d.' indicates that there is no data for that particular oligonucleotide.

TABLE 1

Uniform MOE antisense oligonucleotides targeting introns 19 and 20 and exon 20 of SEQ ID NO: 1

| Construct | ISIS No | Sequence | Start Site | Stop Site | Target Region | % inclusion | SEQ ID NO |
|---|---|---|---|---|---|---|---|
| mt19-21 | 414129 | AGAGAATTACCACAA | 34622 | 34636 | intron 19 | 23 | 8 |
| | 414130 | TTCACAGAGAATTAC | 34627 | 34641 | intron 19 | 25 | 9 |
| | 414131 | AACTCTTCACAGAGA | 34632 | 34646 | intron 19 | 30 | 10 |
| | 414132 | TACCTAACTCTTCAC | 34637 | 34651 | intron 19 | 19 | 11 |
| | 414133 | CATTTTACCTAACTC | 34642 | 34656 | intron 19 | 25 | 12 |
| | 414134 | TACACCATTTTACCT | 34647 | 34661 | intron 19 | 25 | 13 |
| | 414135 | CAGGATACACCATTT | 34652 | 34666 | intron 19 | 46 | 14 |
| | 414136 | ATAGCCAGGATACAC | 34657 | 34671 | intron 19 | 45 | 15 |
| | 414137 | TTTAAATAGCCAGGA | 34662 | 34676 | intron 19 | 52 | 16 |
| | 414138 | AAACATTTAAATAGC | 34667 | 34681 | intron 19 | 23 | 17 |
| | 414139 | GTAGAAACATTTAA | 34672 | 34686 | intron 19 | 20 | 18 |
| | 414140 | ATTAAGTAGAAAACA | 34677 | 34691 | intron 19 | 13 | 19 |
| | 414141 | TTTTAATTAAGTAGA | 34682 | 34696 | intron 19 | 24 | 20 |
| | 414142 | AACATTTTAATTAA | 34687 | 34701 | intron 19 | 23 | 21 |
| | 414143 | GCAGTAACATTTTTA | 34692 | 34706 | intron 19 | 8 | 22 |
| | 414144 | TTAAAGCAGTAACAT | 34697 | 34711 | intron 19 | 7 | 23 |
| | 414145 | ATAAATTAAAGCAGT | 34702 | 34716 | intron 19 | 3 | 24 |
| | 414146 | CTTAAATAAATTAAA | 34707 | 34721 | intron 19 | 26 | 25 |
| | 414147 | GTTTCCCCTTGGCAT | 34722 | 34736 | exon 20 | 3 | 26 |
| | 414148 | TCTAAGTTTCCCCTT | 34727 | 34741 | exon 20 | 7 | 27 |
| | 414149 | CAACTTCTAAGTTTC | 34732 | 34746 | exon 20 | 20 | 28 |
| | 414150 | ATGAACAACTTCTAA | 34737 | 34751 | exon 20 | 5 | 29 |
| | 414151 | CGATGATGAACAACT | 34742 | 34756 | exon 20 | 0 | 30 |
| | 414152 | GGGCTCGATGATGAA | 34747 | 34761 | exon 20 | 3 | 31 |
| | 414153 | AACCAGGGCTCGATG | 34752 | 34766 | exon 20 | 5 | 32 |
| | 414154 | GCTAAAACCAGGGCT | 34757 | 34771 | exon 20 | n.d. | 33 |
| | 414155 | TCTGAGCTAAAACCA | 34762 | 34776 | exon 20 | 6 | 34 |
| | 414156 | CCGAATCTGAGCTAA | 34767 | 34781 | exon 20 | 5 | 35 |
| | 414157 | CACTTCCGAATCTGA | 34772 | 34786 | exon 20 | 15 | 36 |
| | 414158 | CCAACCACTTCCGAA | 34777 | 34791 | exon 20 | 1 | 37 |
| | 414159 | TTGTCCAACCACTTC | 34781 | 34795 | exon 20 | 2 | 38 |
| | 414160 | TACAATGGCGCTTAC | 34796 | 34810 | intron 20 | 14 | 39 |
| | 414161 | AACAGTACAATGGCG | 34801 | 34815 | intron 20 | 88 | 40 |
| | 414162 | TCGCAAACAGTACAA | 34806 | 34820 | intron 20 | 79 | 41 |
| | 414163 | ACTAGTCGCAAACAG | 34811 | 34825 | intron 20 | 74 | 42 |
| | 414164 | AGCTAACTAGTCGCA | 34816 | 34830 | intron 20 | 78 | 43 |
| | 414165 | TCACAAGCTAACTAG | 34821 | 34835 | intron 20 | 66 | 44 |

TABLE 1-continued

Uniform MOE antisense oligonucleotides targeting introns 19 and 20 and exon 20 of SEQ ID NO: 1

| Construct | ISIS No | Sequence | Start Site | Stop Site | Target Region | % inclusion | SEQ ID NO |
|---|---|---|---|---|---|---|---|
| | 414166 | ATAAATCACAAGCTA | 34826 | 34840 | intron 20 | 40 | 45 |
| | 414167 | CACACATAAATCACA | 34831 | 34845 | intron 20 | 13 | 46 |
| | 414168 | GTCTTCACACATAAA | 34836 | 34850 | intron 20 | 17 | 47 |
| | 414169 | TTATTGTCTTCACAC | 34841 | 34855 | intron 20 | 21 | 48 |
| | 414170 | AATACTTATTGTCTT | 34846 | 34860 | intron 20 | 32 | 49 |
| | 414171 | AATAAAATACTTATT | 34851 | 34865 | intron 20 | 32 | 50 |
| | 414172 | ATTGTAATAAAATAC | 34856 | 34870 | intron 20 | 31 | 51 |
| | 414173 | TCGAAATTGTAATAA | 34861 | 34875 | intron 20 | 31 | 52 |
| | 414174 | AGTTCTCGAAATTGT | 34866 | 34880 | intron 20 | 29 | 53 |
| | 414175 | TTTTAAGTTCTCGAA | 34871 | 34885 | intron 20 | 27 | 54 |
| | 414176 | CATAATTTTAAGTTC | 34876 | 34890 | intron 20 | 31 | 55 |
| | 414177 | CTTTTCATAATTTTA | 34881 | 34895 | intron 20 | 25 | 56 |
| wt19-21 | n/a | n/a | n/a | n/a | n/a | 99 | |
| Untreated mt19-21 | n/a | n/a | n/a | n/a | n/a | 29 | |
| mt19-21 | Control oligos | 383548 TTTATATGGATGTTAAAAAG | n/a | n/a | n/a | 24 | 57 |
| | | 383553 AAAAGCATTTTGTTTCACAA | | | | | 58 |
| | | 383874 ATTTTGTCTGAAACC | | | | | 59 |

Skipping of exon 20 causes a frameshift that introduces a premature termination codon (PTC) in exon 21, thereby making the mRNA potentially susceptible to degradation according to the characterized rules of the nonsense-mediated mRNA decay (NMD) pathway (Nagy, E., and Maquat, L. E. 1998. *Trends Biochem Sci* 23:198-199). A similar experiment to the one described above was conducted utilizing the wt19-22 and the mt19-22 minigenes to determine if the NMD pathway controls the stability of the skipped mRNA isoform. The same pattern of inclusion or skipping of exon 20 was observed with the wt19-22 and mt19-22 minigenes as observed with the corresponding 19-21 minigenes. Therefore, there is no evidence that the skipped mRNA isoform resulting from mt19-22 minigene was subject to NMD.

Figure 3A:
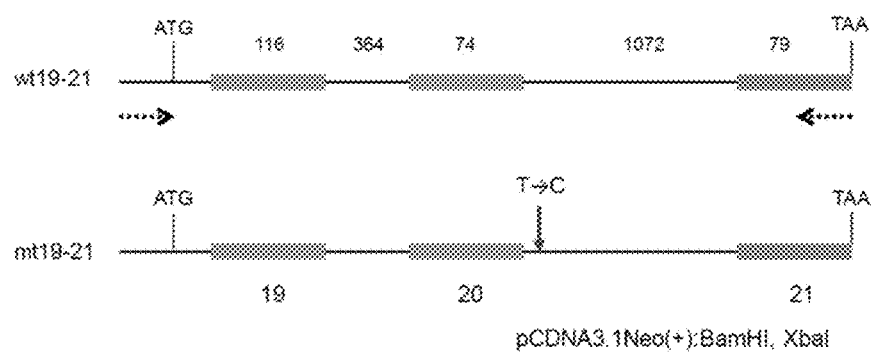
FIGS. 3A-B. These figures illustrate minigene constructs.
Figure 3B:
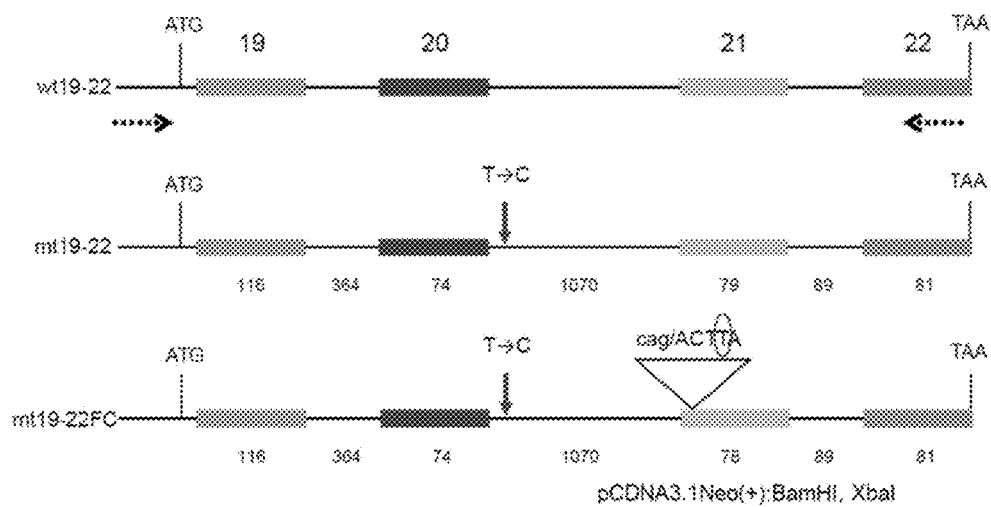
Figure 4A:
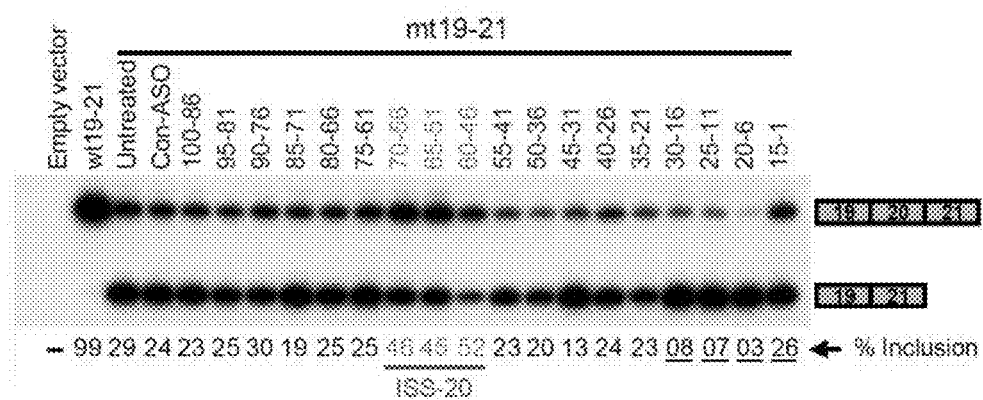
FIGS. 4A-D. These figures illustrate microwalks of antisense oligonucleotide compounds on different regions of an IKBKAP gene.
Figure 4B:
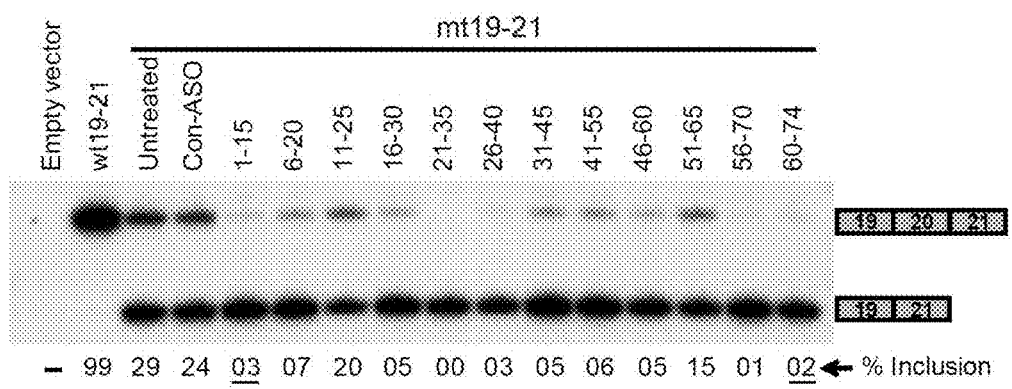
Figure 4C:
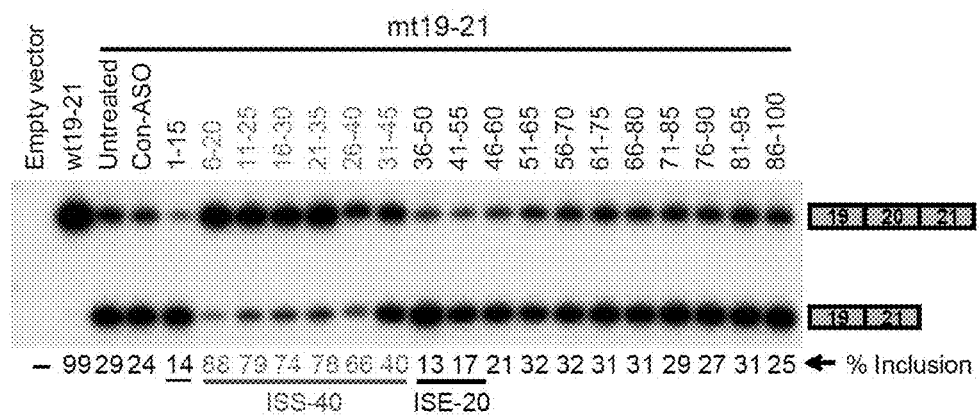
Figure 4D:
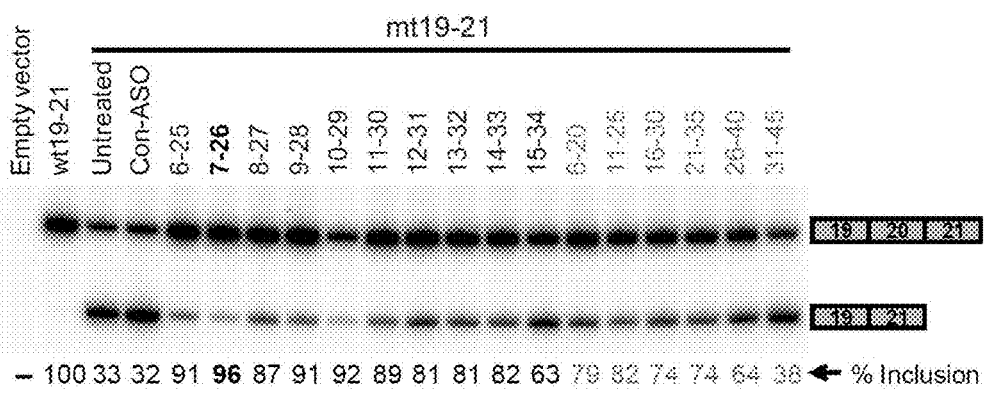
Figure 5:
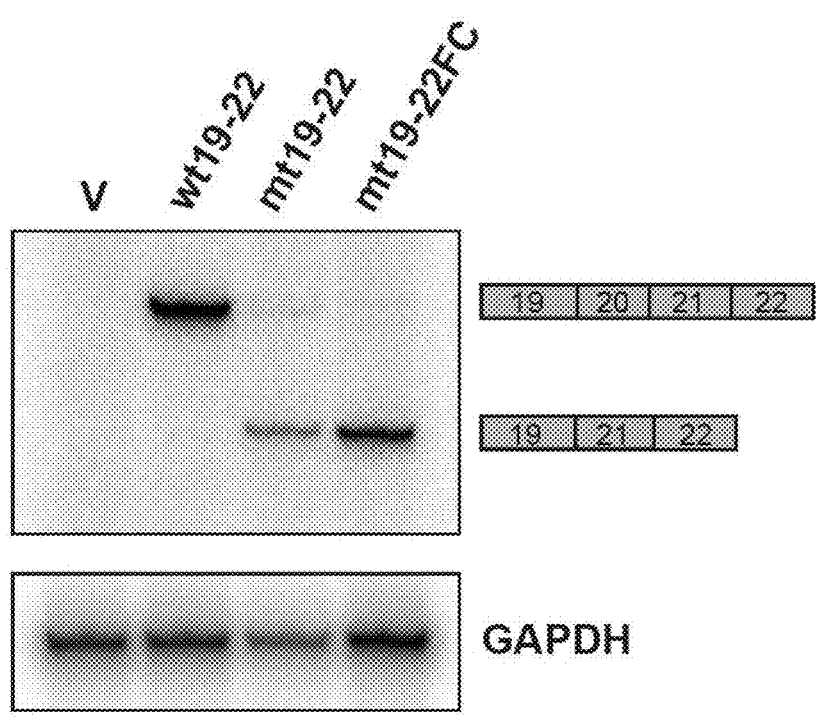
FIG. 5. This figure illustrates the stability of skipped mRNAs with or without the premature termination codon using RT-PCR.

To confirm this finding, a single nucleotide in exon 21 of the mt19-22 minigene was deleted to restore the reading frame and remove the premature termination codon (PTC). This minigene was designated as mt19-22FC minigene (FIG. 3). The three minigenes, wt19-22, mt19-22 and mt19-22FC, were individually transfected into HEK-293 cells using the same protocol as described above. The expressed RNA was analyzed by RT-PCR. Consistent with the observation made in the study with antisense oligonucleotide transfection described above, the skipped mRNAs with or without the PTC were equally stable (FIG. 5). This confirms that at least in HEK-293 cells, the skipped mRNA isoform is not subject to NMD.

Example 3: Effect of Oligonucleotides Designed by Microwalk on Exon Skipping in the IKBKAP Minigenes Additional oligonucleotides were designed targeting the first 30-nucleotide stretch of ISS-40. These oligonucleotides were designed by choosing sequences shifted in one nucleotide increments upstream and downstream (i.e., a "microwalk") of ISS-40, starting from the +6 position in exon 20. The antisense oligonucleotides are presented in Table 2 and FIG. 4D, and were designed as uniform 2'-O-methoxyethyl ribose (MOE) oligonucleotides with phosphate backbones. Each oligonucleotide is 20 nucleosides in length. All cytosine residues throughout the oligonucleotide are 5-methylcytosines. 'Start Site' indicates the 5'-most nucleoside to which the oligonucleotide is targeted in the human gene sequence. "Stop site" indicates the 3'-most nucleoside to which the oligonucleotide is targeted in the human gene sequence. Each oligonucleotide listed in Table 2 is targeted to intron 20 of the human IKBKAP genomic sequence (the complement of GENBANK Accession No NT_008470.16 truncated from nucleotides 13290828 to Ser. No. 13/358,424, designated herein as SEQ ID NO: 1). These oligonucleotides were tested in vitro. ISIS 414161, ISIS 414162, ISIS 414163, ISIS 414163, ISIS 414164, ISIS 414165, and ISIS 414166, which showed a high percentage of inclusion, were also included in the assay.

Cultured HEK-293 cells harboring the mt19-21 minigene vector construct at a density of $7 \times 10^5$ cells per well were transfected using electroporation (Gene Pulsar II apparatus, Bio-Rad) with 0.007 nmol antisense oligonucleotide, as previously described (Hua, Y., et al., 2007. *PLoS Biol* 5:e73).

Control oligonucleotides that do not cause any exon skipping were similarly transfected and served as controls for non-specific effects of uniform MOE oligonucleotides with phosphate backbones. Cells harboring the wt19-21 minigene and the mt19-21 minigene alone were also cultured and were used as controls for exon 20 inclusion levels. Two days later, cDNA synthesized from total RNA extracted from HEK-293 cells was amplified using the forward primer pCDNAF and reverse primer sequence IKAP21R4 to assay the splicing pattern of expressed RNAs by RT-PCR. To calculate exon 20 inclusion levels, the PCR amplicons were labeled with $\alpha^{32}$P-dCTP. The PCR products were then separated by native PAGE, followed by phosphorimage analysis. The band intensities were quantified and values were normalized for the G+C content according to the DNA sequence. The results are presented in Table 2. It was observed that treatment of the cells with ISIS 421992 restored exon 20 inclusion levels to 96% in the mutant minigene. It was also observed that the 20-mer antisense oligonucleotides have a stronger positive effect on exon 20 splicing than the 15-mer antisense oligonucleotides targeting the same region.

reverse primer sequence IKAP21R4 to assay the splicing pattern of expressed RNAs by RT-PCR. To calculate exon 20 inclusion levels, the PCR amplicons were labeled with $\alpha^{32}$P-dCTP. The PCR products were then separated by native PAGE, followed by phosphorimage analysis. The band intensities were quantified and values were normalized for the G+C content according to the DNA sequence. The results are presented in Table 3 and FIG. 1. Multiple lanes for each condition represent independent experiments.

Treatment with ISIS 421992 almost completely suppressed the splicing defect, as demonstrated by the percent inclusion of exon 20 in Table 3 and the left panel of FIG. 1A. Kinetin (6-furfurylaminopurine) has been shown to improve splicing and increase wild-type IKBKAP mRNA and IKAP protein expression in FD cell lines (Hims, M. M. et al., 2007. *J. Mol. Med.* 85: 149-161). Treatment with ISIS 421992 was as effective as treatment with kinetin for 3 days in restoring full-length mRNA levels (FIG. 1A, right panel). A batch of cells was treated with solvent (NaOH) only of the kinetin solution as a control. RNA from IMR90, a wild-type normal diploid lung fibroblast cell line was used as positive control.

TABLE 2

Uniform MOE antisense oligonucleotides targeting intron 20 of SEQ ID NO: 1

| Construct | ISIS No | Sequence | Start Site | Stop Site | % inclusion | SEQ ID NO |
|---|---|---|---|---|---|---|
| mt19-21 | 414161 | AACAGTACAATGGCG | 34801 | 34815 | 79 | 40 |
|  | 414162 | TCGCAAACAGTACAA | 34806 | 34820 | 82 | 41 |
|  | 414163 | ACTAGTCGCAAACAG | 34811 | 34825 | 74 | 42 |
|  | 414164 | AGCTAACTAGTCGCA | 34816 | 34830 | 74 | 43 |
|  | 414165 | TCACAAGCTAACTAG | 34821 | 34835 | 64 | 44 |
|  | 414166 | ATAAATCACAAGCTA | 34826 | 34840 | 38 | 45 |
|  | 421991 | TCGCAAACAGTACAATGGCG | 34801 | 34820 | 91 | 60 |
|  | 421992 | GTCGCAAACAGTACAATGGC | 34802 | 34821 | 96 | 61 |
|  | 421993 | AGTCGCAAACAGTACAATGG | 34803 | 34822 | 87 | 62 |
|  | 421994 | TAGTCGCAAACAGTACAATG | 34804 | 34823 | 91 | 63 |
|  | 421995 | CTAGTCGCAAACAGTACAAT | 34805 | 34824 | 92 | 64 |
|  | 421996 | ACTAGTCGCAAACAGTACAA | 34806 | 34825 | 89 | 65 |
|  | 421997 | AACTAGTCGCAAACAGTACA | 34807 | 34826 | 81 | 66 |
|  | 421998 | TAACTAGTCGCAAACAGTAC | 34808 | 34827 | 81 | 67 |
|  | 421999 | CTAACTAGTCGCAAACAGTA | 34809 | 34828 | 82 | 68 |
|  | 422000 | GCTAACTAGTCGCAAACAGT | 34810 | 34829 | 63 | 69 |
| wt19-21 | n/a | n/a | n/a | n/a | 100 | n/a |
| Untreated mt19-21 | n/a | n/a | n/a | n/a | 33 | n/a |
| mt19-21 | Control oligos | TTTATATGGATGTTAAAAAG | n/a | n/a | 32 | 57 |
|  |  | AAAAGCATTTTGTTTCACAA |  |  |  | 58 |
|  |  | ATTTTGTCTGAAACC |  |  |  | 59 |

Example 4: Effect of ISIS 421992 in FD-Derived Fibroblasts

To investigate the effect of ISIS 421992 on patient-derived fibroblasts, the patient skin fibroblast line GM04899 (Coriell Cell Repository) was utilized. The cell line was derived from an individual homozygous for the major FD mutation.

GM04899 was cultured in minimal essential medium (Invitrogen) supplemented with non-essential amino acids (Invitrogen) and 20% (v/v) fetal bovine serum. The cells were grown to 40-50% confluence in 10-cm dishes. Cells were transfected with 2 nM, 5 nM, 25 nM, or 125 nM concentrations of ISIS 421992 using 12 µL Lipofectamine 2000 transfection reagent (Invitrogen). Two days later, cDNA synthesized from total RNA extracted from HEK-293 cells was amplified using the forward primer pCDNAF and The results are expressed as percent inclusion of exon 20 compared to the exon 20 inclusion (100%) of KBKAP mRNA in IMR90 cells.

Treatment with ISIS 421992 at 5 nM also resulted in a significant increase in IKAP protein levels, when assayed 3 days after transfection. Protein samples were obtained by Trizol extraction and separated by SDS-PAGE. The bands were transferred onto a nitrocellulose membrane and probed with an anti-IKAP antibody (abcam # ab56362) (1:1,000 dilution in 5% milk in TBST) for 12 hrs. The membrane was washed 5 times with TBST for 5 min each and then probed with secondary antibody 800 nm LiCor (1:5,000 in 5% milk in TBST) for 1 hr in the dark. The membrane was subsequently washed 5 times with TBST for 5 min each. The bands were then exposed at 800 nm and band intensity was quantified using an Odyssey (LiCor) instrument. The results are presented in Table 4 as percent increase in band intensity compared to the control oligonucleotide-treated bands. The data indicate that treatment with ISIS 421992 significantly increased IKAP protein levels compared to the control. Note that under these conditions, kinetin did not increase IKAP protein levels.

TABLE 3

Exon 20 inclusion after treatment of GM04899 with ISIS 421992

| | % inclusion |
|---|---|
| Untreated | 69 |
| Control oligo treated | 67 |
| ISIS 421992 2 nM | 79 |
| ISIS 421992 5 nM | 95 |
| ISIS 421992 25 nM | 96 |
| ISIS 421992 125 nM | 97 |
| solvent-treated | 67 |
| kinetin-treated | 98 |

TABLE 4

Percent incease in protein band intensity after treatment of GM04899 with ISIS 421992

| | % |
|---|---|
| ISIS 421992 2 nM | 76 |
| solvent-treated | 10 |
| kinetin-treated | 11 |

Example 5: Effect of ISIS 421992 in a Transgenic Mouse Model

To investigate the effect of ISIS 421992 in an animal model, transgenic mice that carry the entire human IKBKAP gene with the major FD mutation, in addition to being homozygous wild type at the mouse Ikbkap locus, were obtained from an NIH core facility. Though the transgenic mice do not show any overt disease phenotype, due to the presence of the wild-type mouse Ikbkap gene, the mRNA expressed by the mutant human IKBKAP transgene does show a pattern of skipping similar to that of FD patients (Hims, M. M. et al., 2007. Genomics. 90: 389-396).

Figure 2A:
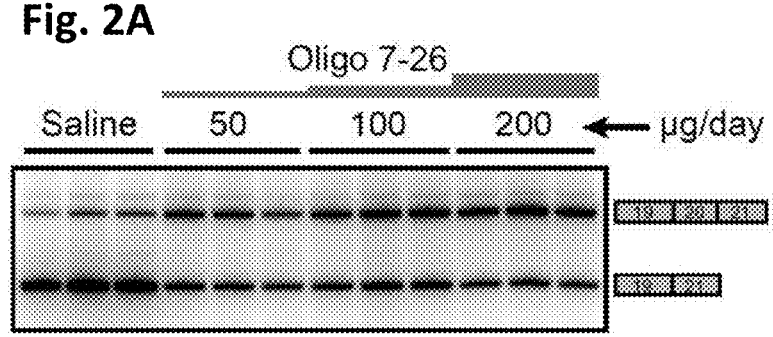
FIGS. 2A-F.

Adult mice were treated with ISIS 421992 administered by intracerebroventricular infusion at the rate of 50 µg/day, 100 µg/day, or 200 µg/day. The protocol has been previously described by Hua et al. (Genes Dev. 2010. 24: 1634-1644). Adult mice 3-4 months old and weighing 20-30 g, were anesthetized and placed on a digital stereotaxic instrument (David Kopf Instruments). A small burr hole at the surgical site 1.8 mm lateral to the sagittal suture and 0.3 mm posterior to the bregma suture was drilled through the skull above the right lateral ventricle. A cannula with a 2.2 mm stylet was positioned in the hole. The cannula was connected to an Alzet micro-osmotic pump (model 1007D, Durect Corporation) with a vinyl catheter. The pump, prefilled with the oligonucleotide solution or PBS only was implanted subcutaneously on the back and continuously infused the solution through the cannula into the lateral ventricle at a rate of 0.5 µL per hour. After a week of ICV infusion, the mice were euthanized on day 8 and RNA from the thoracic spinal cord of the transgenic mice was extracted using Trizol and following the manufacturer's protocol. Human IKBKAP mRNA levels were measured and the results are presented in Table 5 and FIG. 2A. Multiple lanes for each condition represent independent experiments. The data indicate that there was a dose-dependent increase in the inclusion of exon 20 in human IKBKAP mRNA levels in these mice.

TABLE 5

Percent inclusion of exon 20 in human IKBKAP mRNA levels in transgenic mice

| Treatment | Dose (µg/day) | % |
|---|---|---|
| PBS | — | 6 |
| ISIS 421992 | 50 | 40 |
| | 100 | 46 |
| | 200 | 60 |

Figure 2B:
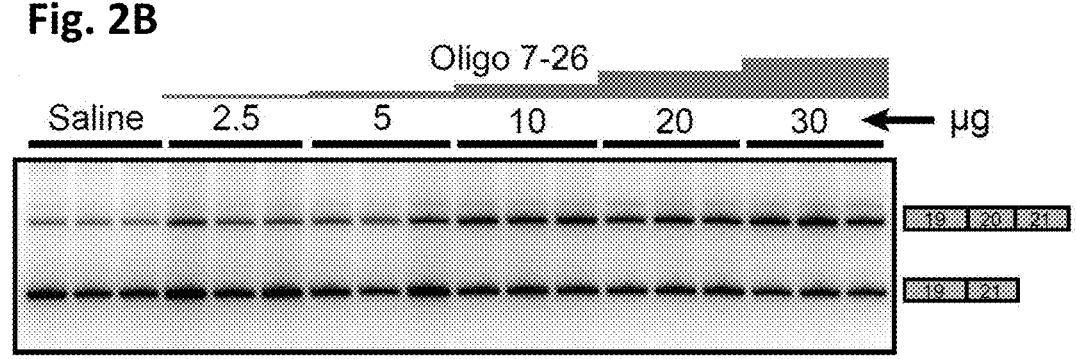
Figure 2C:
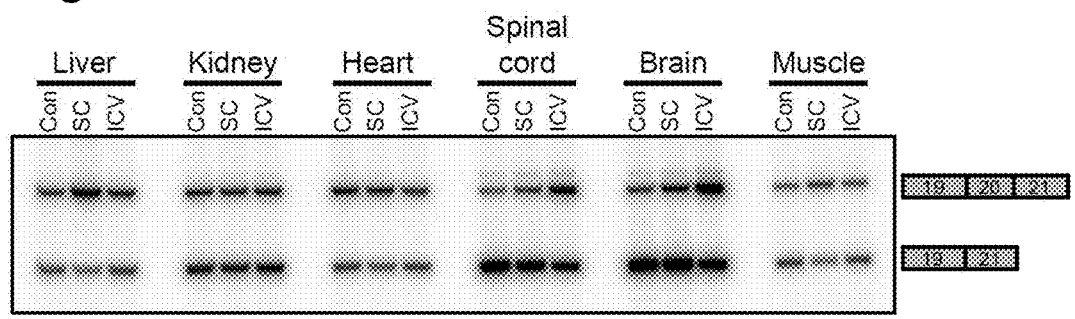
Figure 2D:
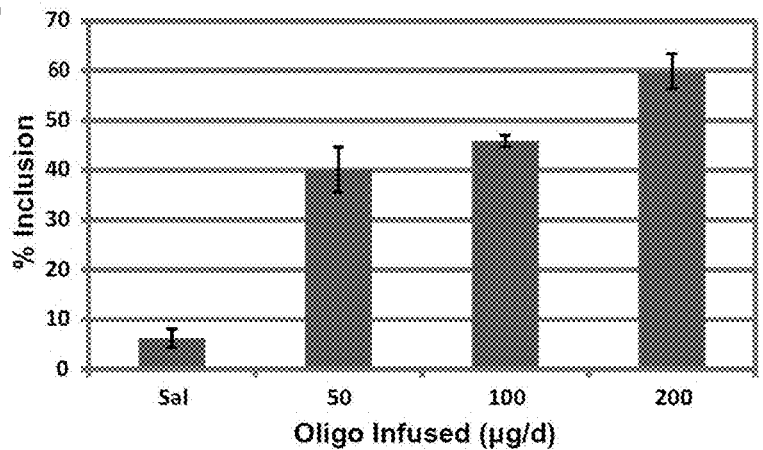
Figure 2E:
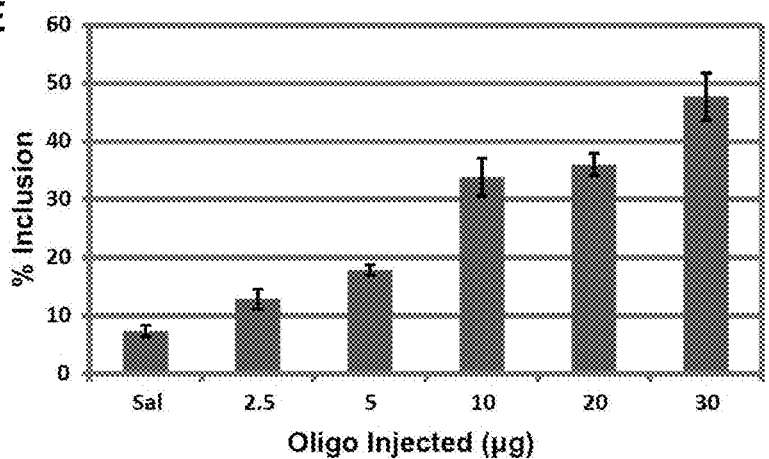
Figure 2F:
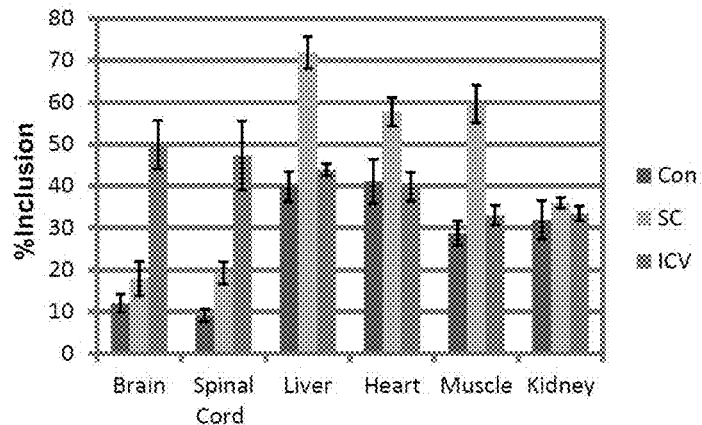

Neonatal transgenic mice were also treated with ISIS 421992 administered as a single ICV injection dose of 2.5 µg, 5 µg, 10 µg, 20 µg, or 30 µg. A group of neonatal mice were treated with ISIS 421992 administered subcutaneously using a 10 µL micro syringe (Hamilton) and a 33-gauge needle. In all cases, the injections were administered at P1 and the RNA was assayed at P8. The RNA splicing patterns in the various tissues after administering ISIS 421992 in neonate mice were then observed. The results of the ICV administration are presented in FIG. 2B and Table 6. Multiple lanes for each condition represent independent experiments. ICV administration primarily resulted in increased full-length IKBKAP mRNA in the brain and spinal cord, with moderate effects in the peripheral tissues, whereas subcutaneous administration primarily affected expression in the liver, skeletal muscle, and heart with moderate effects in the CNS (FIG. 2C, 2F, and Table 7). The plot shows inclusion percentages of IKBKAP exon 20 in different tissues from five independent ICV or subcutaneous injections.

TABLE 6

Percent inclusion of exon 20 in human IKBKAP mRNA levels after ICV administration to neonatal Tg mice

| Treatment | Dose (µg) | % |
|---|---|---|
| PBS | — | 7 |
| ISIS 421992 | 2.5 | 13 |
| | 5 | 18 |
| | 10 | 34 |
| | 20 | 36 |
| | 30 | 48 |

TABLE 7

Percent inclusion of exon 20 in human IKBKAP mRNA levels in different tissues of neonatal Tg mice

| | Control | s.c. injection | ICV administration |
|---|---|---|---|
| Brain | 12 | 18 | 50 |
| Spinal Cord | 9 | 19 | 47 |
| Liver | 40 | 72 | 44 |
| Heart | 41 | 58 | 40 |
| Muscle | 29 | 60 | 33 |
| Kidney | 32 | 36 | 33 |

We claim:

1. A compound comprising a modified oligonucleotide consisting of linked nucleosides having an entire nucleobase sequence selected from SEQ ID NOS: 40, 41, 42, 43, 44, 60, 61, 63, 64, 65, 66, 67, and 68.

2. The compound of claim 1, wherein the modified oligonucleotide comprises at least one modified nucleoside.

3. The compound of claim 2, wherein at least one modified nucleoside comprises a modified sugar moiety.

4. The compound of claim 3, wherein at least one modified sugar moiety is a 2'-substituted sugar moiety.

5. The compound of claim 4, wherein the 2'-substitutent of at least one 2'-substituted sugar moiety is selected from the group consisting of 2'-OMe, 2'-F, and 2'-MOE.

6. The compound of claim 5, wherein the 2'-substituent of at least one 2'-substituted sugar moiety is a 2'-MOE.

7. The compound of claim 3, wherein at least one modified sugar moiety is a bicyclic sugar moiety.

8. The compound of claim 7, wherein at least one bicyclic sugar moiety is LNA or cEt.

9. The compound of claim 1, wherein at least one sugar moiety is a sugar surrogate.

10. The compound of claim 9, wherein at least one sugar surrogate is a morpholino.

11. The compound of claim 9, wherein at least one sugar surrogate is a modified morpholino.

12. The compound of claim 1, wherein each nucleoside of the modified oligonucleotide is a modified nucleoside, each independently comprising a modified sugar moiety.

13. The compound of claim 1, wherein the modified oligonucleotide comprises at least two modified nucleosides comprising modified sugar moieties that are the same as one another.

14. The compound of claim 1, wherein the modified oligonucleotide comprises at least two modified nucleosides comprising modified sugar moieties that are different from one another.

15. The compound of claim 1, wherein each nucleoside of the modified oligonucleotide is a modified nucleoside.

16. The compound of claim 1, wherein each nucleoside of the modified oligonucleotide is a modified nucleoside, and each modified nucleoside comprises the same modification.

17. The compound of claim 16, wherein the modified nucleosides each comprise the same 2'-substituted sugar moiety.

18. The compound of claim 17, wherein the 2'-substituted sugar moiety is selected from 2'-F, 2'-OMe, and 2'-MOE.

19. The compound of claim 18, wherein the 2'-substituted sugar moiety is 2'-MOE.

20. A method of modulating splicing in an IKBKAP transcript in a cell comprising contacting the cell with a compound comprising a modified oligonucleotide consisting of 15 to 22 linked nucleosides having a nucleobase sequence comprising an at least 15 nucleobase portion of a sequence selected from SEQ ID NOS: 40, 41, 42, 43, 44, 60, 61, 62, 63, 64, 65, 66, 67, and 68, and wherein splicing induces or enhances inclusion of exon 20.

* * * * *

SEQUENCE LISTING

<160> NUMBER OF SEQ ID NOS: 69

<210> SEQ ID NO 1
<211> LENGTH: 67597
<212> TYPE: DNA
<213> ORGANISM: Homo sapiens

<400> SEQUENCE: 1

| | | | | | |
|---|---|---|---|---|---|
| cagcattagg | ccagtgcggc | caaggaggga | tcaacatcac | tccgcactta | cccggtttgt | 60 |
| accagcgagt | gaagtatcga | tccacgagcg | aaggcaccac | cggctccgcg | gcttcgggct | 120 |
| cggtagccat | ggcgacctcc | ggcgccgcca | ccccgccct | ccgggacccc | agcgcttcct | 180 |
| ccgcgcagcc | cggactgggc | gtgctcttcc | ggcgcacagc | gcgtgtcgtg | cgcacgcgcg | 240 |
| ctgctctcag | gtccgcaggt | tccaccccc | cccgccc | cccaattac | agtgctttgg | 300 |
| ggttcgacat | caaaacagag | atcaaataca | aaagtttggg | cagatgggca | agagggcaga | 360 |
| gggacagggg | acgcggccaa | tgtagctcct | ctacctctac | ggtgccaggc | ctacaaagaa | 420 |
| ggccggccgc | cgtaagtgac | cagaagcggg | cccggcctcg | cccctccgc | ctggtgacgt | 480 |
| cactcccgcg | ccgcactccc | agtgctgcgg | ctgcctagtt | gacgcaccca | ttgagtcgct | 540 |
| ggcttctttg | cagcgcttca | gcgttttccc | ctggagggcg | cctccatcct | tggaggccta | 600 |
| gtgccgtcgg | agagagagcg | ggagccgcgg | acagagacgc | gtgcgcaatt | cggagccgac | 660 |
| tctgggtgcg | gactgtggga | gctgactctg | ggtagccggc | tgcgcgtggc | tggggaggcg | 720 |
| aggccggacg | cacctctgtt | tggggtcct | caggtaagcg | atccatccag | ggtaggggca | 780 |
| cgggagtgga | cctctccgcc | ggcggtgtcc | gggtgaagga | gacccggagc | ctcctctgcc | 840 |
| tgctgcgggc | cggggactgg | agtgcgggct | gcaccacctc | tttcctagag | ccttaaattc | 900 |
| tttttgcagc | cttgccacct | gctccatcgg | gggcgctggg | aggcgcgaca | gcccagggat | 960 |
| gcctgctgcc | cctccagccg | gacttaaccc | agcctcttga | ttgcttgcag | ggggttgata | 1020 |
| ataacgctga | aagcgagagt | attaattcac | gatggaaggc | ggcggttaat | agaggctcgg | 1080 |
| gtgctgtggt | gcgggtcctt | tctcgcgtgt | gagactttt | cgtggaggtg | gtgtcctctg | 1140 |
| tgcttctcca | tctaacgtgg | tgttttacgt | ggctttctct | cccgttaacg | atgatctccg | 1200 |
| tggagacagt | ggctgagtaa | tcttcagatc | ccagtactta | gcaagtgctc | agtcggtgtt | 1260 |
| ggatgtaggc | cacaaaccgg | atcgtaaaga | attcaactgt | atattgacag | ccacggaact | 1320 |
| aatcaatgaa | tagatccgta | tgaagagtaa | gcaaaaaggc | agcaaagaca | gttttttcagc | 1380 |
| ttggggacat | agagtagaaa | tggtctgtcc | ccaaatagtg | ggaactgtca | tttgggggaa | 1440 |
| gaatagcaag | ttcttttgctt | tccaggtcgc | atttgatgtg | catgtgagac | atgcttgtga | 1500 |
| ttctatcagg | aggttgaaaa | tgtgggttta | gtggtaagtt | tgggctaatt | cagtcagggc | 1560 |
| taggcattta | ggcctaatca | gcgtattggt | gatctacctg | gtatatgtaa | tcatgcatgt | 1620 |
| gatgtctagc | caagaggtgg | atagtcgaag | gagcaaggga | agaaaatgaa | gcagttatca | 1680 |
| ggaaattaag | agagaatcca | cgattgacct | ttggtgtgga | gggatcttta | gcacatttaa | 1740 |
| gaactgcgaa | gagtttgaat | cagtggaggc | aggaaggttg | gaggttgcag | atgtccaaga | 1800 |
| aagagtacta | ataggcctag | gtcctgtggc | aatatggagg | atattccttt | cctagcctgg | 1860 |
| aaagaagtgg | agggaagtct | tcctccgaga | agataaggga | ataaggctga | tgggtgtgaa | 1920 |
| atttcagaga | aactagtttt | gaggcgtttt | tatgatgttt | aaagatgaaa | aacgcagcca | 1980 |
| ggcacgtgtg | ctcaggcctg | taatcccagc | actttgggag | gcagaggcgg | gtggatcact | 2040 |
| tgaggttagg | agttcaagaa | cagcctggcc | aacatggtga | aaccctgtct | ctactaaaaa | 2100 |

```
tacaaaaatt aactgggcat ggtgccgggc gcctgtaatc ccagctactc ggaggctga    2160 ggcaggagaa tcgcttgaac ccgggaggca gatgttgcgg tgagccgaga tcgcgccatt    2220 gcacccagc ctgggcaata agagcgaaac tccgtctcaa aaacaaaaa aacctgcatg    2280 atatgttaga ggttcaagta atttctagca gttcttgaat ataattgtca ccaaaactta    2340
ctaaaatcat tgtcttcctc acttccatca tatataaact tacctttctc ttatcccaca    2400
ttatatatta tataattcct atgacacttg acattatctt ctgtgtacta ttaggattga    2460
ttcatcttta ttctttctat gtcatacata tgtggggtgc caagatgaga gaagtctcct    2520
tggattaaag tgacaataag accggtgtgg tccttgtaat tgctacccct aacataagtt    2580
agggacttac aatcataagc cttaaaggga tctgaatata ataactagc acagtaacat    2640 tttttttcccc tacttaggta atgttatgca tttaagcaag cctgattttg ccagaccaaa    2700
gtagatgtct tgtttagcac tcttttctca cgttttatat tgtcctggga aaagcctggc    2760
cagaagaaca aagttactgg aagtagttat gtcaggtcat cagggtcctt gaaatgttgg    2820
tcatcatttt gaagtaaatt gttgtcatgt cccagtatt tctcttcccc tttagaacag    2880
taaatgcttt tctatctttg atttcagttt ttttatgaat gtataaaacc agtttataaa    2940
tgaatagacc tggtgaatat taaagtcatt tcagattctc ttcaactgcc agtatataaa    3000
aatggatttt caaatagtgc taatcagtgg gatacccttt tgttttttcct catgattta    3060 taaagatgtc ctaatatgca aaaataaaat gtttccccat tcatttgttc tttcaacttt    3120
cccaaaggaa taactgatat tacatctttt ttgaagaaaa cattctaaag ttgagaatct    3180
tgcctctcct aaaaagaaca taaaataggt ttcagaattc ctaattgta gaccataact    3240 gtatagagtg ggtcaggttg ctgctataat ccatacatgg gtgtgtactc agagaggtaa    3300
gttttttctt ttcttggtta ttctgattct gactaccact tcttcacccc ctgaatcatt    3360
tcattttaaa aaatatggtc atttatcact attaagctat ttattttct cttagagatt    3420 aatgattcat caagggatag ttgtacttgt ctcgtgggaa tcacttcatc atgcgaaatc    3480
tgaaattatt tcggaccctg gagttcaggg atattcaagg tccagggaat cctcagtgct    3540
tctctctccg aactgaacag gggacggtgc tcattggttc agaacatggc ctgatagaag    3600
tagaccctgt ctcaagagaa gtaagttact gatgtagaat gccagcatgt gggtatgacc    3660 cttgattct cttcttccaa atttctttcc ccacatggtc tttctttata tcttattgaa    3720
tttatatcct cccaaataaa catcttttgc ttcatatata tgccatgtta gacatagctt    3780 aaaatcgtaat ccttctttaa ctctgctgct attttaacct aagtcagtag aactctgacc    3840
ttactttttg agtgtgtgcc gtactttta ccctctttgt catgcaaatt ctgtttataa    3900
gagtggtttt ttttttttt ttttttgaga cggagtctcg ctctgtcacc caggctggag    3960
tgcagtggtg tgatcgtggc tcactgcaag ctccgcctcc ccgggttcac accattctcc    4020
tgcctcagcc tcccgagaag ctgggactac aggcgcccgc caccgcgccc ggctaatttt    4080
ttgtattttt agtagatgtg cggtttcacc gtgttagcca ggatggtctt gatctcctga    4140
cctcgtgatc cgcctgcctc agcgcccggc caagagtggt ttttaattgg gaatgaacac    4200
gaaagttgcc catggagctt tctaaaagtt tgagcccaca tctcatgtca actaaatcag    4260
aatctttagt gttggctcct aactatatgt actttaaaaa cctctgtggg ttggttttga    4320 tatggtcccct tgattatgtt cttctactaa tacattttag gcagttacat cctttagtgc    4380
cttttcccca tactatagaa atcttagaaa agcatagcta ttagcatcat attttagtgg    4440
```

```
acaattttaa agagaccagg cttattgttt ttgttttttgt gtttgtttgg caaaaaggtc   4500
acattaccta tttttcttgt tagagatgac agagtagtga tatttctcaa atgaaagttt   4560
ggattttcat ctagaaaaaa tattttttgaa agcttttatg taataaaaga agcattaaaa  4620
agtatttctg gaaatgttat caattattct tgaaagtaga ctgggttaat ttgcttgtgt   4680
ttactttggt gaaaggtgaa aaatgaagtt tctttggtgg cagaaggctt tctcccagag   4740
gatggaagtg gccgcattgt tggtgttcag gacttgctgg atcaggagtc tgtgtgtgtg   4800
gccacagcct ctggagacgt catactctgc agtctcagca cacaacaggt aagtggaaga   4860
ctccagtgag gggggagtct caagcatcct caaataggtt acttgctatt tgtggaagtt   4920
ttcaaatcag tagccataat agttacactt tgctaatta attttttgcat tatatatttc   4980
tttatttaaa aaattgttaa catggcttta tctatatgtt aagattcttc taaaactgag   5040
ttttgtctgc tgcatctatt aatcagagtg atcagaatgt tccaaatgag aatatatttt   5100
tttaaaagtt aaaactggct attcttatgt ggtgtagatc acctcttatc agaccctcat   5160
cttgagttgc aacctttgtt tctcaattta ggaagtcttt gtttatctga cttagatttt   5220
ctgttatgaa tgttgattgg ctaaatttag agtccctgaa gtctaggcac taaagtaaat   5280
acattgtcat tacctgcaca tgtgatgact gccagtagag ctagacttca agcaattgct   5340
tctttctcta ctttagtgta tagttgagtt tctgatttct atcctcacct tcttaacagc   5400
aagggtttca aattacactt ggctgattct ttaaatcttc ttccattact tcattagttg   5460
tgatctcctt aacattgatt atgtcacaga agttagagta ttactaatag taggataatg   5520
atagcagctt acatttatta actatcatgt gcctggcact ttttaaagtg cttttcatgc   5580
aaatttattt aatcttcacc atgaccttat gcagtaggtt gttgtttcct attcttcaga   5640
agaggcagtt aaggcacaga gtgcttaagt aattagacca gggtcacaca gtaatcaaat   5700
ggggtttgac cctagcagtc taaatctggc acctctgctc ttaaccattc catttagtac   5760
aatcataaac cttacttgc agttcatggt gggaaatatc aaacttgtca tatacagctt    5820
gttttttttt cgtatttgaa agatagatgc ttttactttc caaacatttt gtagcattgt   5880
ttcctggtta ctgagctctt ccagtctatt tatcttcatt taatggtgct gattctgccc   5940
tttagtggct tctcaattgt ctgaaaggta gagcccacta ttgtgcctta taagccccctt  6000
tcactatctg ttccccacat tcctttttag cctcatcccc ccattgttcc tgtgtgtacg   6060
taaaccttat gttttagttg cagctgattt ttaactgctc ttttttttctgg ctttgtgcct 6120
ctacactgtg ttttcttcct ggtctctctt tcctgtcctt attaccactc tttgaaacac   6180
gtcagaaaaa cttttttctgg actttgggcc acttgtcatt ccctgtgctg agacgcattt   6240
tgctttccag agatcttggt cattgctgtt atcctctgta gggtcttctt ttatctccct   6300
cgtgagacag ctctgggaag aaaaagatat ttatttctaa tccctgtgcc taataacagg   6360
tctattctct tgatatccat tactgaagaa atgtttgttg agtaagttct tgttttaatt   6420
tttaaatata aattttttaat ttttatgagt acatagtagg tacatatatt tatgggctac  6480
atgagatgtt ctgatacagg catgcagtgc aaaataacca catcatggag aataggatat   6540
ccatcccatc aagcgtttat cctttgtgtt acaaacaatc caattacagt cttttagtta   6600
ttttaaaatg tgcaattact gttgactgta gttaccttgt tgtgctatca aatagcaggt   6660
cttatttatt ctattttttt ttgtacctat taaccatccc aacttccctc agcccctcac   6720
tacccttccc agcctctggt aaccatcctt gtactctctg tgtccgtgag ttcaattgtt   6780
ttgattttta gatcgcacaa ataagtgaga acatgtgatg tttgtctttt tgtgtctggt   6840
```

```
ttatttcact taatgtaatc atctccagtt ccatctatgt tgttgcagat gacaggatct    6900
tattcttttt ttatggctga atagtactcc attgtgtata gtaccacaat ttctttatcc    6960
agtcatccat tgatggacac ttaggttgct tccaaatctt agctattgtg aacagagctg    7020
caacaaacat gagagtgcag atatctcttc catatactga tgtcttttcg ttttgttttt    7080
ttaattgttt tgattgaagt tgcagtcagt ttttactgag atgctagtgt ttgaatctct    7140
cttttcaatt ttctctgtct cagctggagt gtgttgggag tgtagccagt ggtatctctg    7200
ttatgagttg gagtcctgac caagagctgg tgcttcttgc cacaggtaag cttgttactg    7260
gtgcctcact ggcttttttta aaacattatt ccagatgtct tacaggcttc atcagcttta    7320
ggctgcttga atttcaaaaa atttctttga accagtataa taccaattat gaaccagtat    7380
aataccaatt atgtatgtgt gtgtgtatat atatataaaa cgtagagtga ttttttttttg    7440 gtgactgaag ttttgcctct tagtctatca ttataaaaag ttgtttcatg taacttttta    7500
agtcttgggg agtaagaaac aaagtcataa aacttgggga ggctgctaag tccccagtta    7560
gagttaaaaa tgtcagcaat atgtatttta acttattcta agagttgctg tatggacaca    7620
ttctaaaagc ccttcttggg ttctgttgct gttttttcccc tttaagtctc atcattccag    7680
atgagtttag taaaccagct ccactgatga catttatatt tagaggtatc ttggggacaa    7740
ggagtgttga agtagtgga ggagggcttt gtggactttt aagttcaact gtacacacat    7800
taatagctga gcataagcac caggtgactt atctagggaa agcttttggg ggttttttgt    7860
cattgttgtt ttttttaagtc aaagcatttt ggatgaattc tgtctgctct gttcagacta    7920
actccagctc cttagcttac agtgccatag gtacttagga atggcaaatt tgttacatga    7980
aaacaaaatc atttttgttt gtgtttctct aaggtcaaca gaccctgatt atgatgacaa    8040
aagattttga gccaatcctg gagcagcaga tccatcagga tgattttggt gaaagtaagt    8100
atagctttgt gcaatatttt gtgacctacg tttcttccca tttttgacca tttccttgtg    8160
cactaatagc catgtcatta ggccaaagaa ctgtgaaagt taaaccccca gctattaaat    8220
gtctattagc ccagttcctt cagcccatcc caaatcttaa aaggcctact gatgcctctc    8280
caggtctgag ggtttaaggt cacttagata gttattaccc aaaccctagg aaagtcttag    8340
gctgggcttt cagtgaaagg gactgtacaa ggtagtattt ctgggataca gttttaggga    8400
gaagaaaaga agaaagatgg aatagaaggc tggttttttgt tactacgatt agatccaatc    8460
tgcatttcca tgggaacaat cagattattt tcttgctaaa atctagccaa ggtcatctgg    8520
gcattaaggc tgtgggggta ttgaagggca gtgcaggaga agagagacgc ttattaagca    8580
taagctttgg ccatcttgaa gtcacaaagt agctggcctg attgaagagg gatggggaag    8640
aagatgttcc aacttctgtt atggtctaac ttcctgcctt cttgctccat caactctgag    8700
aaatcattta gacaacttct acccatttat ttacaaataa tgtatttgtt cagaaataat    8760
tttggagggc tgggcacagt ggctcatgcc tgtaatccca gcactttggg aggatgaggc    8820
aggaggattg cttgagccca ggagtttgat actagcctag gcaacgtagg gagacccagc    8880
atctacaaag aatttaaaaa ttagctgggc ttggtggtat cagcacagta atgacatgat    8940
gtgcaggtac tggggtagca aagggaagg aaacgagtaa ctagagaggg atgatttatt    9000 tccctagga ggccaacttg agctgagtct cagctgaatt ggtgttgggt aggtgaggga    9060
taagggtggg gagtagtcag ctgaattggt attgggcagg tgagggataa gggtttggag    9120
tagtcagctg aattggtatt gggtaggtga gggataaggg tggggaacag tccaagcaag    9180
```

```
tgaatgtgtc catttcaagt gtccatttca agggagggtt atttcataga acattgtgg    9240 gttactcagg gaactgtgag taattcagca ttgctgaagt ggcagaatgt gagtgtagaa    9300
tgaaataaat ggaacagatt tgattgagtt tgtagtaggg aatatggaca ttgagttata    9360
gttgatcagc cattacaagt tttgatgata agaggtttaa agagatttat ttaatagaaa    9420
gatggctcgt gatggcatat ttttgttgtt tttgtgtgtg gagagggaag agatgagagg    9480
cagggtgatc aggtaggagg ttgctacagg aatccagatg aaagataagg aaggtttgtg    9540
tggggctaga agcaggaatc attcaggaaa aaacttgatt cacaatgagg atgggagtac    9600
attttttaga attagctggg aaacttttt agaatatatg tgcatgattc cccttctgcc    9660
ctaggccagt ttgagaaata ccaatttaga aagtgaaata aataggcttt gcgtatgtaa    9720
ggtgaataag aaaaagttga gcaggactcc agccagaacc tcaggtgttg ggaataaaga    9780
tgccagtaac agggaagatg gagaagtgct ggtctgtaag gggtgggtgg tgagatctgt    9840
tttggatttg ttgaaggacc atatgtgatt gccatgtgga gtatgcaaat ataaggctga    9900
agctcaggag aggccagagc tatggactga gagtagtggg tatgtaggaa attctgacag    9960
ttttgggaac agatggactg tctcagggag cagatgctgt acaggaagag tctagaatcc   10020
agggtggaac tctggggcat ccagcttga ggacagtcag agagagagta acagcacaca   10080
gtatactttg ggatgggaaa gtgctctggg cctggtgttt cccactgact ttttcacaca   10140
aatcctaatg cagtaaatca aggaaatgt aggccaagtt aagatcttag gtctcagaaa   10200
tgtgtttctc agtacaaaaa aaaaaaaatc attctatgga gtgatgaata tttttcctct   10260
atcctggggt cagtagactt gttctgaaaa gggctaggtc atgaatatgt tcagctttgc   10320
aggctgtatg atctgtgttg cagctgctca attctaatgt tgaggtgtga aagttataca   10380
tgatacataa gcacatctat gttccagtaa acgtttgttt gtaaaagcag atgtaggctg   10440
tagttttgca aatccctgct gtaaccgcat catttcttgt cttccattgg aaaagttctc   10500
tttcttcatt ccttggtcct taatcttcct gtggaaactt gcagatagaa gcctgggggt   10560
ttgcaccagg atagtcacta ccatttgtac gcagcagcaa ttgaggtact gtagcacttg   10620
gatgtgagca gacaggaaat ggtcatatgg acccataatt tataggaatt gcaaacagcc   10680
ctgcttcatc agaatcagaa tcaatggcag gaggaaagta ttgggtcctg gattaggtga   10740
tgttttcagg accatcttta ttgtgcttct tgcaaatgga tcctacctcc aggaacagaa   10800
gggttgtgtt gtttcagcaa ctctgcctaa tagtttatat aagagaagtg ttacgatcta   10860
gaaagaaccc cagtcagcct ggaaggcaga agacctgtgt tctaacttt ggctccacca    10920 ttagggaggg tctcaatctc taagtctatg tgaggagctg ttttgtgacc tgcagcccct   10980
ctatcaccag tgagagcttg caatcagaat tttattccca gttctcatct tggggttta   11040 tgttccggac atattttgta aactctttat gtttcattct tcttacttat aaggtgaggg   11100
tgagatcgct gacttgtgtc atcaaagaaa cttggaatat gtaagatggc agtaaaatgc   11160
tttccaaaat aaggaagggc atttcaaatt cttcaaagtc actgctgcat ataatatgaa   11220
atgggttttg tttgtttgtt ttgagatggg ggtctcgctg tgttacccag gctagagagt   11280
gcagtagtac aatcagggct cactgcagcc ttgaactcct gggttcaagt gatcctccta   11340
ctttagtctc ttgagtagct gggaccacag gtgtgtgcca tcatgtccag cttattttgt   11400
atactttttg tagagatggg tgtctcccta tgttgcccag gctggtctcg aactcctgga   11460
ctcaagtgat cctcctgcct cagcctccca aagtgttggg actataggca tgagccacca   11520
tgcccagcct gaaacatagg tttctcaaat attgactgct ggtcaattta ttgagaggcg   11580
```

```
ttagaggacc tgagtaattg ccaatgacta acttcatgaa gaatagcagt gaaactgttt   11640
ttgtttcatt tcatgtggct tattagttgt cttgccaatt gttctgtagg caagtttatc   11700
actgttggat ggggtaggaa ggagacacag ttccatggat cagaaggcag acaagcagct   11760
tttcagatgc aaatggtaag tttggtttga tggataaaaa gccttgactg gaacaaatgt   11820
aagtttgcca cccaccagga actctttggt gtccacttag atgccagtaa tgaacagttc   11880
tcttctgctt tagtaaaact gcctagaacc ttcaggaaat gaatccctct agaaagatcc   11940 ttttttttcct tgttattgcc aagttgcttt gtgatttatt ttcatagtag caaataatta   12000
taaccaatat tcatcaccca gtttaaaaaa taaaacatca cagacaaagg aaacccctg    12060 tgtatcccgt cccgatgtcc ctccccttcc tctccagaga gagctgccat ccttcattca   12120
catgcatgtt ctcatacttt tcccatatat gtgtatatta gatattttc tttttctgtt    12180 ggatgaaact ctttgttttc cttacttctg gattggaaaa ttctgaagac catataatga   12240
tgtcttgatg actcaaggca ggactttta atcttctaat gtaggcgggg cggcccctga    12300
aggcagaggt gtgtggacac aagaagagtg cagactcttg gggcacctgg ggaagtagtg   12360
tccgtgtcac attaaattca tttaaactct tatatttat tttaatttat acaatatgaa    12420 tatttttaa aactatgaat tgaaaagtat tacccttgag taaaattaat gccccaagaa    12480
gatgtgccat atttaccctc tggcacacta ccaagtaccc ccaggggcat tacagatctc   12540
tgttagaaaa gtacagatta cattatcctc ataacattta gaagctatga gaccttggca   12600
gggaagtttc ctaatgtttc tgagcctcag tattctctgt aaagtggaca acataatgtc   12660
tccttacaag ggttgagatg gcaggtaat agcatatata aaacagctat catagcatca    12720
gcacagtgta ggcactcaaa tggtagttgc tgcttttgtt ttagtagaca aataattttt   12780
gaaacttttt aaagcgtagt ttttatttca aaacaacttt attgtgagta aaatatgcat    12840
agtgggtcta atttaacatt ctgaaagcta ttgacttatt agaacagtaa aggattatta   12900
gagggcagaa acatggagta agtactctga gacacaacct tgcttctttg ggggtgatcc   12960
actacaactg cccagctttg gacaagtggt tttcatgtcc ccctgatttt taagtgattt   13020
tttttttttt tggcaggact taaaaggtat ccttgactaa acaggaactt gaccaagtaa   13080
atagttggtg caatttgaat attctttctt gctataagca acaagtaaat tatggtacag   13140 cttttctaaga ccatatcttt tcgatttaaa aatagcactt tactcataca tgttatgaca   13200
tgggtaaacc tcataaagat tatgctaagt gaaagaagcc agtcataaaa gatcacatat   13260
aatatgatcc catttgtatg aagtgcccag aagggcaaa tccacagagg cagaaagtag    13320
agtagtggtt gggtagggct gtggggtggg gtggggaagg ggtgactgct aatggatatg   13380
gggtttcttt tggggatgat gaaaatgctc aaaatttaga ttatggtgat ggctattcaa   13440
ctttgtaaat atactttaaa aacattgatt cttaccactg agtttaaaca accaaaaaa    13500 aatcccaagg tgcattgaat tgtgtacttc aaatgggtga accttaataa tatgtaaatt   13560
atatcccagt aaaggtgtta aaaatagta cttaaaagga atctatggta gttttgaaaa    13620
taaggcagtt ttccatactt tgttaaactc tggagaagat gacactttac tactggtacc   13680
tgctagagta agacttatct agtattaaca aaattagggt ttattaatgg tataggatga   13740
tccaggtaat gggggaaaaa aaccgagcat cctgttatct aatgtactat ccagtaaact   13800
actctagctt ttttttcatga actttttcta aaggctttct agggcctcgt cttggtttga   13860
aagttcacag ctacccttca gaaaagaaaa caaaaatcca tggagtaggc agatacaagt   13920
```

```
actcatgtga gcataattta cttttgatttt ttaagttgtg ttattctagc cctcagcctg    13980
ttccctgcct gggctctcct agtgcccagt aacactgatt caagaggttg catttagctg    14040
ggcacagtgg ctgatgcctg caatcccagc actttgggag gccaagttgg gcagatcacc    14100
tgaggtcagg agttcaagac cagcatgtcc aacatggtga aatcctatct ctactaaaaa    14160
tacaaaaatt agccaggcat ggtggcagat gcctgtaatc tcagctactt gagaagctaa    14220
ggtagtagaa tcacttgtac ctgggaggca gaggttgcgg tgagccaaga ttgtgccact    14280
gcactccagc ctgggccata agcaagact ccgtctcaaa aaaaaaaaa aaaaaattgg      14340
gtgagaggga ggaattgagg aggataccaa gggttgggcc tgaacaaatg gaagcataat    14400
tatatgtaga aatttctatg agctactctt ctagaataga tgactcaata atacccctgct  14460
tgccatctac gttttctgtc cttaattatt tccagttcta tttcatataa tgcctatttc    14520
aggccttaac ccttcagtaa aggaggtttg gtttctatac cctaggacag tttcattgag    14580
aataaatttt gttaggctac ctatgtattc cctactgtgc agactacagt acagtactag    14640
cagaattctt aggctgttac tagaatatga tgatgaatgc ccgggtggtc atctgtctcc    14700
cacccggtag agttggcttc aggattgaga tacacgtggc cctggaggag acgtttcttc    14760
ccgtcatgct gcagaatgag aacatttcca tgttttcgtc attgtctgct gctgccttta    14820
ccacctctgt ggctcctccc tattcacctt gttcacatct taactcatct gtgccctgtt    14880
gtgaagctta cacaatatgt aaacaaaact ctaccctgtt ggacaaatgg aacacttgtt    14940
tccttgttgt agttacctga taggttcctt agctcattat attcaggatc tagatctgta    15000
gctctttttcc tcttttgctg ttctcagagg ccactttttt tttttttaat gccgaaagga   15060
ggattttgtt tgttttacat ttttttcttc ttttttgatga tttctgcgtt ctaagaacca   15120
acccttggat ggtttctgat tctagaggca ggctttcaaa gtagcttaaa cctcttaaaa    15180
aacatctgta tctagtggtc tgaggcttgt ttgattctgg gatacttaag gtcccccagt    15240
aatattggtg tttgttcccc ttttttagcat gagtctgctt tgccctggga tgaccataga   15300
ccacaagtta cctggcgggg ggatggacag ttttttgctg tgagtgttgt ttgcccagaa    15360
acaggtatgg aaatatattg cagttaaaca acaataaaaa atttttatct tattaaaatt    15420
aaggaaaatt ttctttcttt tgctttgagt agggtattaa ttatacatat gaggcaagga   15480
tgtgctgctt taaatgtgaa atgaggttag agttaagaat tagaagagtc ctttgaggcc    15540
atttggtcca tcctcctacc tggtggacac aaatttgtaa caaaattaat ctaattggct    15600
atgtaaaacc atggcagttt ttatttgtaa ggaaggtgtt tgaatagttc tgaattgaca    15660
acttttatca taatgtttta agtgtgtatg tgtgtttgac tccactcccg cacaggggct    15720
cggaaggtca gagtgtggaa ccgagagttt gctttgcagt caaccagtga gcctgtggca    15780
ggactgggac cagccctggc ttggaagtga gtgggagaag aaaccttaga gaaattcttg    15840
gaaccagagt agaggtggtg gtacacatgg atacagatga tacagatgtt tgtgtaacac    15900
aaaaggattt ttacgtttct tcatttggtt ataaggctgt atctatcttt gtttcttctt    15960
tttttttttt cttattccct gaagtctgaa ttcaactcga atagtagatt ttacgcttct    16020
tcacagattt cattgttcca aggccgcata tattttgcat tcctaactct taaaaggctg    16080
tggttttaag gcagggtata tatgaagcca ttgtacagag cagaaaatgg tgtttagaag    16140
ggaaggccca gtttgcaagg ctctgtgggg caaatggtgc ttttgtggaa attagggaaa    16200
gagcctcctt ccttggcaca aaattcctac agcagaggat ctgcttgcca aggagcatgc    16260
aggctggatt cagaccctgc tctttccttc cattctcctc cttggcccag tacccttgtg    16320
```

```
caggttacaa tttgcctgtc atatgtggct gcctgatttt agatagaaga tgtatctcct   16380
ctgtttcggt gatatctgtt gtatgtagac ctcttgtttc ccaccagtat ctgaatggta   16440
ttatatgata gagcagaaga gaaatgtatt tgaattaaaa ccctagagac aaatatgaat   16500
aagatgaggc aattaagatg ttttcaacat tggtgaagt cttaaaaaag acctactgga    16560
gcatagaata tttgctgaag ttgtataatg gaaggagaaa tagattttga tttttaggac   16620
attatacctg gaatggttta gataacttat tattttaaa gtcatccaaa tgcaatgtaa    16680
atatgtaagg ttttgtgggc aaatggagcc tctgtgtaaa acaggaaaag gcactctttc   16740
ctctgggcaa gtacagtccc acagtgggat gaaccgctcg ccgagagaca agggacacat   16800
gggatttaaa acttccttgg ataaagatat tcattaattc gttcattcat tcattcatgt   16860
ttgctggaaa aaaaactctt ctggatttta tctattcttt agttaggtga gctttcgata   16920
ttgtaacact ctgagtttgc tttaagaccc tcaggcagtt tgattgcatc tacacaagat   16980
aaacccaacc agcaggatat tgtgtttttt gagaaaatg gactccttca tggacacttt    17040
acacttccct tccttaaaga tgaggttaag gtaagtgcct gagtttgttt caccctcgaa   17100
tgtagaggac tttccatagc tatagaggga attttttttt tttttttttg agatggagtt   17160
tcattcttgt tgcccaggtt ggagtgcgat agtgcaatct cggttcactg caacctccgc   17220
ctcctaggtt caagtgattc tcctgcctca gcctcccgag tagctgggat tacaggcttg   17280
cgccaccaca gccagctaat tttgtatttt tagtagagac ggggtttctc cgtgttggtc   17340
aggctggtct caaaccctg acctcaggtg atccacccgc ctctgcctcc caaagtgctg    17400
ggattacagg cgtgagccac cacgcctggc ctatagaggg gattatatt tgatatggat    17460 atataaatag tagctttaga gtaaatagta ataaaaatgg tggcttccta gaactgattt   17520
ttatttaata aaatattgtt tttccagtga ttttgcaaat aatagcattt gtccccacc    17580 ttagataaaa cagaagtagg aaataaaaat gctagttttt attgtttatt ttgacaaaag   17640 cataatttt ccagtaatga agatgttttt catttataac atttaaatct taagtggttt    17700
gtataccatt aagattcttg ctgaagtgag aacacatcaa atggtatctc tgtgtaaaat   17760
tttaaacatc ctaagttgag agacgagttt aatgaactcc catgtaacta ttactcactt   17820
tcagtagata ccaacatttt gcaaaactat tttcatcggt ccgcaactct ttggcctata   17880
catatatata cttacatata ttttattc ctggagtttt aattctagaa atcatatttt     17940
caatatttat ttataacagt taaggacatt tttctttaca taaccataat tctattatta   18000
catcttatct ctgtgttgtc taacacccag tccatattcc agtttctctg attgtctaaa   18060
aatgtcacct tgtatttggt taagtttctt aagtctcttt taatctttaa gcataatgta   18120
tttctttttt ttaagtcctc tacataataa tgacatattt tacagatttg tttaatgcct   18180
ctgtaggtta gtgatttaca gctagggatg agctcaggta gtgggattat ttgatttgag   18240
agaggaaata cagctattat aaagatttgg aagtaaatcc ataactgaaa gccaatgaca   18300
gatctttttt cccttctagg taaatgactt gctctggaat gcagattcct ctgtgcttgc   18360
agtctggctg gaagaccttc agagagaaga aagctccatt ccgaaaacct gtggtaagac   18420
agctgtagta ccccagcctt ctgccccata aaacgtagtt gaaagtagac aggtatggga   18480
tttccttcat cccttctact tagtccctta gtagaatcaa agatgctgaa gtgggtaggt   18540
ggaaatgggg gtggttaggt tttgattgat tgtggatttc agtcatgtat tggttggggt   18600
tctctagaga aacaaataat acatatatat aattcgtccc tcagtattct cgggggatta   18660
```

```
gttctaggat tgcccatgga cgccaaaatc cacacatggt caagtcctgc agtcaaccct   18720
gcagaacact cagatatgaa aagtcagcct tttgtatact tgggttttgc attcctcaag   18780
taccatattt ttgatgtgcg tttggttgcg ggtatagaat ccacaatatg aagggccgac   18840
tgtattcatt gaaaaaaata cgaatataaa tggacctgtg tagttcaagc ctgtgttgtt   18900
caagggtcag ctgtacttac atagagagac ggtgagagag ggaatagggt ggggcgggag   18960
ggagagagag taatagagtg tggatagatt tactttaaaa gattagctaa tgtaggggat   19020
ggcaagtttg aaatttgtgg gggcaggttg gcaggctgga aattcaggta agaattgatg   19080
ttgctgtctt gagtatgaaa tctgtagggc aggctggaaa cttagggagg atttctgtta   19140
cagccttaag gcagaatttc ttcttttctg cgaagcctca gttttgctt ttaaggtctt    19200 cagctgaatg aatgggacct tcccacatta tggggaataa tctgctttcc ttatagtcag   19260
ccgattataa atattaatca catctacaga ataccttcac agcaacatct ggagtttagc   19320
agatagctgg gtgccatagc ctagccaact tgacacaata aaattaactg ttgtaagtca   19380
tcacgtgctt tccctagtgc atggtattac cacagaaaaa acactaacca aaggaattct   19440
gtggacgtga aagaagattt agattaagcg taaaagtaag aatattttta tagcttttaa   19500
aatgtataag tgtgtggttt taagtattaa ataaacttg aaaatgttag aaaataagat    19560
gagaaaaaaa tctcatagtt ctaccacttc gtaataatca ctattcaaat tttcttgtct   19620
tctaggtttt tcatgtatat atctcagtat agctatcatc ttgttttgt taaaagtgta    19680 gtaggtatgg gccaggtgcg gtggctcatg cactttgggg gcccagcact ttgggaggcc   19740
gaggcgggcg gatcacgagg tcaggagatc gagaccatcc tggctaacac ggtgtaaccc   19800
catctctact aaaaatacaa aaaattagct gggcgtggtg gcaggcgcct gtagtcccag   19860
ctactcagga ggctgaggca ggagaatggt gtgaacctgg aggaggcgga gcttgcagtg   19920
aatggagatc gtgccactgc actccagcct tggcgacaga gtgagactgt ctcaaaacaa   19980
aacaaaaaaa agtgtaggtg tgatacatct gcatcatttt aaattgctgt ataatactcg   20040
tttattctcg ttcattaaat ctcatgctgt tagacattta cagttttgtc atttctcatt    20100
attgtaaaca gcaatgcatg gtacattttt gttcataaat cttttacttt gattattttc   20160
taagtagctt tcaaactctt taatcagtag accccccccc ccctttttt tttttttgg    20220 agacggagtc tctctctttc ccccaggctg gagtgcagtg gccgatctc ggtcactgca    20280 agctctgcct cccgggttca ctccattttc ctgcctcagc ttcccgagta gctgggtcta   20340
caggcgcccg ccaccaagcc tggctaattt ttttgtatttt tggtagaggc aggtttcac   20400 cgcgttagcc aggatggtct cgatctccat ctcgtgatct gcccgtctcg gcctcccaaa   20460
gtgctgggat tacaggcgtg agccaccgtg cccggcctca gtagaaccct tttaactgca   20520
atgttaagaa actcattatt cattcaacac aatagttctt aaccctggcc acacctttag   20580
aaaaaaaatg atattcaggc ttcatctcaa gagttcagtt cagtgtgttg gaatggagat   20640
tatacgtaag tatttaatta aaaccaaaa gcccccaagt gattttaaac agccgcagtt    20700
gagaaccacc gattaaccag tgtgtcaagg gatggcactg tgatatgctg agcataaaaa   20760
tattgcacag gatgaaaccc tgtctctact aaaaatgcaa aaattagtcc ggcgtggtgg   20820
tgcgcgcctg tagtcctagc tactcgggag gctgagacaa gggaatcgct tgaactggga   20880
ggcagaggtt gccgtgagcc gagattgagc cactgcactc cagcatgggt gacagagtga   20940
gactccatct caaaaacatg tatatatata tatacacaca cacacacatt gcacaagaac   21000
agccacaaca tctgtgctca cagaacatca gcatgtggtc taacttcaaa gtgttgtaat   21060
```

```
aatgcggttt gagactaggt tatgtttgct gtgatcacta agttaagcat tagtgagcaa    21120
ggagattgag aaaatcctta atataaataa tatttcttaa tataactata attcctaata    21180
taactaaggt cttaatttat atgtcatctg tttagtaaag gttggttttg gcatgattaa    21240
gtcttgcttg cttaatagat gttggaagga taatttcatg cttatcttct ttggacagct    21300
gaatcaggat taatacccag atagccttga acataagtgc ttgcaaagca cctgaaagaa    21360
aataagcatc ttaagcccaa tacaacacaa tgatgctagt ctagatcttg gattaagtgt    21420
tttaatactt ttactctaat tgccaagtta tcttcttcct aaatcttcat gagaaaaccc    21480
actaaaagaa tgcttttttcc tggtagcctt ccattgtgat cataaagttt ggaagtaaag    21540
ttgaaaataa acatgtgggc caggcacggt ggctcaggcc tgtaatctca gcactttggg    21600
aggccgaggc aggcggatca caaggtcagg agatcaagac catcctggct aacacggtga    21660
aaccatgttt ctactaaaaa tacaaaaaaa aaaaattagc cgggtgtggt ggtgggcgcc    21720
tgtagtccta gctactcgag aggctgaggc aggagaatgg catgaacccg ggagatggag    21780
cttgcagtga gccgagattg cgccactgca ctccagcctg gccggcagag cgagactctg    21840
tgtcaataaa aaaaaaaaaa aaacgaaaat aaacatatga ataaaagtta aaaatagaaa    21900
aaaaacaaga aaataaacat atatttctga ccttattgat tcttgatatt ttatctgcat    21960
ggaaagctat tttttggcag ttattattgt tcttattta  gagacgaggc tgagcaggaa    22020
gggtcctttg aaaagaaaa  gattgcccctt gaaccctct  ggcaagtggg atgaagtctg    22080
cttcccagcc tctaacggcc ttcttttcat tttcccttgc agttcagctc tggactgttg    22140
gaaactatca ctggtatctc aagcaaagtt tatccttcag cacctgtggg aagagcaaga    22200
ttgtgtctct gatgtgggac cctgtgaccc cataccggct gcatgttctc tgtcagggct    22260
ggcattacct cgcctatgat tggcactgga cgactgaccg gagcgtggga gataattcaa    22320
gtgacttgtc caatgtggct gtcattgatg gaagtaagct cctgggaagt gtgtccatga    22380
gcctgcaagg ggtcctgagc ctagggcctg cagatgtggt ggtttgactg gaacagtggg    22440
gaatctttat ttgttttggc tgtttgggtt acttgttttt ttattgaatg ggatataagg    22500
tggggtatgt tctctcctga gaaccattgt ccccctccc  ccaccagttt cctgttatac    22560
tgcatctgtg gccttcacac gtttacttgc ctggcctttg aagacactga aaactttgac    22620
tctaggtaga gaggatgaca acagtacagt cttgtgggat tgggtgtgtt agctttatct    22680
gtttgccctg acacagattt ataattgacc cttataccac cccacttgtg ttgctttgtt    22740
tcctgataca aatgcttgct gatatatacc tctccagtat gttcagttca tgcataaacg    22800
tttgcctaat atgaagatta ggtttatatt ttataatgag gtagaaggtt tttttagggg    22860
gtggggtggg aagggcaaga ctgaagagtg aagtagtcac cttaatgaat agtttcattg    22920
ctgatatgaa agggagcact ggcttctaag attgtaatgt gaggtggtat attaattcat    22980
attctgtgta atattctaca taatactgat tttatagtca tgtattctat atagagaact    23040
taatcagatc tgcgttatta ccaaatccac acataggaaa gtgctttaag gattttgaaa    23100
gtattaattc ccttggttta gtgtggcttg gttgcaggcc caggtttaaa gctagaggtc    23160
tgacctcttg gcctttttgc cttagtccct ggcacctgaa actccaggta ctgagatgga    23220
ctcccctagg cctagaggtg acaatagcca attatggaca gaacccatga catttcccca    23280
tcccacactg tttttagact tgttcctgag aaaaacattg aaagttattt ttttgtgaat    23340
tgccattatt gtttagatat actgtgatgt tcagatggct tatcttacaa attgaatatc    23400
```

```
cctaggtcta atcctcttct ttcttttttca ctgcagacag ggtgttggtg acagtcttcc   23460
ggcagactgt ggttccgcct cccatgtgca cctaccaact gctgttccca cccctgtga    23520 atcaagtcac attcttagca caccctcaaa agagtaatga ccttgctgtt ctagatgcca   23580
gtaaccagat ttctgtttat aaatgtggta tgttataaaa cttttgccaa gatgttctga   23640
atcaagtccc ttctactcct acataaaagc aaattatagt ttggtgttgc cataggtcta   23700
gtgtttctca aaattttttaa gtctgcagtt gatatcatta tcattatgat atttaattgc   23760
cttgggtttt tgtttttttt tttttttaatc ctatactggt ttgtacgagc cattccttt   23820 cccttactga cttgaagagt cagttattta agaataacat tggactctgg aaataacata   23880
gtatgttata cattgttaac atgttttact cttttcatag cctttacaca tattttcagt   23940
tgatctcatc cctcctagga gctgtgtcag agatgggggtt ttcctcttt gtagatgagg   24000 gaacacagtg tcagaggttt tgtaatttgt ttgaacaaga atggacaagg acctcaacac   24060
aggtgttcta gctcctaatc cacttgtcct gccacagccc cattgctgtc agttcttcat   24120
tactttcctg atgtgctgga gaatctgaaa tttgttttta cttgtgagtt ctgtggttat   24180
gtcataaatt ctgctggcat atggcagtgt tagccttgtt ttcaaatatc ttttgaattc   24240
tcagaaaaag cctagatagt tgccaagaga gaataatcaa aattaattaa tttaaatggg   24300
aagtccttac tttcatatca gcttttctgt taagtcagca gcccactgtg tacatggatc   24360
ctatctggat gtatcaccag tttctctgat tatagtttca gtgtgtaaaa tgctgttaca   24420
gtcctcctta aacttttcaa aatagcttta aaaaaaagtg caaatatgtt cattgtcaag   24480
gcaaaaagaa tcagatgtaa gcttttgtgg gacttaactg tatgatgcta atgagtttat   24540
atgtcacttt atgatgtatg gtatgttttg ttctgcattc acttaaaaaa tagctttata   24600
tcattcatct atttaaagtg tacaattcaa tggtttatat gtgtgtgtat gaatatatat   24660
acatatgtat atgtatatat atgtatattc acagagttgt acagccatca ccacgatcaa   24720
ttttaggacg tttttatctc ctcagaatga aaccctgtac caccctgcat tcattttact   24780
tgagagaaaa ctccctgtga tgagatagga caggttgaga gctccacttt tgaaagattg   24840
ttcggcatca atatgtgggg ttggccatag gtcaggggca cctggaggca gagattctag   24900
ttaggagaag ctgttgtcaa gtgtccaggc aggagctagc aagagcttga gccagagcag   24960
tgttcataga aatggaaaga agagaaagat cataacaaat ccatgaagta aaacccctga   25020
gaagttaaag aacccactgg ggagagtttg gatataagag aatctggaaa aagagatctt   25080
ggactggaac aggtcagggc tccgtgccca agtggaaggg aaattaagaa cttggagtca   25140
agtggtagac atttgagtgg tgtggagaca agttcgttgc caaagttttc aaagatggtg   25200
tttgatgcat cctgagtatc actccttttt cccctcatt gcttcttgat tgtttattat     25260
atgccaggct ttttctagt acttggcttg ttgtactaga aaactagttg tactttgtct    25320
acaacttgtt gttctaggtg tagacaaaag atatcaatta aatatgatct atcagatggc  25380
aagtgctgtg gagaaaaatt aagcaaaata aggggtaggg agagcttaag gataagggtt  25440 tacagggga aggtgtcttt cctatttagt gtgatcccaa aggcctctct gtgaaggtga   25500
cattgaagca gagacctggt gagaatcaca gtggagccca cgcagacatc tggggtaaga   25560
gcgtcccaag cattctatgc ttgaaggcaa agaagaaaaa agaaagagcg ttccaagcag   25620
agtaaaaagc aaccaccgaa gtgcctgttg tgtttaggaa atagccagga ggccagggtg   25680
gctgcagcag agcaaaggag gggaaggtgg tgggtgagtt cagagtggtg atgggaatct   25740
gctcttgtag ggccttgcgg cttttactcc gagtgagata ggagccacca gagggcttag   25800
```

```
aacagaggag tgcagtgttc tggctgaatt ttttaaaggc ttgcattggc tgctgtgcag   25860
tgaataaact ggatgaagaa tagaaagaaa atgtctttta agcaggtgct taggactttg   25920
gagaatttga ggatattgag aggtggttga agacagtgga ggaaattgtc cacagcactg   25980
ggctgagagg gtagcccctt cacctggtct tgctgagatg tggcctttgt cagggaagat   26040
tatgactgat gtgttcttaa gaggaaagca gaaattttaa ggaggttgag atgtgattat   26100
tttctagatt gctgtttgcc ttctagaact cattaattgc agacaccatc cccttagtat   26160
taggtgaaat cttataattt acgatgataa tatttgcatt tttgttttcc aggtgattgt   26220
ccaagtgctg accctacagt gaaactggga gctgtgggtg gaagtggatt taaagtttgc   26280
cttagaactc ctcatttgga aaagagatac aagtaggttc ttaattatct tgggcttctg   26340
ggaacagaat cagccagcat gcagtcctaa attcagccat ctgataacag ttctatgcct   26400
gttgctgagt ggaacaagaa ataaagacaa cacccaggcc ctgactttcg gatctgattg   26460
gagaagccag tcatgtagtt tgtctgaatg ccatataatt tgataggtag caggagagca   26520
tgagttgtaa gccagcctag gacctactcc caatagcgct tggttctcca ggaaaaatca   26580
tgtgggaaaa atgagagtga caatgataag gcggagctgc attctcttac ataaatgggg   26640
atgtatgggt tgttaacatg gatgacctaa tgcagcctct gtctttgctc catcccagaa   26700
tctagaactt ctgggtgctg tgctttgagg ctcctgggat ggaaatcaga atgcattctt   26760
ccattgaaac agtattgtaa acaattggat gttattgaat acctcaggta cactataggc   26820
atttgcaaaa tgacctagaa accaaattat aatgccacat ctgtgagaga actttttaa    26880 aaagtaccac ttattgagta cttacagatt aaaaaaacaa agtgtagagg ttaggtaact   26940
tacccaaggt catggacctg gtaactagag aatttagggt ttgattctat tctgtttgat   27000
aagtccatgt tcttcattac taaactactc tgcctccagg gaacatttat tgttagatta   27060
atagaaataa ttaactgagt acaacaaata gcagaattta ataaataatg tttcttaaat   27120
atatgtgata tatttaataa atacagcaga agtgttcaac ctctgtatga ttttgaggct   27180
gcctgtataa tgcttagtag tttttaaaga gcatttacat gcattatttc acttcataga   27240
cttgaaacca ctagagtaga gatagaggac aaattagaaa gtatgaggca gtttagaata   27300
tagtttcatt taaaaaaaat tgatggggat aatgccaatt cgtctgagat ttcacagaag   27360
acatgagtac tcatcgtgat cttggggaag ggataggttt ggggttggca aagaattggg   27420
aacattgggt ctggtgggga agaaagtgtc agtgaaaacc agaggtggga ctgatcctcc   27480
atgggatact ctatgtgaat gcaatggaga gcctgagtcc ggggagagat gtttgaggag   27540
gaagatcagg ctagtgacca acttcttcag tgggagctgc ggatttgcca cctgatctaa   27600
aaggcaggaa gtagccattg tcggttccta cgtgaggtga caagaacagt gcgctggtca   27660
ggtgtataaa tgctaccaaa gaatgcatta gagacatgga gaccatctct caagctagtc   27720
agtcagttta atgtgaggtg cttaggaaag gacccattct actgcaagtg acatacctgc   27780
cagagcctgg tttgaatgct ggtaagtcat ggcagtggaa aagctctggg gttcattagt   27840
gtagggacta gggctggtaa ttttcttgtg tagtcagttt cctcaagtgt tctcttcaaa   27900
tttaaagatt tcagggtatg agaaatttag ggaaaatata aaaacgtatt cttaagccag   27960
acaaagatta attttagatt ttgtagtatt tggtagtatc tcaggttttg tccctccaaa   28020
taattaggag tggactgtat acaagatgct tcagtcttcc ttcatccagg aacgtctcag   28080 tggttttaa gttttattca tgtcttggat attcttcaat atttacaata gaatccagtt    28140
```

-continued

```
tgagaataat gaagatcaag atgtaaaccc gctgaaacta ggccttctca cttggattga    28200
agaagacgtc ttcctggctg taagccacag tgagttcagc ccccggtctg tcattcacca    28260
tttgactgca gcttcttctg agatggatga agagcatgga cagctcaatg tcaggtattg    28320
cagttttttcc ctgtactcca catgttaagc aaatggagtt aggttttgtg ctttttatgag   28380
catacaactt ttgacttcta ttgatcaagg ttgaggagca gtagctttct tgttagacac    28440
acttaacaag aaggttaagt ctagttatga gccatgtcaa aataacagac caaaaatata    28500
tcaaaaagtg gtgaaaaata ggataaatat tagtagatga agcaactttt taaagatatg    28560
ttaaatattt taatttagca tctacccaca tttttccagc gtgattgtta tatgttataa    28620
ttgattttaa taactgtcaa gcataattag agtggctaat tctcatgggc taatgtgatg    28680
ggaagaaatt ttgtataaat gcagtcatgc gcatatatgt gtgtgtgtgt gtgtgtgtgt    28740
gtgtgtgtat acatacccttt tctatgttta gatacacaaa tacttgacat ggtattacaa   28800
ttgcctgtag tattctgtaa agtaacatgc tgtccaggtt tgtagcctgg tagcaatagg    28860
ccataccccca taggctaggg gtgtagtagg ctacaccacc taggtttgtg taagtactct   28920
atgatgtttg cacaatgatg aaatcaccta acaacacatt tctcagacgt atccccatcg    28980
ttaaatgatg cataattgca catatatgct ttgttttgat gtggtgactt caaaatgctt    29040
cttccagcct cctcttctat atatcctatt ttgtacctga ctacatttac cattagaaag    29100
tctctattct tctttgctga aatttcactg ttctctgggc ctgagttttg ttttgattcc    29160
tgactatatc ttcattatgt aacaggtttc agttaatgaa tgctcttctg tgtaatgtaa    29220
gccctgttgt atagttgata gcattttcta gccagttccc agaactcctt gtttccagtg    29280
tcaatacttg gcacctttgt ccactgacac taatccccag attaatttgt aattaaagcc    29340
ctactggtga gatttctgag aaacgttgtt gcaaaattag gaacctttcc tttatatata    29400
tacattacat aaatttatag acataaaaca ttttaatgca gtcatttgct gctactcttt    29460
gactcatagt ctttcgtgat attttgaaaa agcctttgt taacatgtct aaatgcagaa    29520
tatgttctag aaatatgtag cacttaaagt aagccattag attaccttt gaaaagcgga     29580
gcaatttact aagtttctac ttcttcagat ttgaaattct tcatcattag cttgtagagg    29640
caaaagcttg atgcagtcat ctcatttgct gtaaggaaa tgagaagtca tttacagtat     29700
atttctactg ctttgacttt tatttctcaa aaagactgtt ttgttcatat aaaatattaa    29760
tgcttttgag gactacaaag tccctcgatt tagtttacat ttactttagc ttatactttg    29820
taaaaaatac tcttctaaat gctttgtctg ttttagctta cttatttctc ataataacctc   29880
tgtaaagtat atgccatttg caccatcatt ttacagatga gacaactaag acatggagca    29940
gttagataac ttgcctgaga tcatgcaggt ggagccagga tcaaatccca gcgagtctag    30000
ctccagagtt tgttctcttc ttgacagata atttatcctc acaaaatttg aagcatttgt    30060
agaggaattc cctattgtta taatgtttag ttttttttgta gattggttaa aaactttgaa   30120
ttaaatgtta gcattaacat catttgcttt tatcactact tctttgtctc ttttttctttt    30180
ttttaatcac tacctcttcc tcctcttttg agaaattctg cttccgtggc tatggtccaa    30240
gctacttgag aaggtgaggt gggaggatca cttgagccta ggaggttgag attgcggtga    30300
gctgtgattg tgtcaactgc atttcaacct gggcaacaga gcaagacact gtccaaaaaa    30360
aaaaaaaaaa atagtgaaat ttacttcgc tccattgact cagggaaaaa atgtaatggt     30420
gataacaaat tcccttcatc tcattagtga aaatccacaa ttttccatca atcgatatga    30480
tagtgataga gatattgagt gtgctcattt tcctacagac cagctgcttt aactatttta    30540
```

```
agcagacaga aatgatattg gtaccatcca tgtctaatga aggcaatact ttgtaataag    30600
ttgcagtaag ttgtggccag aagaggaatg atgacttcac agtgtaaaca actaccttat    30660
tgggtttgtg gaaaatggtg tcatgtagca gatgtggctt tatctgggct ttggtttgga    30720
gtagttttat ctattcatct aaccgtctgt ctctaagtgt ataagtgtgt gtgtgtgtgt    30780
gtgtgtgtgt gtatagtatt gggtgtgtat atatgtattt tgtctacatt gtattgaagt    30840
aggtagtgca gcatcaaaag gaaattgttg attttcaaaa tcagtgaaat gtcactattt    30900
ttgagaaaaa tggtctgttt acactccctt ctccttttt tgtcagttc atctgcagcg    30960
gtggatgggg tcataatcag tctatgttgc aattccaaga ccaagtcagt agtattacag    31020
ctggctgatg gccagatatt taagtacctt tggggtgagt atcaaggtgt taggaaagca    31080
tgttatgact tacatagatg cttagttctt aagaacatgt acttgtatct tgtcagttca    31140
atattgattg tcaggtcttt taactaccct ggaaaccct aagctttaga gtggaattgg    31200
caagtgtatt ctactcctgt ttcctctttt aatgaactaa cgtactctta aaaagtgat    31260
tgatgactat cgcagggaca aaaaccaaa caccgcatgt tctcactcat aggtgggaac    31320
tgaacagtga gaacacttgg acacaggaag gagaacatca cacacctggg cctgtcgtgg    31380
ggtgggggag ggtggaggga tagcattagg agatatacct aatgtaaatg acaagttaat    31440
gggtgcagca caccaacatg gcacatgtat acatatgtaa caaacctgca cattgtgcac    31500
atgtacccta gaacttaaag tataataaaa atatatatat aaataaataa tgccagcatt    31560
agagaaaaaa agtgattgaa attgcatgtt aagtgtttta gcaaatgttg atgttgatgg    31620
ttttttgcaa agagcgcatc agctatttgt gaactagatc tgtgaatctt gcagagtcac    31680
cttctctggc tattaaacca tggaagaact ctggtggatt tcctgttcgg tttccttatc    31740
catgcaccca gaccgaattg gccatgattg gagaagaggt aggtgaacac ggagcaggaa    31800
atttacttaa agtagttacc cagggactga tggcattaag tagaaagagc gtgggctttg    31860
gaggtggact tgggtctcca ctaaatgcct agacaatagt gggaaatgat ctcactttca    31920
taagccacac cttattcatc tataaaatg gaaaatcagt atctgtctat cagggttcag    31980
aagactaaat gagataatat atgtgattag caaccttta tccctagttg tacaaatcat    32040
tcaaagttaa ttttatttag gaggggaaac agaaatgtga tcttgagaat agttttagta    32100
gattttatt caacacatac tagaatgcct ataattgtgg tggatggtag aatgcagtgg    32160
ctggaaaaca aaaccgcttg actaattcct gctcttctgg aacttgtgat ctattaattt    32220
caatgtaatg attcccttg ttgggagtgt gatggaaatg acagagtat actggtagag    32280
aatactgaga tgtttgaggg gtaatttgag gatggtggct atgagaatgg gagtcctgca    32340
tctggtggtc caggaaggcc tctcggaggc agtgatgtgt gtgctgagat gtgaagaaaa    32400
agaaggctct gtctccaggc agaaggaaca acaaactcct tgagcttagc aagagctcat    32460
cttattcaag ggactggatg gaagtattgt ggctggagct cagtgacagt cataggaggg    32520
aatttgggtt ctttaattga acaaagatta gaaacttctt gtgattttta ataacagagt    32580
aatgtgttct gcttcatggt ttggacagtg attctggctg cccagaagag acttgattgg    32640
agagtgacga gactggaata tgggatcaac accggttgag tggagttagt gagggaaaa    32700
aggagatggg tttgagatat gtgtaggaga tggagatgtc agggctcact gatggattgg    32760
atggcttcac attccatttt gcactggacc agccacgtct taggtatcta tctttagtcc    32820
tgattacagg aacttaggtg tgaaatcata gggtggtaga actatgtgat agaaaaggta    32880
```

```
ggtttaactg atttgagata gaattgcttg tgatttcagt tttatttctt tgcaggaatg    32940
tgtccttggt ctgactgaca ggtgtcgctt tttcatcaat gacattgagg tatcaaggct    33000
tggtttggtg ttggatcctt ttcacagtgt tagctccgag taatctagct agctttcacc    33060
catgcctctc tggccttctc ttgcaggttg cgtcaaatat cacgtcattt gcagtatatg    33120
atgagttttt attgttgaca acccattccc atacctgcca gtgttttgc ctgagggatg     33180 cttcatttaa aagtaagttt tcaatgtata aaacagaaat ggtcccttct ccaatgtctt    33240
ttggagtctt gatgactttt tgaattcttc atttattttg gcttttatc aaggagtcct     33300 aggctggaga aaatctttag agttatttta cttagaccct aatctcaaca taatatctca    33360
gttaaatcat tctgcacttt agtaaagaca tccaaggaag ggagttcctt ccttaagcag    33420
cacattctaa agttaaaaac ttttcaggaa attttattat gtaactgatc taatatttta    33480
tttggaatta ctatgtagat ccccaatgtt ttaccttctg tgtagtcttt tcccactgtg    33540
cccaccctcc actgtacatc tgcgctccat ctagtggttt gtaggatatt ggctgcattt    33600
tgtcttctgt tccatgccct atctatctct gtgtgtgtgg cgtgtatgtg tgtgtggcgt    33660
gtatgtgtgt gtggcgtgta tgtgtgtgtg gcgtgtatgt gtgtgtggcg tgtatgtgtg    33720
tgtggcgtgt atgtgtgtgt ggcgtgtatg tgtgtgtggc gtgtatgtgt gtgtggcgtg    33780
tatgtgtgtg tggcgtgtat gtgtgtgtgg cgtgtatgtg tgtgtggcgt gtatgtgtgt    33840
gtggcgtgta tgtgtgtgtg tgttcctta tctaaaaagc aacttattt tctttgcttc      33900 caacttggaa atagggaatc tttctttcat tgatatgatt atagtacact gataatgcta    33960
agaaatagag aagttgcccc aattcttaac tgtgtttctc cacatcattt gagaagctgt    34020
gtatgtgaat gtgcatgagg gctctgtaag agagagggca agttccaggg atgagcgtgt    34080
tcatcagcag ggctgatagt cttgaggttc agtgggagag ctaaggcaca tggttgttat    34140
ttgttctctt ctatttcaca taatgtgtgc ggtttcaatt gcagttaatg gagagtggct    34200
tgttgtgata attaaggctt attagttaat ggtgtgttta gcattacagg ccggcctgag    34260
cagcaatcat gtgtcccatg gggaagttct gcggaaagtg gagagggtt cacggattgt      34320 cactgttgtg ccccaggaca caaagcttgt attacaggta agctggtttt tcagacaaga    34380
tagatagtct gattgtcatt cagccaagta ccaagcataa ttcttgcagg ttgtatttta    34440
ggctttctta ttctttgtat cgtttattgt aaacctttcc ttgatagttt tctgttagct    34500
ttattcaaag gagtgttgat acaggctgtg accataaggc tcaaagcgaa acttttcttg    34560
aaagtcaaga taaatataga gaacaacaag attctgctaa aagtgtgctg attttagaga    34620
gttgtggtaa ttctctgtga agagttaggt aaaatggtgt atcctggcta tttaaatgtt    34680
ttctacttaa ttaaaaatgt tactgcttta atttatttaa gatgccaagg ggaaacttag    34740
aagttgttca tcatcgagcc ctggttttag ctcagattcg gaagtggttg gacaagtaag    34800
tgccattgta ctgtttgcga ctagttagct tgtgatttat gtgtgaagac aataagtatt    34860
ttattacaat ttcgagaact taaaattatg aaaagccctc attacctata tcatcaatca    34920
gattcttaga ggctctttt tttttttta acttttttac tttaatgcag tattttgtag       34980
tggagattcc tagcagaaag aatcgtgaca ctcatcatat aaaggagggc ttctcttaac    35040
ctgagggaac acatgtgggt tttaggtggc ctgtgaaccc agggagattg tacacaccaa    35100
accttgtctt tgtgtatttta ttcaagtaga aagcccacag ctttcaatag atttacagcg    35160
gggcctatga cccagaaaag cctgagctac tcttgtgaag gaaatgactg attttctgaa    35220
cctatttgga ggaaactttg tattggaaag atctatacta atgttttgtt taaaaagtag    35280
```

```
acctgaattc catgatgatt ttctttgttt ttttttttgag acagagtctt gctctgtcac   35340
ccaggctgga gtacagtggc gcaatctcgg cttactgcaa cctctgcctt ctgggttcaa   35400
gcaatcctcc cacttcagcc tcccgcatag ctaggattac aggtgtgcac cacgcctggc   35460
taatttttt ttttgtattt tcagtagaga cagggtttca ccatgttggc caggctggtc   35520
tcaaactcct gacctcaagt gttctgccca cctcggcctc ccaaagtgct aggattacag   35580
gtgtgaacca ccgtgcccgg gcttctgtaa tgattttctg ttgtatgtat gtgaagatgt   35640
agttctcaga cagtcatgat gactaaatta ccctttttaa gaaggtaaat gaatgtggta   35700
cctgattttt ttattctgta atttcagagt agaaatccag tgatagcagc ttggcattgg   35760
ggctgtaatc tgattataac tggtttgtat cataatgaaa atatgctggg cccatggagc   35820
tcagttttg tgaatatctt ttctattctt tctctgtctt ctcacagact tatgtttaaa   35880
gaggcatttg aatgcatgag aaagctgaga atcaatctca atctgattta tgatcataac   35940
cctaaggtaa ctttctaagc tgtcatttac tctagcttac tttgtactta aactaatatg   36000
atctgaacga agatgttttg tccttttttt ggtaggtgtt tcttggaaat gtggaaacct   36060
tcattaaaca gatagattct gtgaatcata ttaacttgtt ttttacagaa ttgaagtaag   36120
tattttgaat aattcatgtg tatctttcc atagtttct ctcttcttgt taaggaaatc   36180
aagcataaat agctagagaa gaaaaattcc ttactgttca ttttttaaaaa ttgctataac   36240
tcttagatgc cagttggttt tttgctcttt tccgttcttt ttaaaacagc ctgtttaaaa   36300
ctatgtcctt aaaacatgtc attcagaatt attatttcac ttgatttta ggtatacata   36360
taaaactact tgtttttcct aggagactga aatcaaatgg catctttctc tctgatgatc   36420
tttccctca acttttaat gaaacacttt caaaatagag aaaagttgag agaattgtcc   36480
agtaagcaac ctatatatac cccacctgga ttcgccagtt tatattttc tgtatacaca   36540
ttctcattct ctataatctg tccatccatc attcatcttg tttgtagaca aattgctaag   36600
tgagttgtag acatcagtcc actctaccac ctgtacttct ccttgtatat cattaactag   36660
agggcattct ttgtgtatgg gttggttttg ttgtgttttt tcaggtcata tttatctaca   36720
gtgaaatgtc caaatcttaa gtgtgccact tagtgagttt tggcaaatgt acacttcatg   36780
taacctgaac ctctgtcaag ttagagggca tttactcctt ttcagaaagc tgcttcagat   36840
tccttcaat cagtccctgt cccattcccc aggcaactac tcttctgaat ttttaccat   36900
aaatcagttt tgcctgttca agaacttcac ctaaatggaa gcatacagta ttactcttct   36960
gcataaagct gttttcattc agcatattgt cttgagattc atctgtgttt ttatatgtat   37020
cactagttca ttcttttttt attggtcagt agtatgccgt tgtgtaaata caccactatt   37080
tgcttattca ttccctgtt gctggacatg tggattgtac tacctgttt ggggctaatg   37140
tgactaaaac atctacaaac atttgtataa gtcttttgtg gacatgtttt atttctcaat   37200
atttttataa ttcaactctt ttccaaaagt catttttatt tatcatcatc agcatgccag   37260
gtgtatgtta gtaatttgat cgctgggcta catgttctgt tgatgaccat tccatacaca   37320
cctgttctta gagaagaaga tgtcacgaag accatgtacc ctgcaccagt taccagcagt   37380
gtctacctgt ccagggatcc tgacgggaat aaaatagacc ttgtctgcga tgctatgaga   37440
gcagtcatgg agagcataaa tcctcataag tatgtatgct gtcaccaggt ggcatccttt   37500
gaaaaaccga agtgtgtagt tgtccttgtc cagcctactt acctttctca ttctggtgtt   37560
cttcacttat tacctcagat actgcctatc catacttaca tctcatgtaa agaagacaac   37620
```

```
cccagaactg gaaattgtac tgcaaaaagt acacgagctt caaggtagag atccgctcac   37680
agagaaagtg cttaaggtgg ccgtgactgc tactagtctt ctgcaggtga caatcaccat   37740
gtcattgcca caccacagat ttaacatgtg acttttagt tgccattta agacccttgt    37800 cagttttttt cagtgctgcc ctctaaagca tatataaaag tatcagaagt atatattctt   37860
ctgatgtcca gttctattga gaaaaattta ttgtctttt ggttatgttg ttaggtctgt   37920 ggatttttc cccaaatgat tgtgttctgt tttgtttct aaacactgtt aggaaatgct    37980
ccctctgatc ctgatgctgt gagtgctgaa gaggccttga aatatttgct gcatctggta   38040
gatgttaatg aattatatga tcattctctt ggcacctatg actttgattt ggtcctcatg   38100
gtagctgaga agtcacagaa ggtatgtgga gttcttactt ttatgccatt tggttcttgt   38160
ttatataatg atagtgtgaa accctgcttc tggtagtgca gtagctttc tgctatcact   38220 ctgtgagtgc agggctggag acagatctgt gagtttctag ggcccacatt cctaagcccc   38280
tgtgcttatg aaagtgtttt gattgtgagg ttgaagaagt gaagtaaaat tgcatggctt   38340
ttttttgttt cttttttttt gagacggagt ctcactcagt cgcccaggct ggagtgcagt   38400
ggtgcgatct cggcttactg caagttccac ctcccgtgtt cacgccattc tcctgcctca   38460
gcctctctag tagctgggac tacaggtgcc catcaccacg cccggctaat tttttgtatt   38520
tttagtagag acagggtttc actgtgttag ccaggatggt ctccatctcc tgacctcgtg   38580
atccgcctac ctcagtctcc caaagtgctg gaattacagg tgtgggccac catgtgcggc   38640
ctaaaattac atggttattt ttaagatgat gggcatatgt gtgagctaat ttcttctctt   38700 ataaggaaa tgtaacaagt ggttcatgtt ccactccggt tctttctcac atggctcttt   38760
tttctagtgg agggtgggca catggagcac agaaggctca tggcctcctt tcctatgttg   38820
gtacatttgc tatgatcaaa aactttgaac accactggta tgcatatttt ttatttattt   38880
ttttgcagcc tcagtctctt ccccatgacc tctccaaaaa tgaaaatcgg atccttcatc   38940
tctctgctta aaatacttca tgagctccca ttgttccgag gatataattc agaagccata   39000
atactgctta aaaacccttc cttgacctgg cctctgtgta tctttccatt ctcacttctt   39060
ggtattgtct tttttcctc tgcccatgga ggaaagacaa tgcttttgtc cccttccct    39120 tgcccctcac caccacatgc cttggtgggc agcattactt ctgccatcca tgggctttga   39180
ctgcttccac cctcaccatt ccctggcta attctcacta atctaggtta aaggatgcca   39240
aggtggcctc ttcccagtaa gccattcatg cttccctcca gggactgggt gaggtgaccc   39300
tcctatatgc ttctgttgca cacagtgcct accectgcag actacagtgt gtctttatct   39360
agagtgcggt atttatttat ttatttttga dacaaggtcg ggctctatca cccgggctgg   39420
agtgcagtgg caccatcttg gctcactgca acctacgcct cctaggctca agcaatctca   39480
cctcagctta caggcgtgca ccaccatgcc cggctaagtt ttgaattttt tttgttgaga   39540
cggggtttcg ccatgttgcc caggctggtc tcaaacttgt gagctgaagc aatccatctg   39600
cctcggcctc ccagagtgct gggaatgagc acttaattat ttgttgtctt gggttttctt   39660
cctatgttgt tcttacatgt atttatcctg tcagcccagg gaaattgcat taaaaacagg   39720
aaacacctct ccattaggaa gaaaaacaat ttgcttacag gcatggcat agagctggag   39780 atgatagtgc caataaatac taggttggca gggtctcaga gttttgtgtc caactcagta   39840
taattttatg tttgttttaa tgtgatcatt tcaggagagc atggaatgtc atgaaaacag   39900
caccaagagc aatgtcttag acttttagga gaaacttaga tgcatttgtt gaatatcttc   39960
tagactgaaa ccttatttcc cttattagcc tatgaaataa atgatactgt gagacttagt   40020
```

```
taaggaagtt actattattc caagtgtaac ttattaatat ccgtatgtga aagcattttt    40080
gccaaagctt gtttgatgtt cagctgaccc ttgcacaacg tgagtttcaa ctgtgcgagt    40140
ttgaactgtg tgggtttatc taaatgtgga tctctctcaa acacagttgg ccctttgtgt    40200
ccacggcttc tgcatccaca atcagtgtgg atcaaaagta caatatttgc aggatttgaa    40260
acttgcagat acagagggcc aacattttgt gtatccaggc tccatggggt caaatgtagg    40320
actggggtat gcttggattt tggtatcctt ggggtgtcct ggaaccaatt ccccatagat    40380 actggggac aactgtagtt tgattttata tattatataa tatgcagtta atatataata     40440
cacatttaaa aattatgtag ctttgggttt attgctatat gtaaatgcta gtttctattc    40500
ctatatatga atatcacaag taataaagtt ctcattaatc attttttag  gatcccaaag    40560 aatatcttcc atttcttaat acacttaaga aaatggaaac taattatcag cggtttacta    40620
tagacaaata cttgaaacga tatgaaaaag ccattggcca cctcagcaaa tgtggtaagt    40680
gtggggatta gtatgtttat ctctacttca gatcttcttt ggaactaggc aaggtataaa    40740
ttaaactgtt agtttagaca gtgactgatt tcacttccca ctcctgaaaa ctctaacaat    40800
tatgtatgct cacgttattt tgtcctgtgt tctgaaaagc tgaaggtaat cactttaat    40860 gaactggagg agctccctag gtaagaacgt caagtagatc cttttttggt taagaatgag    40920
cacctgtgaa gttaacttca gtgtctcaga atcaaaattg gttgtcagtt cttccttctc    40980
atgctgtttg cagacatgtc agggaaactc tgcttgtctg gagagagtga tgaggccacc    41040
tccccgtgcc ctgcaagacg cagtttaat  tgacagtgat ggggtgccag ttgttcttcc    41100
catgctggaa cagttgtgat tctttactga ggactgatgg gggaaggaa  gaatcacctg    41160 gggtgcatgt taagccttca gctgctggca tccttggaga atctgattca ggtggtctgg    41220
gataggactg aggcgtgcat gtgtctaata agcttcccag gtgatgtctt ttcaaggagg    41280
ctgagaaaac actgggctgg aaagctggga ctcttaagta ggatgctgat cccaatcagt    41340
gctgctcttg cctcagaatc tgcagtggtg ctcattaaaa attcaaattc caggatccca    41400
ttcttcagat tctctgatta tttaggtctt aaaaagttcc tcatttattt tgtttggtga    41460
ccattggtat aaatgaagtc cattatgctt cccatgtctt aagcctgtct ttgtgtgaat    41520 cttttttcctg caggacctga gtacttccca gaatgcttaa acttgataaa agataaaaac    41580
ttgtataacg aagctctgaa gttatattca ccaagctcac aacagtacca ggtatgtggt    41640
atgtgaaaat gaggctctcc tggttttgct ttttgcttta gtaggaaagg agtgaggatc    41700
ctaagttcat aacaccatcc ttggcttcaa aatttatctt aaaactaatt agcctcaatt    41760
tgaacttctt atctgggaga atggtcctga cctgttctct gattcctcat ctggaatacc    41820
acagcacctt cctcgtgggg ttccctgctt ctttcccacc cctcctctag cccaacctta    41880
ctgctgtaag tctgattatc ctaacaagta cagatctttc ccatatattt cagcataaag    41940
ggaaattttt gtttgcttga aaaagcatcc ctttagcttt ttttatatac cacacactt     42000 gcttctaagt taaatgtgtt atatgatcct cttaacagcc tcatagggtg ctgtacacaa    42060
tttgtagatg aggaagcaac ttgcctgagg atccagagct acaaagtgct ggacctggga    42120
tacagagccc aggctgcctg accaccctgc ccatgccatt aaccaccact ctaccatgcc    42180
accagcatca ccattttcag tttgtcctca gacaatatac acatctttct ttgatcaagc    42240
ccctgccagc ttcttagca  ccagcttctg ccactgtcca cattcccagt tacttgtagg    42300
tagttctaca gatgtcacat cgtgtgattc ctctgtcatt tctctaccca ccagccttcc    42360
```

```
tttagcccca tttgtccatc agaacccttg ggttactcct gaatgccatt cctggaccag    42420
gcgccaaaca ctgagccccc agagcagcct gccctcgcct tggtgattgc atttgtcaaa    42480
ctgctgatta gctggtttgt cgcctccacc aggctgtggg ctccttaagg gcagggactc    42540
catgttgtat tcctctctga atctctggct aacatccagc ctggagaatc gaggatttgg    42600
ccagtggcta cctctttgcc cttgttttct gttctcttcc acactctctc tgctctagtc    42660
acactggccg tcctgttact cctcagacct gctatacaca ttcctgctgc atggccatgg    42720
tgccttctct gccctctgcc tggtgccccc tatctcatca cgtggtttat tctcctgaca    42780
gccattagag ctcacactcc ctgagagctg caaggagact gtcctctgtc cctttactca    42840
cgtttgccat tatgctatag actatatttt gtccctaagt ccatcctctg ttactataag    42900
agcagcaact tggtggtggt tcttatatgg ttttttcattt gtttggtttt attttttgcc    42960
ttgctgtagt atccatactg cccagaatgg tgcatatgta gttaagagta attatttgtt    43020
gagtgaataa atggcacatc ctcagtaagg ttttgaatga aaaatgact gtactaactg    43080 atcaactgta agattttccc aggtaattct ttcaaggggg ttccaagtat aggaactaag    43140
gcagctacac tggagcttta gagaaatgat tgtcatattt cctcctcagt cctaaatctc    43200
ctcttgtcac aggatatcag cattgcttat ggggagcacc tgatgcagga gcacatgtat    43260
gagccagcgg ggctcatgtt tgcccgttgc ggtgcccacg agaaagctct ctcagccttt    43320
ctgacatgtg gcaactggaa gcaagccctc tgtgtggcag cccagcttaa ctttaccaaa    43380
gaccagctgg tgggcctcgg cagaactctg gcaggtaagt acaatcattt atatgtttac    43440
atctacaaag gttttaaaaa atttatttct tttgtttggt aattttgcaa ataaatttag    43500
ggcagaatac tctgagacag tcttgttctc actgataaaa attaatttag aatgctttaa    43560
aggataagct actacagcaa gagtcccaga atgcagtggc ccaatatgga aagaagttta    43620
tttctctctc ccatagggat ttataggccc ttccgttgtg tggctctgca accttttagg    43680
cagatggttg tagctgggtt atctccacag ctgtggggaa ggaaggagag tggggagaag    43740
ttagaatcat ggtaaaacat ttacctttaa gttggaaatg acctggatgg aagttaaact    43800
atcaccttct attccatctc ggccacgcca tgtagctgga tgggctgtgc cctgtaagaa    43860
ggtaaagatg aattttttgga tgggtccatt ctgttataga cagtaggttg ttggaatagc    43920
caggaatgag gtggggaaaa taaaaggcca aatgtcgaag cattctgaaa gcaaaggcag    43980
tttagctgcg tcagggacaa gggttgcccg aaccagaggc gaggctggta ccaggggctc    44040
tagtaccaga gtggaggaaa gggtaaggac acctatgaaa agagatgagc agaagctctg    44100
gtcatctcag cagtgcttga agtaaagcaa tgactggtat attttttttcc ctaacttgta    44160 aatattgttg agatctcaaa gaaaaaaata aaaagcagtc ctaaaaaaat tccaaactct    44220
atcctgttaa attttgttaa atttatgtac cagtccttct ttgtcatttg cagtattctt    44280 ttttcttgg gattatacca gtgtatggga ttatacttt tctttttctg gttattagcc    44340
tttcccaaat ccctccgttt ccatgctggc ctcttttttac aaatgtcgag aattccttat    44400
ttcaggcctt ttagttattc gttcggtctc cattgttcct ttctgcttta gaaatttatg    44460
atattggttt tttataccttt ctatctctgt tcttggatct cttctattct ttacagctct    44520
tagcttgcta tttcccatgt cttatgaggg agtatttcta gttttttctca gatgtttagc    44580 aaaagtaggt ggggagggca gtggtcaaag atgtttgaga atgttacac actggagtca    44640 ctctgtgtgt acatttaacg taggcagttt acacaagaga gcaaaagaaa ggtaactatt    44700
taaatagtgg aggtgatttt acctactttt tttagtgata tatgcactgg agtgagcatg    44760
```

```
caatgagaga ccggaatcta ccagctcctt cgaaagcctt gggttctctg tgcctctcat  44820
tgtggtttat ctcaattggg ctgagagtga ttctaggatc taaagacact gcatgactca  44880
aacataagtc agctacctcc atctagtgct caaccaaaga aatagtggtc tcttactgtt  44940
aagggacgaa gtggtttagt gagagatacc aggtcatttt cccatataca tgctttggaa  45000
gcatctttca aggctaattt tggctgtata tgattttcaa ttcctgtgct aaatttagat  45060
tctagctgcc atttaagata ggactctgtg gtgtatatac ctattccctc acagaaattc  45120
agaaagtaca tagtttcata cataataaag acatattaaa gaagcacttg agctaaagta  45180
tctgtttaac tttgtagtca actgctgctt attgtctcta caggaaagct ggttgagcag  45240
aggaagcaca ttgatgcggc catggttttg gaagagtgtg cccaggtaaa ctcaattcct  45300
cccttctaaa ccccccagtc agcaagaaag gtcttctcaa ttgtatctta gtgatcatga  45360
aagttaaagg aactgtgcat aattgttaag tccagagata gtgtttgccc cagaggtctt  45420
atcttgctgg cttgacttgg aaatctaaat ttagtacatc tctaagtttg gtgaggtaga  45480
atatgaaggt gctctacttt aacataccac tggtttgacc ttggtagaaa gtacttaatt  45540
acatctcaag gtagctgtgc ttttaaaat tgagtttgcc aaagtagaaa caatgagaaa  45600
ggaccattat aaaacaggat cattgaaggc tacatactct tggcttttac tctcattctc  45660
cctattggaa atgtctcttt tacctcaggg acctggaggt acagcagatt ataaggataa  45720
gtacccatat gagcatttgg tagtattata ggatttatta tgaaaataat aaaactgcag  45780
taacactggc cacagactaa cagtacacag gtgcacagtt gacaccaggg attattgcct  45840
tgtagagttt tgacctttga tgagagagtg ttttttacag ttgttactga tagcacattt  45900
atgtaactta attgtgcttt aaaaatattt aattgtctct tgtgtaataa cagtaagtga  45960
aagacgataa ctaaaatttt atataattag atcctggaga gaatatttgt tgggtgattg  46020
aattgaaaat accagtgaat gaaacatacc taaaagggta gataggttgg gttggaaaga  46080
tataccacat cgagggttaa ttaaatggat aagatgtcat tatctttttt tctttgtaaa  46140
ggaagattaa tgcataaaat tattttgtgt aatttacata caataaaatt atgtgttgta  46200
cagttgtata atttacatat aataaagcta attcaccaat tttagatgaa gaattcagta  46260
catttggaca tatgtttgta gctgtgtaac caccattgca ctcatgatct agaacatttc  46320
taacaccccc aaaagttccc tacttcccct tttgcagtca gccttctccc tccactgcca  46380
gcctttggca aactgatcag tcagtaaagt ttcacattat ctagaatttc atataaacag  46440
aaccatatgg tatgtagtct ttttaatctg gctcctttca ctcacatagt gcattggaga  46500
tgcatccatg ttgtagttta ttcctttgta ttgctgaata gtatcccatt atatgtatat  46560
gtcagaattt gttgatttac cagttgatgt acatttggat tgttttcagt ttggggttat  46620
tatgaataac gcagccatga acattctagt gcaggtcttt atggggacag gagtaggaat  46680
gccacatccc gtggtaagtg gatgtttaac tttttaggaa gctgcagaac taatctgcag  46740
tggccgtatc attttgcatt cccctcagtg atatgtgaga gtgcttcagt gactcctata  46800
ctcaccaaca ctgggtgtat tactgtgaca ctagatgtat tatctattgc tacgtaacaa  46860
cttaccttaa aagctggcag cttaaaacaa cagaccctat tatcccactt tttcaatggg  46920
ccaagaatct tggctgggct tagctggggc ctctggctca gggtccttta caaggctgca  46980
attaaggtat tggccagggc tagagtcatc tcaaggcttg actagttttt aatttcattt  47040
tctaatgttt tattactagt atatagaaat atagctgaag tgttttgcag ggaggctgta  47100
```

```
taattgacct tgtatcctgc aaccttgcta aactcattta ttagttctag aagctcttgg    47160
gtgtattctc taggattttc tacatcaaca aacatggttt ctataaatat agttttatgt    47220
ctttcttaca atcaatactt ttttctatct gtattgcatt ttctagggct tccagtgtgg    47280
tgttgaatag aagtgttaag agtgaacatc cttgccrttt tcctgatatt ggagaaaatt    47340
cacttgtctt ttagcattaa gtgtcatgtt tgcttttta aaattttatt ctatattatt    47400
ttatttttga gacagagtct tgctctgtca cccaggctgg agtgcagtgg tgtgatctca    47460
gctcactaca accttgacct cctaggctca agcgatcctc ccacctcagc tcctgagta    47520 gctgggactg caggaacatg ccaccatgcc tggctaattt ttgtattttt tgtagggatg    47580
gggttttgcc atgttgccca ggctggtctt gaactgttgg attcaagcaa ttcgcctgtc    47640
tcagcctccc aaagtgctgg gattacaggc atgagcctcc gtgcctgcc tgatatttgc    47700 ttttttttt ttttttaatg ctctctattg cagagttggc aaactacaac ctgtgacaaa    47760
tccagcatgc cacctgtttt tgtaaataaa gctttattgg agcatagcca tgctcattag    47820
tttacatctt gtgtatggct gctttaacac tacagcagca gagttagagt tgtgacacag    47880
atagtttggc ccataaggcc tatatttact gtctaatctt ttacaggaaa aatttgccaa    47940
ttcctgccct cttggtttga ggaaattccc ttctgttcct tgttctgaga gtttgtatca    48000
tgaatgggtg ttaaatttg tcaaatgcat tttcaactat gaagggtttt gtttttagac    48060
gagtgatatg ggggactagg tgattgattt tctactgtta aaccaaccrt gcatctctgg    48120
gttcaacccc acttggtatt atagatttat tacccttttt ctcttgtggc agattagatc    48180
tactaaaatt ttcttgagga ttttttgtgtt tgtgttcatg agggatattg tagttttttc    48240
gtgtctttgc catgttttgg gtatcaggat aatgctgctg tcattgaggg gtgacaaaaa    48300
tgaggggtgg tgtcctttac acttctgttt tctggaggat ttcatgtaga attggtatga    48360
gagtctagct tatggttaaa aacctatgtg tgatgtttca gacctgacca taaacaatta    48420
cagactttac ctaggaggcc acatggggaa aagctgccct ccctacacca gacttggcgt    48480
actgccaatg cattacagtt tctaaaggga gttgcagtca aggactcagg gcccctgtt    48540 agtcatgctc ttgtaacagt atttgcattg agagtcctgg cactttcatt cttaggtctc    48600
tctatctgag gccatgggcc aaggtcttct tcaggcacct ctgccaaggc ctgtttatgc    48660
aagaaggagt ggaaaaacct tgacattttt ttccactgtg actcactacc cagtactttt    48720
ccacccttag ccccttcct ttgcacccat accccaaga tccatcaaac tgctaaagcc    48780
ttttttccca agctccttca acagtgaacc aaccctcatg tctgtgtgga tccagctgac    48840
tcttgactag tgagttgttc cttgggaaaa aatggaacag agagagttgg tgctttccct    48900
ggttttagcc tcttgcttat accaatgcaa tgcctgaagg cttaattcat ttttgacttg    48960
ttgctttgat cagctactcc aacacctgac agctcagctc tttctcccag ctcttgggag    49020 atatttttt ctttaaatgt ttagtagaat ataccagtaa ggccatctcg gccaggagtt    49080
ttctttaatg aaagcttttc cactattagt tcagttactt tagtagacat tagcctattc    49140
aagtttatct gtgtcttctg gaatgagcat tggtagttta tgtctttcaa gtaatttgtt    49200
catttcatct aaattgtcag atttattggt atgaagtgtt tatagtattc tcttattta    49260 ctgtccgtag ggtctatggt gatgtcctgt ctttcattct agatattgat gtgtcttctt    49320
ttttctgatt attctggcca gaggtttatc aatttattg atcttattaa agaatgaact    49380
gtttcattgt ttttctctat gatttttctg tattctatat cattcttttt ttattatttt    49440
attattttat ttgctctttta ttttttctagt ttcttaaggt gatggcttac tttttttt    49500
```

```
ttcttatttt tttcttttgt tgttgttgtt tttttaaaga aacagggtcc cactcttgct   49560
caggctggag tgcagtggca cgatcatggt tcactgcagt ctcaaactcc tacattcaag   49620
ctgtcctccc ccctcagcct ccagagtagt tgggattaca ggtgcatgcc accatgcctg   49680 gctaatttt  aattttttt  gtagagatgg ggtgttacta gttgcccacg ctggtctgaa   49740
actcctggcc tcaagtgatc cctccacctc tgcctcccaa agtgctggga ttccatgtgt   49800
aagccactgt gcctgaccaa ggtgatggct taaagctatt gatttgagat gattccttac   49860
tttatagttt aagcatataa tgccataatt ttcctcaagc accgttttag ttatgttata   49920
caaattttga aatgttttgt tttcatttcc taatttccct tgtgatttct ttattgaacc   49980
ttggcttatt tagaagtatg tttaacttgc agatattgga gatttgccag ccatcttttt   50040
gttattaatt tctactttaa ttttgttgtg attagagaac atacatttta ttaatttaaa   50100
tttataattt attttaattt ataatatggt ctgttttaca gaatgttgtg tgtgtatttg   50160
aaaataatat gaaagctact attattggat ggagtgttct ataaatgtca gttagattag   50220
gttgatcatg ctgttctagc ttttatatc  cttattgatt tcctcactac ttgctctatc   50280
aatgactggg aaagtgttga agtctcccag tatttgtcta tttctccttt gattctacca   50340
gtgtttgctt aatgtatttt gaagctctgt tataggtgca tacatgttta tgagtatgtt   50400
atagatgtat tcattttgat atccttcttt ctctgttact attcctaatt ctgaatttga   50460
ctttaatgtt attaatataa ttcttccagc tttctcttgg ttagtctttt cattgcatat   50520 cttttctat cctttactt  ttaatctagc tgaatgtagt ctttattttg aaagtgcgtt   50580
ccttgttgat agcattattg gttctttttt ttttttaaat ctaatttgac aatctctgtc   50640
ttttaattgg agggtttaga catttgcatt gaatgtgatt accaatatag ttagatttaa   50700
acctacagtc ttgctgtttg cttttttgttt gtttcattga tcctttgttt cttgttttt   50760 tcttttttg ctttccttg gatttagtat ttttcataat tccatttac ctccactgtt   50820 ggcttattag ctatacttct tcatttcagt attttagtgg ttgctgtagg atttataata   50880
aatatcatta actgaccata tcttcagata atcgtatact acttcatata tagtgtaaaa   50940
accttacaag agtattcact ccataatact ttgttattgc ttttgcttta agtgatcaat   51000
gattgtttaa ggaaattttt taatgacctt tcatgtttat tcttttttt  ttttccaaa   51060 agattcagta ttttccgagt tttcaaaaac tgctggccac tcaaagtgga tcaacaaaaa   51120
tttaagagct aaaactgtaa aactcttgaa ggctgggcac agaggttcat gcctgtgatt   51180
ccagcacttt gagaagctga ggtgggacaa tcacttgagc ccaggggttt gagaccagcc   51240
tgggtaacat agaagacct  tgtttctaca aaaataaaa  acacaattag ccaggcatgg   51300
cggtgtgcac ctgtagtccc aacttcttgg gaggccaagg tggcaggatt tcctgagcct   51360
gtaagtttga gactgcagtg agctgagttc acgccactgc acttcagcct ggacaacaga   51420
acaagaccct gtctcaaaac cagaacgaaa ctataaaact cttagaagaa acagggcta   51480 aatcttcatg actttggatt tggcaatgga tggttagaat taataccaaa aacacaatca   51540
ataaattgat aaaattggatt taataaaaat taagaacttt tgtgtatcaa ggacattgtc   51600
aagaatgtga aaagacagca tatagaatgg aagaagatat ttgcaaatcc tatatctgat   51660
aaaggtttaa tatccagaat atgtaaggaa ctcctgcagc tcaacaacag aaagccagtt   51720
aaatcaattt tgaaatgagc aaacgcctgt aaacccagct gcttggcaga ttgagacagg   51780
aggattgctt gaggctagga gttcaagacc aacctggaca acatagtgag accctgtcta   51840
```

```
aaaacatttt tttaattagc tgggtgtggt ggcatattcc tgtagtccca gctacatggg   51900
agaccgaggc aggaggatca cttggggcca ggcagtcaag gctgccgtga gctgtgatta   51960
tgccactgca tcccagcctg ggcgacagag tgagaccctg tctgagaaaa aaaaaaaaa    52020 aagaacaaaa aaaaatttag aagattgcta ttctagtcta ctattttttc aaagggtggt   52080
cttgttaaca attctggagc ccacctaaac ctgctaaatc aaacttggta gtaaagctgg   52140
ggagatgggc atgtctaaca gacgtttctg gtggttttga tgtccaggcg tgcagagaga   52200
tgatgcttac cttgtgtttt gtcattattt tcaggattta caccccttcc ttgtcttttg   52260
tatcaatatt tatggagtca tgaactctag gataggcatg atgttgagaa ctaggagttc   52320 tccctggcc agggagatag aggcaggtct gtggttagtt ttgtagttgg ctgtgatgac    52380
atctgacatg ctctcttcac ttgttgtctt cttcctgttc ccttgtcagg attatgaaga   52440
agctgtgctc ttgctgttag aaggagctgc ctgggaagaa gctttgaggc tggtaagaat   52500
cttgtaaatc ctctggatgt tgggtgctaa gcagagagag caagcaaggg attccaggtc   52560
agttggaatc tcttgtcttc tgaggttcat gaaataagta gaaataggtc aggttcctgg   52620
cttaaggaaa agcggtgttt ttaaaatcat ttttatcatt cttgataata atttgaaata   52680
ttactgtctt ttactgaaat gaattgaatt tccttggctg cctgtagga ggcctgtttt    52740 tcaggaaaat attctgatta cctctgaaag taatccatgt cttttctaagt atcttaactc  52800 tccagtgact agaagttttc cttcctaaaa ttattgtgtt tttccttcta ggtatacaaa   52860
tataacagac tggatattat agaaaccaac gtaaagcctt ccattttaga aggtgagggt   52920
tccattttag atagaattcc tcatttggaa gaaggtgagg agagagagat gagagagtct   52980
cctcctattt actgtgtttt cttaataata tgtcatgtag actcaatcaa aattaccacc   53040
tggatataat atttaattct cactagaatt ttaaaatatg ctgaactatt aaatggtaac   53100
aaaatattta aatgttagaa acctgtgatc aaatatgatt aagaatcttt gtatttggaa   53160
atagtaaact tgaatatgaa ctatattaga taataatata acactgataa atttctggca   53220
tttaataatc atgttgtggt tatataagat aatatcctat tattctcaag agataaatgc   53280
tgaaatattt aggaatgaag gatcatatct ctgccttact cttaaaaggt tccacaaaag   53340
tattaatgaa tgtgtgtatg catgcagaga aacaggaagc aaaaaaatgt caaaatgtta   53400
gtaattggta aatcaaagta aagggtatat gtgtgttcat tgaactctta caacttttat   53460
gtaggtttca acgtttcaaa gtatttttta aaagttacct tttcaaatga agtttgtggt   53520
tcttagagaa catatgaata ttaccagttc tagaatactc agatggtcac tgtgacctct   53580
taaaagcaaa gtggagaagg acatcagttt gacttataga aaccttaggg agtggttgat   53640
tttaagttct gcatttttat gcacatctac cctgtaagta acgtctggcc tttctgacat   53700
ttacatgtat gcacattctt accttgtctg caccccttc ctccatccta attaaaacgt    53760
tgctggggta cttttatgt cattcacttt aggtacctct aactgggtac tgaaaacatc    53820
attcctcatc tataataatc taaccagctc ttacttagat tttcaccact aatgagaacc   53880
tttcttagat aaatgccgat aattcatcta cataggccca aaacctatta ataaaatgca   53940
tccttggata gtagtatttt gctttttaa aatgtattct actagtgtta ttttctctct    54000
gtgtattttt ccattggaca atatttatta gatacatttt ttccacatcc atgggcattt   54060
tgatggatgt ttagccagaa acatttaggt aattttcttc ttattttgt taactgagct    54120 ccctcccct accccccctt tttttgtttg tttgttttgt ttgttgttt gttttgccaa     54180 tcctcccttg ctttaggtat caagtcttcg ttcaggtgat tttacaagtt cagtggtagc   54240
```

```
gcatattctg ggataatgtt gatgaactct aagatctgga atctcagtct ctaatttgtt    54300
aatgcttatt aaggaaaaag agctcgcttg gaaaacctag taacctcttt cttttttgctg   54360 aattttaacc ctccttcact gctccccgcc tttagttttt tctctttgct taaacctcat    54420
gctcaaacta ttttccattc tgcatctcca gcccagaaaa attatatggc atttctggac    54480
tctcagacag ccacattcag tcgccacaag aaacgtttat tggtagttcg agagctcaag    54540
gagcaagccc agcaggcagg tctgggtgag tatctgcgtg aaggccatcg acgtgcgggg    54600
gcagtggggt tgggtaacgc cacacattgt ctagattgct tggtgatccg cctgcaatct    54660
gattactgtg ccatgggcaa gtgtgaggct tctgtggagc ccttcaggg ccctctgtgt     54720 ctgtgtttgt gtgttggtga agggcaggac caagcatgaa tggggagagc tctgccagac    54780
attcccacct acccccattc acccagagca gctgaccact tccgtgtcta acaaaatgag    54840
tttcctcatt tccagaaaaa agttcaggaa actactgatt tacattagta attactgtat    54900
ttaatattat ctcattcatt ttgagatcaa ctttgcaatc attttcatcc atcctttgat    54960
atgcaccagt tgactctagt tagttcattt accgccctga agtaaaccc acacattagc     55020 aggcagtgtt ttcatcggct tctggttctt cttttctaga tgatgaggta ccccacgggc    55080
aagagtcaga cctcttctct gaaactagca gtgtcgtgag tggcagtgag atgagtggca    55140
aatactccca tagtaactcc aggatatcag cgtacgtatc acattgattc agcacattga    55200
ctatatcctg ggcatatagg gaaagtggaa gcaaatagat tggttttcta ctgggacggt    55260
gtagtgggag tggggagaat attcttcagc gctgtgtgga agttgttcag acactttccc    55320
agcatatctg agacattaaa cttggcattg gaaggttttc ttcctcagcc ttgtggcttg    55380
tgtgttttcc cattcccac gaggcagttc ctcccctgaa tgctcagttt atattaacat     55440
ctgattttat ttttttgaaca aatgttgtga ctaaattata ggcactgaaa aaatgaaaag   55500
ataagcttct tcaattcaaa atcaggattg gaagagacca taaatgtaaa ataagtcata    55560
acacttttac caaatatagt aatttgtcag aaatatttat tcagcactca tatggtaggt   55620
gcagtagatg ttaccaaaaa cttataagga gatatgagtt ataagagttt atagtcttgc    55680
ttgggatgtg taaagcaatg caagattata tattcaaact gaattttgct ttaggaattt    55740
aaaatggaga tctgtgaagt tgtgtggggt catcagcaac tgcaagaaag tagccaggca    55800
aggtagcaca tgcctgtagt cctagctact caggaggctt aaaaatatct gtgtaatttc    55860
taacaggaga tcatccaaga atcgccgaaa agcggagcgg aagaagcaca gcctcaaaga    55920
aggcagtccg ctggaggacc tggccctcct ggaggcactg agtgaagtgg tgcagaacac    55980
tgaaaacctg aaaggtatat tctcagtcct gatgatgatt cctgaccaca acaatagtg     56040 aataggcagt acagacaggc agagttcagt aggtgattaa gctaccattt tcccaatttg    56100
aggaaagatg agaacttta gcaggaaggg tcatgtctgc acacattcct gaagcagccc     56160
ttcttagctg gtaactgaga agccttcctc catttggcat ccccctaact gaactgggag    56220
agatgcttag gccaggataa agaattgtgg gacactgctt tctgcgtagg cccccagcg     56280 tgcttgatttt tcttttttgta gtacatgtgt ttaattattc cagcatttgg gaagaaaaaa   56340
gataatgtgg gagaaaggac ctgcagtggg atcatagaaa ttttggctt tggatagaag     56400 ctatgtatga ttctgtcaat ggagctggga ataaacttta ccactctttc aaatttcttc   56460
tctctagatg aagtatacca tattttaaag gtactctttc tctttgagtt tgatgaacaa   56520
ggaagggaat tacagaaggc ctttgaagat acgctgcagt tgatggaaag gtcacttcca    56580
```

```
gaaatttgga ctcttactta ccagcagaat tcagctaccc cggtaagttt tctcagagac   56640
ggtgtgcatt ttttcatca ttttcatggg ttattgtatt cacacaatct ccaagtcaaa   56700
aagttttcct gttcttaaaa cataagatgc catagttaaa ttatcttaga tttatgtgta   56760
agctgtcagt aagatttgat atttgcctgt agagtgacta gtataccttg cataggtta    56820 aatggactgt cattttcctt tctggatgaa gtagctgtca tggagaaaat gggaaagtca   56880
catgattgct cctggccttc aatgaggttg gagtggggag agatggggga agatggggtc   56940
agagacggcc tctcactttc ctttcagaac tcagggatgg gatcaggctt taaagggacc   57000
ccaggcaatt gcttttcctt ttgttttatg aaaaatttga cttgtcactt ctatgttgtt   57060
atgatggact ttgcgggttg tgtttaaggc tgaatcagct ttgtatcgca gaattctagt   57120
atattgtcat ctgtttatta tttataccte tgttcactct cttatacttc aagtctattg   57180
ttaagagttt ttatttggat tcaaaaaggc tggtgtatca gtcaagatct agaaaggaaa   57240
acaaaagcct atctattatt ttatcacaga atttaatata tggatttgtt aaataagtat   57300
tagaggacta aacaaggcaa aagggaaata cagaggaagg acattgagat agtaactgta   57360
ggaagcagct ttaccctcta gctgagggaa caggaggagt tgttgggaat tattagaatt   57420
tagaagcctg gaagtggggc cctgtagagc tggctcttga acctctgaga ggagggtgcc   57480
agccagctaa tcctggcatt tctgagggag ctggttccaa gcgtacagaa gtaaatggaa   57540
actgaaagga acagctgctg ctgggggaaa agccagccgg tcgggccagg tgtggtggtg   57600
gctcacgcct gtaatcccag cactttggga ggccaaggca ggcggatcac ctgaagtcag   57660
gagttcgtga ctaatgtggc caacatggag aagccccgtc tctactaaaa atacaaaatt   57720
acccgggcat ggtggcgcat gcctgtaatc ccagctactc aggaggctga ggcaagagaa   57780
tcgcttgaac ctgggagaca gaggttgtga tgagccaaga tcgtgccatt gtactccaac   57840
ctgggcagca agagcgaatc tccgtttaaa aaaaaaaaa aaaagccag ccaatcacgg     57900 aagaaatcta gaaatctttt gttcatcctc cagctttgta ctcccctct ggtgttcact    57960 gtaggcagga catgatggga agccagcagc aaggaagaat atctttcagg tgcccagccc   58020
cagcaccaca agcagtggat agaagggtgg gttggagctg agagattaca aatcagctca   58080
gtgtttagaa acacatacgc ttatcatgtc ttgatttcct catttagaaa tgggcataag   58140
acttctctgt gtgcttcaat agaatgcttt gaaggttaaa taagagggtg tgtgtaaaag   58200
cactttacaa accgttgaaa taaaagcaac taggaatcag ggccccagaa cttcttgaat   58260
ttattataat aggtatttct tagaagaaat gtgatcatca tcttcaaaac tgtagtactt   58320
ttgaagataa ttgttttgt tttttgagac agggtctcac tctgttgctc aggctggagt    58380
gcagtgatca ccgctcactg cagcatccac cgccccgggc tcaggtgatc ctcccacctc   58440
agcctcttga gtagctggga ctacaggcgc atgccacaac acctggttaa ttttcaaatt   58500
ttctgtagag acagggtgtc accaagttgt ccccgctggt cttgaacaac tcctgggctc   58560
aagtggtctg cccacctcac ctctccaaag tgctgggact ataggcatca gccaccatgc   58620
ccggcttgaa gataataatt tataatacca ctcccatgag tgatcttctc ttctgatcac   58680
atattcacat taaggtctat tttattttat tttttcttg ctctgtcacc caggctagag    58740
tgcagtgaca gtatgatcaa tcatggcttg gtgcagcctc gaatgcctgg gctaaagcag   58800
tcctcccacc gcagtctcct gagtaattgg gaccacaggt gcacaccacc atgcccagct   58860
aattttaaaa ttttttccta gacatgggga gagggagtcc tgctgtgttg cccaagctgg   58920
tcttgaactc ctggcctcaa gtgatcctcc tgccttggcc tcccaaagtg ctgagattac   58980
```

```
aggtgtaagc caccatgcct cccacattaa gttctaagac atcaatttta tgattgtggt    59040
tttgattggt gaagtatggt tgtggtatgt gcaggatacc gtgagtgact tctcatggca    59100
ttgctcttga gagtgtgcca ccaagggtct gcactaacca ggggtgtgcc cagaggctcg    59160
ctgcaggctt gaaattcctg cggagtcttg tgttttacct ggagcacatg tgcacagttt    59220
ccattctgct ccatagtatg cacatgtttg tatttatttc aacctaaaaa tgtttgtttc    59280
ccataactct ttgcgtataa ttgatactct acgtatttgt agcctctttt actcttttcc    59340
ctttcctcag ggagtggttt gctcatttag aaaaggccaa gatatatcac tgtagagttt    59400
cgtttctttt cttttcctcc accccccatc tttaccttgt tctgggagaa aggagaatta    59460
gaagtctgag ttgcagctgg agaaactggc aaattaaaat cacattggga aagagaatta    59520
ctgtgtttca caccatacca gtagaaatga caggctgttt tctgggggta gggatttggc    59580
ctttggtatt ggcagtcttg agaagtatta gataatcttt gctgatacag tctattttct    59640
cctcaggttc taggtcccaa ttctactgca aatagtatca tggcatctta tcagcaacag    59700
aagacttcgg ttcctgttct tggttagtat ttttttctcat ttaatattac aatactaagc    59760
agaaggacta tctttctgta agtattgaga agatcagcag tataaggaga gattggatac    59820 aattttttcac tacaaaaaat tgactacaat tcttcctcaa ttctaagacc gcatctttag    59880
tatgatcagt ttcatgcttc tagcggtggg ggacctggtg caggaaaatc cagcatgacc    59940
attgtatgtg taattttttaa aaatatttat gtggcatatg cttgttcata aaggcacacc    60000
acagttccag tttcagtcta aactgtctac atttacatat acatcaaaag attcttctga    60060
agcatcatta ctggctattg gcagttatgc tttgcatctt gggggcattt tcataaacct    60120
tgcttatgag tgggacctt ttattatgtt taggattgac aatataattt gaaggcaaat    60180
ccaaagaata ttagcatttt atacatattt cctgtttagt tatgcatgaa gtgttttatt    60240
tgttgagggg agatgattct caattagatt acttatatcc ctaaaaatta aaacccctaa    60300
gcgctttctt ttgaaagttg gttagaaaca tttgatgagt cagcttggga ctttcagtat    60360 ttgccctttac ttatagttgg atcaatgaag catcttagct ttgaaaagtg aatgatagtt    60420
tctaaaataa ttggcagttt taactgctat tatttgcatt tctagcatgt gacaagcaac    60480
tttctgaaat ttttttttcac cgaagtgcta cactgtaata gcattttgat gacatttgaa    60540
gtagcctgtg gggattcaaa ttaagtttga ctttaacagc ttatgttgct accaggaaga    60600
acagctacct tccatcccag ctaaactcat acatccagac tgtaactact gtattcctag    60660
ctcctcttct gtctagagaa tggcaaggtt cttttggtat cagtttcgac atatccactt    60720 attcctttt ttttcttaag tttttttcatt tagaaaaaaa aacagatggg gtcttaatat    60780
gttgcccagg ctggtctcag cctcctggtc tcaagtgatc ctcctgcctc ggcctcccaa    60840
agtgctggga ttacaggcgt ctgcccctgt gcccagccca cttatttccc agatgctagg    60900
aacttacatt agacctgagg ccatttggtc attgtttatt ttgtgctgta gtccaatcca    60960
gttgtgattt ctgcctcctg tgttcctcgt tgctggcctg atgctgacct tcaggttagg    61020
tcagtcccat cattcccag ggtattctag atggctttcc cacttcaaag agcactttct    61080
tgttttccag ctgagcctta aagacactct gtaaatttg agagccctc attatctgag    61140 tgttttattat cattacccctt gtggtttcaa ggatgtatag gaaaaggtaa gttcctataa    61200
ttcaaaaatt gccactgatg aactaatcac aaaattagtg ccactcaaat attactcagc    61260
tgcccctccc cagctaacaa tagttaagta tattggcaca tccccacaag tgaaatcaat    61320
```

```
gacttgatgg gtcatttctg attgtttcct gctttgatgc aatacaatat catgcagatc    61380
aattgcaagt cttgcaaaaa tttagtatta cataaaatag attaaaatga tattggaaaa    61440
gtacttgaat cacagctggg ttggacttgt tgcaattgat gacaaaataa gtgcttcaaa    61500
tgattttgac tatcaaagga ttgagagagg tccttagaaa aattgaaaag ccctcaagtt    61560 attttttataa aaatggcctt ttttgtgtgc tgtgaaatcc acatatggaa atgtgaaata    61620
tgtcatgtcc tgctgtcata taatttgtca gaataattac tttcttgccc aaaagtctgt    61680
actttgtgtt tatttcaagt taagtctaga atcaaatata gttgtagtta tgcctaatttt   61740 taaaaaatga gatagagcac attattttttg taactagttt ttttttttttt ttttttttttt 61800 tttttttttt ttcagacaga gtcttgctct gtggcccagg cgggagtgca gtggcgcaat    61860
ctcggctcac tgcaagctcc gcctcccggg ttcacgccat tctcctgcct cacccctcctg   61920 agtagctggg actacaggcg cccgccatca cgcccggcta attttttttgt attttttagta  61980 gagacgggt ttcaccgtgt tagccaggat ggtctcgatc tcctgacctc gtgatccacc     62040
cgcctcggcc tcccaaagtg ctgggattac aagcgtgagc caccgcgccc ggcctgtaac    62100
tagttttttt aagataaagt cttattccaa ctttaattgg aatttatgaa ataccttgtt    62160
gatagtgaat ttatttaagt agcctttttt cagtattgat attcttatat ctttatggca    62220
ccatttagtg gagagaaatg taaacaaaca taaagatgta gtattaaaatc ataactgcat    62280 aaaattaact gtagtatgta ctgcactact gtaataattt tgtagctacc tcctgttgct    62340
attgtggtga gtgagctcaa gtgttaccaa tatctgctta aaatgccatg tgccgctaac    62400
catctccaca tgagcagcac atgagagtct ccattaattg catatggcag cgaaaagtga    62460
tctcttgcat tgtcgtgtat tttttatcac gtttaatgta atatcgtaaa ccttaaataa    62520
caccatgaga cctataggaa gtaccacaag tgttgctccc aggaagcaga gaaagtcat    62580 aacattacaa gaaaaagttg acttgctcga tatgtactat agattgaggt ctgcagctgt    62640
agttgcccac cacttcaaga taaatgaacc cagtgcaagg actattataa aagaaaagga    62700
aatttatgaa gctgtcactg cagttatgcc agcaggcatg aaaaccttgt acttttttgca   62760 aaataccttt ttatgttgta ttgaagatgc agcttttatg tgggtgcagg attgctatga    62820
gaaaggcata cctatacaac tattatgatt tgagaaaaag cacagtcatt gtatgagaac    62880
ttaaagcaaa aagatgaagg atcaaagctg gagaatttaa tgccagcaaa ggatggtttg    62940
ataattttag aaagaggttt ggctttgtaa atgtctggat aataggaaaa gcagctcctg    63000
ccatccagga ggcagcagca aaggcagtca ggtttatgat caggactgcc cttatctgta    63060
aagctgctaa cccccgagcc tggaagggaa aagattaaca ccagctgcca ggcttttggt    63120
tgtaccatac aacaagaagg cttggacaag gagaacactt tttctggatt ggttccattg    63180
tcgatttgtc cctgaagtta agtagtatct tgccagtaag gggactgcct tttaaagttc    63240
ttttgatact ggagaatgcc cgaggccacc ccaaactcca tgagttcaac accgaagaca    63300
ttgaagtgat ctacttgccc ccaaacacac atctctaatt cagcctctag atcagggtgt    63360
cataaggacc tttaaggctc gttacaaaca gtactctata gaaaggattg tcaaatgtat    63420
ggaaagaaac cttgacagaa catgaaagtc tgaaagaatt acaccatcaa tgatgccatc    63480
attgttatag aaaaagctgt gaaagccatc aagcccagga caataaattc ctgctagaga    63540
aaactgtgtc cagatgtgca tgacttcaca ggctttacga cagccaatca aggaaatcat    63600 gaaaagatt gtggatctgg cacaaaaaaa aaaaaaaaaa aaaaaaatgg tgcatgaagg     63660
atttcaagat aggaatcttg gagaaattca agaggtgata gacatcacac cggaggaatt    63720
```

```
aacagaagat gacttgatgg agatgagtac ttccaaacca gcgccagaca atgaggaaga   63780
ttacataaaa gaagcagtgc cagaaaataa attgacattt gttccaaagg ttccaattat   63840
tcaagactgc ctttggcttc tttacaaca tggatgattc tatgttatgg gcactgaaac   63900
taaaagaaac tgtggaagga ttggtacctt agagaaatga aaaagcaaaa acatcagaaa   63960
ttatggtgta tttctgtaaa gttagtgaca ctgagtgtgc ccacctctct tgcctcctct   64020
ttaacctccc ctacctgttt catctctacc acccctgaga cagcaagacc aacccctcca   64080
cttcctcctc tacttcagcc tactcaacgt ggagatgaca agatgaaga cctttatgat    64140 gatccacttc catttaatga atagtaaata ttgttttctt tatgattttc ttaatatttt   64200
cttttctcta gcttactta ttgtaggaat gtagtatata atacatataa catacaaaac   64260
atttgttaac tgactttta tgctgccaat acactgccga acaacagtaa gctattggta   64320
cttgagtttt ggagattcag aagttaaaca tggggccagg tgtggtggct cacacctgta  64380
atcccagcac tttgggaggc tgaggtgggt ggaacgagac caggagtttt gagagtagcc  64440
tgggcagcat ggtgaaacct tgtctctaca gaaattagcc aggtatggtg gtgtacactt  64500
gtagtcccag ctactggga ggctgaggca ggagaatcgc ttgaacccag ggggtcgagg   64560
ctgcagtgag tcatgatcgt gccactgcac tccaacctgg gcaacaaaat gagaccctgt   64620
ctcaaaaaaa gaaaaaaaaa aggtatatgc agattttga ctgtgcaggg gggtccgcac   64680
ccataaccct acattcaagg atcaactgta attttcatg cctgcatggc tcatatgtac   64740
agatttactg ctggaagttt atcataaata atgctgaaaa agaaaatcct tatatataca   64800
tattttctcc tatctctgct tgcagtatat gattcctggt tagaaaagaa acttaacaaa   64860
tctaagtgaa agagtgcctg ggagttttag gttacaatga cagaatcttt tcctaaccct   64920
ctctctccat tcactttttt taaagcaggg gcatctttat tgatcaacat gtttgtcgaa   64980
gtttcatcat aaagtagttc ctgtccatta acttcactta ctgaatatgt gctatcacat   65040
tttgctattc cttaaaaatt gagctagact ttacatatag tgaaatgcag agatttcagg   65100
tgtacaattt gatgagtttt aataaatgta tacagccatg tgactgctgc caccacccct   65160
cccaccagtt tgaaatacag aacattcttc cactttgaat cactgggtga gcatgcctga   65220
ggttgaaatg cagtccctcc tctcagggcg gggcctccag gttgtgttg ctctgacctg    65280 gaggttgcag gggtagcaga cacatgaact ctggctctga tggtcttatt gctgcaaact   65340
ccacctgcct agtttgttta gtttagagtt actgcctcag cgccctccaa caagagtatg   65400
tctgtcacaa tttcccttcc ttttcttgctt ttagatgctg agcttttat accaccaaag   65460 atcaacagaa gaacccagtg gaagctgagc ctgctagact gagtgactgc agttaggagg   65520
gatccgacag agaagaccat ttccactcat tcctgttgtc ctaccacccc ttgctctttg   65580
agggctggct attgagaact ggaaagagta aaatgataac ttaccttagc attgccaaga   65640
acttcagcag acaacaagca attctattta tttatgttg tgtatacatc ttgatcatta   65700
gcaagacatt aagctttaac cattatggca ccattttgtg agaatgattg ttctttcact   65760
tgggctgttt gagagcataa ttatggtaat catgagatta atgttcatg atttctacct   65820 ccaaagtgtg aagacaagta aaacaatgtt tctaaattgt cttatttgt tggcggagaa    65880 gattacaatg gctattagtg ctacatttgg tcaaatgtaa tcacttaaat agcttcttgt   65940
caccttaaac taaagcagaa taaaagtat cctttgaaat tataagccct cctttgctga    66000
cagctattat tttgtaacat cttaccaggt catgtgcttt cagttataac tgggctgagc   66060
```

```
ctcctataat tacaatgtct atagggactg ttttactgcc tgtgtatttt ctgctagaga    66120
gttagcaatg ttagagctag aacagattag aatttctaaa cagtatcatg cacagttggt    66180
gtgagtgatc agtgtgcatt gtatggcatg catggttgtg aattattctc tgttctccaa    66240
atactgtttc tttaactcag atattttgt tagtgtctag gccacttcat ttattttcg      66300 tcatggtact ttactgactt ctctttattc aattctccac gccctcacca aaaaaaactg    66360
tctcaaaatg agaatatttt attttcatgg tgagtctaga aaacgcccac ttcattctga    66420
ttaaaaattc ttccatgttt taaatatcag aaccagacct ttcttactgt gtatcttagc    66480
ccatttgtgt ctctataaca acaaccagct ttcaaaggaa ctaatagagt gaaaactcac    66540
tcattaccac gaggatggca caagcgattc acgtaggatc tgcccctgtg accaaaacac    66600
ctcccattgg gccccacttc caacactggt gatcacattt caacatgagg tttagggaaa    66660
caaatgccta aactacagca ctgtacataa actaacagga aatgctgctt ttgatcctca    66720
aagaagtgat atagccaaaa ttgtaattta agaagccttt cccagtatag caagatgtta    66780
actatagaat caatctagga gtattcactg taaaattcaa cttttctgta tgtttgaaca    66840
ttttcacaat ctcataggag ttttaaaaa gaagagaaag aagatatact ttgctttgga    66900
gaaatctact ttttgactta catgggtttg ctgtaattaa gtgcccaata ttgaaaggct    66960
gcaagtactt tgtaatcact ctttggcatg ggtaaataag catggtaact tatattgaaa    67020
tatagtgctc ttgctttgga taactgtaaa gggacccatg ctgatagact ggaaatagaa    67080
gtaaatgtgt ttattgataa tggtgtgaat tttcctggac attcagtttc cttaaataat    67140
gtattgaagc agcaagaaat aatttgtttg aatgcaaatt actatcaatt actgtttctc    67200
tcatctgagc aggattggat tttgttcctt tttagaagaa gcaggcagga ggagaccttc    67260
caaattgagg caaagccaag aattgaatat tcatggggga aaattgagtg tatgagaaaa    67320
ggaggaaact cctctgagtg atgaatgctt aatttggggg aaagagtctg tcaagtttta    67380
gaaaagagta cataaatttg gatcctgtcc caaagcaagt tcatgctgca ataagctaaa    67440
accttcactt ttcttggttc cattgagtca gatagctttg ctcagatgct ctaaacttca    67500
agaaggaact tgcagaagac tgtcttcttc ggtcaaagtg cattttaaat ttatgctttt    67560
gaaaaaactg aggccgggtg cggtggatca cacctgt                             67597
```

<210> SEQ ID NO 2
<211> LENGTH: 46
<212> TYPE: DNA
<213> ORGANISM: Artificial sequence
<220> FEATURE:
<223> OTHER INFORMATION: Primer

<400> SEQUENCE: 2
ggggaaggat ccgccatgga gttaatggtg tgtttagcat tacagg                   46

<210> SEQ ID NO 3
<211> LENGTH: 42
<212> TYPE: DNA
<213> ORGANISM: Artificial sequence
<220> FEATURE:
<223> OTHER INFORMATION: Primer

<400> SEQUENCE: 3
ggggaatcta gacttagggt tatgatcata aatcagattg ag                       42

<210> SEQ ID NO 4
<211> LENGTH: 45

```
<212> TYPE: DNA
<213> ORGANISM: Artificial sequence
<220> FEATURE:
<223> OTHER INFORMATION: Primer

<400> SEQUENCE: 4
ggggaatcta gattacttca attctgtaaa aaacaagtta atatg          45

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
taatacgact cactataggg                                       20

<210> SEQ ID NO 6
<211> LENGTH: 24
<212> TYPE: DNA
<213> ORGANISM: Artificial sequence
<220> FEATURE:
<223> OTHER INFORMATION: Primer

<400> SEQUENCE: 6
cttagggtta tgatcataaa tcag                                  24

<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7
ttcaattctg taaaaaacaa g                                     21

<210> SEQ ID NO 8
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 8
agagaattac cacaa                                            15

<210> SEQ ID NO 9
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 9
ttcacagaga attac                                            15

<210> SEQ ID NO 10
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 10
```

```
aactcttcac agaga                                                    15

<210> SEQ ID NO 11
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 11
tacctaactc ttcac                                                    15

<210> SEQ ID NO 12
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 12
cattttacct aactc                                                    15

<210> SEQ ID NO 13
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 13
tacaccattt tacct                                                    15

<210> SEQ ID NO 14
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 14
caggatacac cattt                                                    15

<210> SEQ ID NO 15
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 15
atagccagga tacac                                                    15

<210> SEQ ID NO 16
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 16
tttaaatagc cagga                                                    15

<210> SEQ ID NO 17
<211> LENGTH: 15
<212> TYPE: DNA
<213> ORGANISM: Artificial sequence
```

```
<220> FEATURE:
<223> OTHER INFORMATION: Synthetic oligonucleotide

<400> SEQUENCE: 17
aaacatttaa atagc                                                    15

<210> SEQ ID NO 18
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 18
gtagaaaaca tttaa                                                    15

<210> SEQ ID NO 19
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 19
attaagtaga aaaca                                                    15

<210> SEQ ID NO 20
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 20
ttttaattaa gtaga                                                    15

<210> SEQ ID NO 21
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 21
aacattttta attaa                                                    15

<210> SEQ ID NO 22
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 22
gcagtaacat tttta                                                    15

<210> SEQ ID NO 23
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 23
ttaaagcagt aacat                                                    15
```

<210> SEQ ID NO 24
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 24
ataaattaaa gcagt                                                          15

<210> SEQ ID NO 25
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 25
cttaaataaa ttaaa                                                          15

<210> SEQ ID NO 26
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 26
gtttcccctt ggcat                                                          15

<210> SEQ ID NO 27
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 27
tctaagtttc ccctt                                                          15

<210> SEQ ID NO 28
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 28
caacttctaa gtttc                                                          15

<210> SEQ ID NO 29
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 29
atgaacaact tctaa                                                          15

<210> SEQ ID NO 30
<211> LENGTH: 15
<212> TYPE: DNA
<213> ORGANISM: Artificial sequence
<220> FEATURE:
<223> OTHER INFORMATION: Synthetic oligonucleotide

```
<400> SEQUENCE: 30
cgatgatgaa caact                                                      15

<210> SEQ ID NO 31
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 31
gggctcgatg atgaa                                                      15

<210> SEQ ID NO 32
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 32
aaccagggct cgatg                                                      15

<210> SEQ ID NO 33
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 33
gctaaaacca gggct                                                      15

<210> SEQ ID NO 34
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 34
tctgagctaa aacca                                                      15

<210> SEQ ID NO 35
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 35
ccgaatctga gctaa                                                      15

<210> SEQ ID NO 36
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 36
cacttccgaa tctga                                                      15

<210> SEQ ID NO 37
```

```
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 37
ccaaccactt ccgaa                                                     15

<210> SEQ ID NO 38
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 38
ttgtccaacc acttc                                                     15

<210> SEQ ID NO 39
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 39
tacaatggcg cttac                                                     15

<210> SEQ ID NO 40
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 40
aacagtacaa tggcg                                                     15

<210> SEQ ID NO 41
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 41
tcgcaaacag tacaa                                                     15

<210> SEQ ID NO 42
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 42
actagtcgca aacag                                                     15

<210> SEQ ID NO 43
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 43
```
agctaactag tcgca                                                    15

<210> SEQ ID NO 44
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 44
tcacaagcta actag                                                    15

<210> SEQ ID NO 45
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 45
ataaatcaca agcta                                                    15

<210> SEQ ID NO 46
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 46
cacacataaa tcaca                                                    15

<210> SEQ ID NO 47
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 47
gtcttcacac ataaa                                                    15

<210> SEQ ID NO 48
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 48
ttattgtctt cacac                                                    15

<210> SEQ ID NO 49
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 49
aatacttatt gtctt                                                    15

<210> SEQ ID NO 50
<211> LENGTH: 15
<212> TYPE: DNA

```
<213> ORGANISM: Artificial sequence
<220> FEATURE:
<223> OTHER INFORMATION: Synthetic oligonucleotide

<400> SEQUENCE: 50
aataaaatac ttatt                                                   15

<210> SEQ ID NO 51
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 51
attgtaataa aatac                                                   15

<210> SEQ ID NO 52
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 52
tcgaaattgt aataa                                                   15

<210> SEQ ID NO 53
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 53
agttctcgaa attgt                                                   15

<210> SEQ ID NO 54
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 54
ttttaagttc tcgaa                                                   15

<210> SEQ ID NO 55
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 55
cataatttta agttc                                                   15

<210> SEQ ID NO 56
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 56
cttttcataa tttta                                                   15
```

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
tttatatgga tgttaaaaag                                               20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
aaaagcattt tgtttcacaa                                               20

<210> SEQ ID NO 59
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 59
attttgtctg aaacc                                                    15

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
tcgcaaacag tacaatggcg                                               20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
gtcgcaaaca gtacaatggc                                               20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
agtcgcaaac agtacaatgg                                               20

<210> SEQ ID NO 63
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 63
tagtcgcaaa cagtacaatg                                              20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
ctagtcgcaa acagtacaat                                              20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
actagtcgca aacagtacaa                                              20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
aactagtcgc aaacagtaca                                              20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
taactagtcg caaacagtac                                              20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
ctaactagtc gcaaacagta                                              20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
gctaactagt cgcaaacagt                                              20